US00RE43135E

(19) United States
(12) Reissued Patent
Bojsen et al.

(10) Patent Number: US RE43,135 E
(45) Date of Reissued Patent: Jan. 24, 2012

(54) METHOD OF IMPROVING DOUGH AND BREAD QUALITY

(75) Inventors: Kirsten Bojsen, Hellerup (DK); Charlotte Horsman Poulsen, Braband (DK); Jorn Borch Soe, Tilst (DK)

(73) Assignee: Danisco A/S, Copenhagen (DK)

(21) Appl. No.: 11/903,211

(22) Filed: Sep. 20, 2007

Related U.S. Patent Documents

Reissue of:
(64) Patent No.: 6,967,035
Issued: Nov. 22, 2005
Appl. No.: 10/150,429
Filed: May 17, 2002

U.S. Applications:
(60) Provisional application No. 60/347,007, filed on Jan. 9, 2002.

(30) Foreign Application Priority Data

May 18, 2001 (GB) ..... 0112226

(51) Int. Cl.
*A21D 8/04* (2006.01)

(52) U.S. Cl. ..... 426/20; 426/18; 426/549; 426/653

(58) Field of Classification Search ..... 426/18, 426/19, 20, 61, 549, 552, 553, 653; 435/198
See application file for complete search history.

(56) References Cited

U.S. PATENT DOCUMENTS

| | | | |
|---|---|---|---|
| 2,888,385 | A | 5/1959 | Grandel |
| 3,260,606 | A | 7/1966 | Azuma |
| 3,368,903 | A | 2/1968 | Johnson |
| 3,520,702 | A | 7/1970 | Menzi |
| 3,634,195 | A | 1/1972 | Melaschouris |
| 3,652,397 | A | 3/1972 | Pardun |
| 3,677,902 | A | 7/1972 | Aunstrup |
| 3,817,837 | A | 6/1974 | Rubenstein et al. |
| 3,850,752 | A | 11/1974 | Wilhelmus et al. |
| 3,852,260 | A | 12/1974 | Knutsen |
| 3,939,350 | A | 2/1976 | Kronick et al. |
| 3,973,042 | A | 8/1976 | Kosikowski |
| 3,996,345 | A | 12/1976 | Ullman et al. |
| 4,034,124 | A | 7/1977 | Van Dam |
| 4,065,580 | A | 12/1977 | Feldman |
| 4,160,848 | A | 7/1979 | Vidal |
| 4,202,941 | A | 5/1980 | Terada |
| 4,275,149 | A | 6/1981 | Litman et al. |
| 4,277,437 | A | 7/1981 | Maggio |
| 4,366,241 | A | 12/1982 | Tom et al. |
| 4,399,218 | A | 8/1983 | Gauhl |
| 4,567,046 | A | 1/1986 | Inoue |
| 4,683,202 | A | 7/1987 | Mullis |
| 4,689,297 | A | 8/1987 | Good |
| 4,707,291 | A | 11/1987 | Thom |
| 4,707,364 | A | 11/1987 | Barach |
| 4,708,876 | A | 11/1987 | Yokoyama |
| 4,798,793 | A | 1/1989 | Eigtved |
| 4,808,417 | A | 2/1989 | Masuda |
| 4,810,414 | A | 3/1989 | Huge-Jensen |
| 4,814,331 | A | 3/1989 | Kerkenaar |
| 4,816,567 | A | 3/1989 | Cabilly et al. |
| 4,818,695 | A | 4/1989 | Eigtved |
| 4,826,767 | A | 5/1989 | Hansen |
| 4,865,866 | A | 9/1989 | Moore |
| 4,904,483 | A | 2/1990 | Christensen |
| 4,916,064 | A | 4/1990 | Derez |
| 5,112,624 | A | 5/1992 | Johna |
| 5,213,968 | A | 5/1993 | Castle |
| 5,219,733 | A | 6/1993 | Myojo |
| 5,219,744 | A | 6/1993 | Kurashige |
| 5,232,846 | A | 8/1993 | Takeda |
| 5,264,367 | A | 11/1993 | Aalrust |
| 5,273,898 | A | 12/1993 | Ishii |
| 5,288,619 | A | 2/1994 | Brown |
| 5,290,694 | A | 3/1994 | Nakanishi |
| 5,310,679 | A | 5/1994 | Artiss et al. |
| 5,378,623 | A | 1/1995 | Hattori |
| 5,523,237 | A | 6/1996 | Budtz |
| 5,536,661 | A | 7/1996 | Boel |
| 5,558,781 | A | 9/1996 | Buchold |
| 5,650,188 | A | 7/1997 | Gaubert |
| 5,674,707 | A | 10/1997 | Hintz et al. |
| 5,677,160 | A | 10/1997 | Oester |
| 5,695,802 | A | 12/1997 | Van Den Ouweland |
| 5,716,654 | A | 2/1998 | Groenendaal |
| 5,741,665 | A | 4/1998 | Kato et al. |

(Continued)

FOREIGN PATENT DOCUMENTS

| | | |
|---|---|---|
| AR | 249546 | 12/1996 |

(Continued)

OTHER PUBLICATIONS

AACC Method 54-21 Farinograph Method for Flour Nov. 3, 1999.
Anderson D, "A Primer in Oils Processing Technology" in Bailey's Industrial Oil and Fat Products, Sixth edition, John Wiley, 2005, vol. 5, chapter 1, p. 1-56. ISBN 978047138401.
Anguita et al, Appl. Environ. Microbiol., vol. 59, No. 8, p. 2411-2417, 1993.
AOAC Official method 999.10 (Lead, Cadmium, Zinc, Copper, and Iron in Foods Atomic absorption Spectrophotometry after Microwave Digestion, First Action 1999 NMKL-AOAC Method.
AOCS Introduction to the Processing of Fats and Oils p. 111-16-111-19. Four modules on CD-ROM. American Oil Chemists Society, 2003.
AOCS Method 2c-25 1997 Moisture and Volatile Matter Air Oven Method.
AOCS Official Method Ca 20-99: Analysis of Phosphorus in oil by inductively Coupled Plasma Optical Emission Spectroscopy.
Archer D.B. & Peberdy, The Molecular Biology of Secreted Enzyme Production by Fungi, Critical Reviews in Biotechnology, 1997, vol. 17, No. 4, p. 273-306.

(Continued)

*Primary Examiner* — Leslie Wong
(74) *Attorney, Agent, or Firm* — Vedder Price P.C.; Thomas J. Kowalski; Heidi Lunasin

(57) ABSTRACT

A method of preparing a flour dough, said method comprising adding to the dough components an enzyme that under dough conditions is capable of hydrolysing a glycolipid and a phospholipid, wherein said enzyme is incapable, or substantially incapable, of hydrolysing a triglyceride and/or a 1-monoglyceride, or a composition comprising said enzyme, and mixing the dough components to obtain the dough.

34 Claims, 13 Drawing Sheets

U.S. PATENT DOCUMENTS

Figure 1:
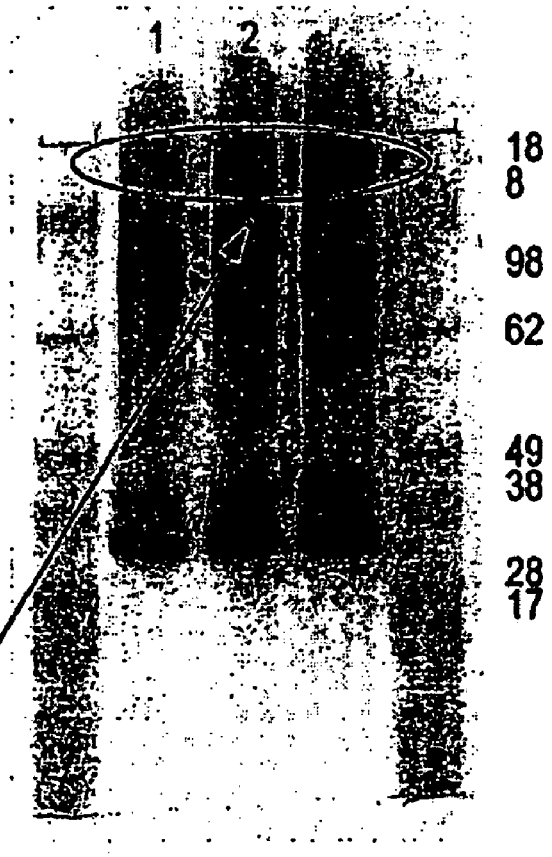

| | | | |
|---|---|---|---|
| 5,763,383 | A | 6/1998 | Hashida |
| 5,766,912 | A | 6/1998 | Boel |
| 5,776,741 | A | 7/1998 | Pedersen |
| 5,814,501 | A | 9/1998 | Becker |
| 5,821,102 | A | 10/1998 | Berka |
| 5,824,354 | A | 10/1998 | Ritter et al. |
| 5,827,719 | A | 10/1998 | Sandal |
| 5,830,736 | A | 11/1998 | Oxenboll |
| 5,834,280 | A | 11/1998 | Oxenboll |
| 5,856,163 | A | 1/1999 | Hashida |
| 5,863,759 | A | 1/1999 | Boel |
| 5,869,438 | A | 2/1999 | Svendsen |
| 5,874,558 | A | 2/1999 | Boel |
| 5,879,920 | A | 3/1999 | Dale |
| 5,892,013 | A | 4/1999 | Svendsen |
| 5,914,306 | A | 6/1999 | Svendsen |
| 5,916,619 | A | 6/1999 | Miyazaki |
| 5,919,746 | A | 7/1999 | Hirayama |
| 5,929,017 | A | 7/1999 | Gormsen |
| 5,965,384 | A | 10/1999 | Boel |
| 5,965,422 | A | 10/1999 | Loffler |
| 5,976,855 | A | 11/1999 | Svendsen |
| 5,989,599 | A | 11/1999 | Chmiel |
| 5,990,069 | A | 11/1999 | Andre |
| 6,001,586 | A | 12/1999 | Schellenberger |
| 6,001,640 | A | 12/1999 | Loeffler |
| 6,020,180 | A | 2/2000 | Svendsen |
| 6,066,482 | A | 5/2000 | Steffens |
| 6,074,863 | A | 6/2000 | Svendsen |
| 6,103,505 | A | 8/2000 | Clausen |
| 6,110,508 | A | 8/2000 | Olesen |
| 6,140,094 | A | 10/2000 | Loffler |
| 6,143,543 | A | 11/2000 | Michelsen |
| 6,143,545 | A | 11/2000 | Clausen |
| 6,146,869 | A | 11/2000 | Harris |
| 6,156,548 | A | 12/2000 | Christensen |
| 6,180,406 | B1 | 1/2001 | Stemmer |
| 6,254,645 | B1 | 7/2001 | Kellis |
| 6,254,903 | B1 | 7/2001 | Schuster et al. |
| 6,344,328 | B1 | 2/2002 | Short |
| 6,350,604 | B1 | 2/2002 | Hirayama |
| 6,358,543 | B1 | 3/2002 | Soe |
| 6,361,974 | B1 | 3/2002 | Short |
| 6,365,204 | B1 | 4/2002 | Spendler |
| 6,432,898 | B1 | 8/2002 | Rey |
| 6,495,357 | B1 | 12/2002 | Fuglsang |
| 6,506,588 | B2 | 1/2003 | Tsutsumi |
| 6,509,182 | B2 | 1/2003 | Tsutsumi |
| 6,511,837 | B2 | 1/2003 | Tsutsumi |
| 6,514,739 | B1 | 2/2003 | Udagawa |
| 6,558,715 | B1 | 5/2003 | Rey |
| 6,582,942 | B1 | 6/2003 | Christensen |
| 6,624,129 | B1 | 9/2003 | Borch |
| 6,645,749 | B2 | 11/2003 | Vind |
| 6,682,922 | B2 | 1/2004 | Berka |
| 6,686,189 | B2 | 2/2004 | Rey |
| 6,726,942 | B2 | 4/2004 | Soe et al. |
| 6,730,346 | B2 | 5/2004 | Rey |
| 6,815,190 | B1 | 11/2004 | Abo |
| 6,852,346 | B2 | 2/2005 | Søe et al. |
| 6,866,837 | B2 | 3/2005 | Reubi et al. |
| 6,936,289 | B2 | 8/2005 | Olsen et al. |
| 6,964,944 | B1 | 11/2005 | Callisen et al. |
| 6,967,035 | B2 | 11/2005 | Kolkman et al. |
| 7,226,771 | B2 | 6/2007 | Gramatikova et al. |
| 7,718,204 | B2 | 5/2010 | Soe et al. |
| 2002/0098536 | A1 | 7/2002 | Norinobu |
| 2002/0110854 | A1 | 8/2002 | Tsutsumi |
| 2002/0142434 | A1 | 10/2002 | Tsutsumi |
| 2002/0168746 | A1 | 11/2002 | Tsutsumi |
| 2002/0182734 | A1 | 12/2002 | Diaz-Torres |
| 2003/0003561 | A1 | 1/2003 | Vind |
| 2003/0028923 | A1 | 2/2003 | Lardizabal |
| 2003/0040450 | A1 | 2/2003 | Rey |
| 2003/0074695 | A1 | 4/2003 | Farese |
| 2003/0100092 | A1 | 5/2003 | Berka |
| 2003/0119164 | A1 | 6/2003 | Udagawa |
| 2003/0148495 | A1 | 8/2003 | Hastrup |
| 2003/0180418 | A1 | 9/2003 | Rey |
| 2003/0185939 | A1 | 10/2003 | Nielsen |
| 2003/0215544 | A1 | 11/2003 | Nielsen |
| 2004/0005399 | A1 | 1/2004 | Chakrabarti |
| 2004/0142441 | A1 | 7/2004 | Weiss et al. |
| 2004/0235106 | A1 | 11/2004 | Kapeller-Libermann |
| 2004/0235119 | A1 | 11/2004 | Hoppe et al. |
| 2005/0059130 | A1 | 3/2005 | Bojsen |
| 2005/0059131 | A1 | 3/2005 | Bisgard-Frantzen |
| 2005/0118697 | A1 | 6/2005 | Budolfsen |
| 2005/0142647 | A1 | 6/2005 | Wassell |
| 2006/0040357 | A1 | 2/2006 | Bandaru et al. |
| 2006/0075518 | A1 | 4/2006 | Yaver et al. |
| 2006/0141457 | A1 | 6/2006 | Lindqvist et al. |
| 2007/0026106 | A1 | 2/2007 | Kreij et al. |
| 2007/0122525 | A1 | 5/2007 | Kreij |
| 2008/0063783 | A1 | 3/2008 | Kreij et al. |
| 2008/0070287 | A1 | 3/2008 | Soe et al. |
| 2008/0131936 | A1 | 6/2008 | Miasnikov et al. |
| 2008/0187643 | A1 | 8/2008 | Horlacher et al. |

FOREIGN PATENT DOCUMENTS

| | | |
|---|---|---|
| AR | P000105426 | 10/2000 |
| AR | P040101441 | 4/2004 |
| AT | 110 768 | 8/1987 |
| AU | 570720 | 9/1984 |
| AU | 723031 | 4/1998 |
| AU | 754470 | 11/1999 |
| BR | 8404421-7 | 4/1984 |
| CA | 1270781 | 6/1990 |
| CA | 2012723 | 9/1990 |
| CA | 2134597 | 10/1994 |
| CA | 2224143 | 12/1996 |
| CA | 2403025 | 4/2004 |
| CN | 101200754 | 12/2007 |
| DE | 2817087 | 11/1978 |
| DE | 19620649 | 11/1997 |
| DE | 69129988 | 3/1999 |
| DE | 69330066 | 10/2001 |
| DE | 10119972 | 5/2002 |
| DE | 69527835 | 4/2003 |
| DE | 69528070 | 6/2003 |
| DE | 69333065 | 7/2003 |
| DE | 69904161 | 7/2003 |
| DE | 69716711 | 9/2003 |
| DE | 69531538 | 6/2004 |
| DE | 69819782 | 9/2004 |
| DK | 3106.200 | 1/1989 |
| DK | 157560 | 1/1990 |
| DK | PA0888/92 | 7/1992 |
| DK | 0217/94 | 2/1994 |
| DK | PA0830/95 | 7/1995 |
| DK | PA1096/95 | 9/1995 |
| DK | 152763 | 3/1998 |
| DK | PA0543/98 | 4/1998 |
| DK | PA199801572 | 11/1998 |
| DK | PA5677000 | 12/1998 |
| DK | PA199801604 | 12/1998 |
| DK | PA199901736 | 12/1999 |
| DK | PA200000989 | 6/2000 |
| DK | PA200000991 | 6/2000 |
| DK | PA200100285 | 2/2001 |
| DK | PA200100843 | 5/2001 |
| DK | EP659049 | 6/2001 |
| DK | EP0784674 | 11/2002 |
| DK | EP0869167 | 1/2003 |
| DK | EP1073339 | 1/2003 |
| DK | PA200300634 | 4/2003 |
| DK | EP0746608 | 10/2003 |
| DK | EP1042458 | 3/2004 |
| EP | 0064855 | 11/1982 |
| EP | 0010296 | 12/1982 |
| EP | 0109244 | 5/1984 |
| EP | 0130064 | 1/1985 |
| EP | 0140542 | 5/1985 |
| EP | 0167309 | 1/1986 |
| EP | 0171995 | 2/1986 |
| EP | 0205208 | 12/1986 |
| EP | 0206390 | 12/1986 |

| | | |
|---|---|---|
| EP | 0214761 | 3/1987 |
| EP | 0257388 | 3/1988 |
| EP | 0260573 | 3/1988 |
| EP | 0334462 | 9/1989 |
| EP | 0195311 | 6/1990 |
| EP | 0375102 | 6/1990 |
| EP | 0426211 | 5/1991 |
| EP | 0445692 | 9/1991 |
| EP | 0449375 | 10/1991 |
| EP | 0468731 | 1/1992 |
| EP | 0493045 | 7/1992 |
| EP | 0583265 | 10/1992 |
| EP | 0513709 | 11/1992 |
| EP | 0542351 | 5/1993 |
| EP | 0558112 | 9/1993 |
| EP | 0258068 | 11/1993 |
| EP | 0238023 | 12/1993 |
| EP | 0575133 | 12/1993 |
| EP | 0580252 | 1/1994 |
| EP | 0258068 | 8/1994 |
| EP | 0622446 | 11/1994 |
| EP | 0652289 | 5/1995 |
| EP | 0654527 | 5/1995 |
| EP | 0396162 | 9/1995 |
| EP | 0687414 | 12/1995 |
| EP | 0 585 988 | 3/1996 |
| EP | 0585988 | 3/1996 |
| EP | 0721981 | 7/1996 |
| EP | 0752008 | 1/1997 |
| EP | 0776604 | 6/1997 |
| EP | 0531104 | 8/1997 |
| EP | 0808903 | 11/1997 |
| EP | 0682116 | 12/1997 |
| EP | 0812910 | 12/1997 |
| EP | 0305216 | 3/1998 |
| EP | 0847701 | 6/1998 |
| EP | 0548228 | 8/1998 |
| EP | 0866796 | 9/1998 |
| EP | 0702712 | 12/1998 |
| EP | 0882797 | 12/1998 |
| EP | 0897667 | 2/1999 |
| EP | 0913092 | 5/1999 |
| EP | 0913468 | 5/1999 |
| EP | 0321811 | 12/1999 |
| EP | 1131416 | 6/2000 |
| EP | 0739985 | 11/2000 |
| EP | 1057415 | 12/2000 |
| EP | 1071734 | 1/2001 |
| EP | 1073339 | 2/2001 |
| EP | 0659049 | 3/2001 |
| EP | 1103606 | 5/2001 |
| EP | 1108360 | 6/2001 |
| EP | 1138763 | 10/2001 |
| EP | 1145637 | 10/2001 |
| EP | 0191217 | 2/2002 |
| EP | 0869167 | 2/2002 |
| EP | 1193314 | 4/2002 |
| EP | 0746618 | 8/2002 |
| EP | 1233676 | 8/2002 |
| EP | 0648263 | 9/2002 |
| EP | 0784674 | 9/2002 |
| EP | 1275711 | 1/2003 |
| EP | 1285969 | 2/2003 |
| EP | 1298205 | 4/2003 |
| EP | 0635053 | 6/2003 |
| EP | 0675944 | 6/2003 |
| EP | 0817838 | 6/2003 |
| EP | 1280919 | 6/2003 |
| EP | 0746608 | 8/2003 |
| EP | 0851913 | 5/2004 |
| EP | 1262562 | 6/2004 |
| EP | 1433852 | 6/2004 |
| EP | 0977869 | 7/2004 |
| EP | 0743017 | 9/2004 |
| EP | 0675949 | 10/2004 |
| EP | 0880590 | 10/2004 |
| EP | 0897423 | 10/2004 |
| EP | 1466980 | 10/2004 |
| EP | 0839186 | 11/2004 |
| EP | 1162889 | 2/2005 |
| EP | 1532863 | 5/2005 |
| EP | 1559788 | 8/2005 |
| EP | 1363506 | 11/2005 |
| EP | 01624047 A1 | 2/2006 |
| EP | 01624047 B1 | 2/2006 |
| EP | 1762622 | 3/2007 |
| EP | 1788080 | 5/2007 |
| ES | 535608 | 9/1984 |
| ES | 535602 | 10/1984 |
| ES | 535609 | 3/1985 |
| GB | 1086550 | 10/1967 |
| GB | 1442418 | 7/1976 |
| GB | 1577933 | 10/1980 |
| GB | 2264429 | 9/1993 |
| GB | 0028701.1 | 11/2000 |
| GB | 2 358 784 A | 8/2001 |
| GB | 2358784 | 8/2001 |
| GB | 0301117.8 | 1/2003 |
| GB | 0301118.6 | 1/2003 |
| GB | 0301119.4 | 1/2003 |
| GB | 0301120.2 | 1/2003 |
| GB | 0301121.0 | 1/2003 |
| GB | 0301122.8 | 1/2003 |
| GB | 2379165 | 3/2003 |
| GB | 2267033 | 11/2003 |
| GB | 0330016.7 | 12/2003 |
| JP | 59183881 | 4/1960 |
| JP | 48-16612 | 5/1973 |
| JP | 5476892 | 6/1979 |
| JP | 55131340 | 10/1980 |
| JP | 57-189638 | 11/1982 |
| JP | 57-189637 | 12/1982 |
| JP | 60078529 | 5/1985 |
| JP | 62118883 | 11/1985 |
| JP | 63042691 | 8/1986 |
| JP | 62061590 | 3/1987 |
| JP | 62285749 | 12/1987 |
| JP | 10203974 | 8/1988 |
| JP | 1252294 | 10/1989 |
| JP | 2-49593 | 2/1990 |
| JP | 2-153997 | 6/1990 |
| JP | 04075592 | 3/1992 |
| JP | 6014773 | 3/1992 |
| JP | 4121186 | 4/1992 |
| JP | 15626492 | 6/1992 |
| JP | 04200339 | 7/1992 |
| JP | 4300839 | 10/1992 |
| JP | 4327536 | 11/1992 |
| JP | 04-370055 | 12/1992 |
| JP | 5211852 | 8/1993 |
| JP | 6345800 | 12/1994 |
| JP | 07-079687 | 3/1995 |
| JP | 8268882 | 4/1995 |
| JP | 7231788 | 9/1995 |
| JP | 7330794 | 12/1995 |
| JP | 8143457 | 6/1996 |
| JP | 8266213 | 10/1996 |
| JP | 9040689 | 2/1997 |
| JP | 10155493 | 6/1998 |
| JP | 10155493 A | 6/1998 |
| JP | 11-228986 | 8/1999 |
| JP | 11290078 | 10/1999 |
| JP | 2000226335 | 8/2000 |
| JP | 03/024096 | 7/2001 |
| JP | 3553958 | 5/2004 |
| KR | 93-700773 | 3/1993 |
| KR | 94-10252 | 10/1994 |
| KR | 95-700043 | 1/1995 |
| KR | 95-702583 | 6/1995 |
| KR | 96-704602 | 8/1996 |
| KR | 2001-7012115 | 9/2001 |
| KR | 2003-7008997 | 10/2003 |
| NL | 0784674 | 12/2002 |
| NL | 0869167 | 1/2003 |
| NL | 1073339 | 2/2003 |
| NL | 0746608 | 11/2003 |
| PH | 31068 | 11/1984 |
| RU | 2140751 | 6/1997 |

| | | |
|---|---|---|
| RU | 2235775 | 11/1999 |
| RU | 2001117497 | 6/2001 |
| SE | 9802548 | 7/1998 |
| TR | 200101551 | 12/1999 |
| WO | 88/02775 | 4/1988 |
| WO | 88/03365 | 5/1988 |
| WO | 08/901969 | 3/1989 |
| WO | 89/06803 | 7/1989 |
| WO | 91/00920 | 1/1991 |
| WO | 91/06661 | 5/1991 |
| WO | 91/14772 | 10/1991 |
| WO | WO 91/17243 | 11/1991 |
| WO | 92/05249 | 4/1992 |
| WO | 92/14830 | 9/1992 |
| WO | 92/18645 | 10/1992 |
| WO | 93/01285 | 1/1993 |
| WO | 93/11249 | 6/1993 |
| WO | 93/12812 | 7/1993 |
| WO | 94/01541 | 1/1994 |
| WO | 94/04035 | 3/1994 |
| WO | WO 94/04035 | 3/1994 |
| WO | 94/14940 | 7/1994 |
| WO | 94/14951 | 7/1994 |
| WO | 94/26883 | 11/1994 |
| WO | 95/06720 | 3/1995 |
| WO | 95/09909 | 4/1995 |
| WO | 95/22606 | 8/1995 |
| WO | 95/22615 | 8/1995 |
| WO | 95/22625 | 8/1995 |
| WO | 95/29996 | 11/1995 |
| WO | 95/30744 | 11/1995 |
| WO | 96/09772 | 4/1996 |
| WO | 96/13578 | 5/1996 |
| WO | 96/13579 | 5/1996 |
| WO | 96/13580 | 5/1996 |
| WO | 96/27002 | 9/1996 |
| WO | 96/28542 | 9/1996 |
| WO | 96/30502 | 10/1996 |
| WO | 96/32472 | 10/1996 |
| WO | 96/39851 | 12/1996 |
| WO | 97/04079 | 2/1997 |
| WO | 97/05219 | 2/1997 |
| WO | 97/07202 | 2/1997 |
| WO | 97/11083 | 3/1997 |
| WO | 97/14713 | 4/1997 |
| WO | 97/27237 | 7/1997 |
| WO | 97/27276 | 7/1997 |
| WO | 97/41212 | 11/1997 |
| WO | 97/41735 | 11/1997 |
| WO | 97/41736 | 11/1997 |
| WO | WO 98/00029 | 1/1998 |
| WO | 98/08939 | 3/1998 |
| WO | 98/14594 | 4/1998 |
| WO | WO 98/13479 | 4/1998 |
| WO | WO 98/16112 | 4/1998 |
| WO | 98/18912 | 5/1998 |
| WO | 98/26057 | 6/1998 |
| WO | WO 98/23162 | 6/1998 |
| WO | 98/31790 | 7/1998 |
| WO | WO 98/31790 | 7/1998 |
| WO | 98/41623 | 9/1998 |
| WO | 98/44804 | 10/1998 |
| WO | 98/45453 | 10/1998 |
| WO | WO 98/45453 | 10/1998 |
| WO | 98/50532 | 11/1998 |
| WO | 98/51163 | 11/1998 |
| WO | 98/59028 | 12/1998 |
| WO | 99/33964 | 7/1999 |
| WO | 99/34011 | 7/1999 |
| WO | 99/37782 | 7/1999 |
| WO | 99/42566 | 8/1999 |
| WO | 99/50399 | 10/1999 |
| WO | 99/53001 | 10/1999 |
| WO | 99/53769 | 10/1999 |
| WO | 99/55883 | 11/1999 |
| WO | 00/05396 | 2/2000 |
| WO | 00/28044 | 5/2000 |
| WO | 00/32758 | 6/2000 |
| WO | 00/34450 | 6/2000 |
| WO | 00/36114 | 6/2000 |
| WO | WO 00/32758 | 6/2000 |
| WO | 00/43036 | 7/2000 |
| WO | 00/49164 | 8/2000 |
| WO | 00/58517 | 10/2000 |
| WO | 00/59307 | 10/2000 |
| WO | 00/60063 | 10/2000 |
| WO | 00/61771 | 10/2000 |
| WO | 00/71808 | 11/2000 |
| WO | 00/75295 | 12/2000 |
| WO | 01/16308 | 3/2001 |
| WO | 01/27251 | 4/2001 |
| WO | 01/29222 | 4/2001 |
| WO | WO 00/23461 | 4/2001 |
| WO | 01/34835 | 5/2001 |
| WO | WO 01/39544 | 5/2001 |
| WO | 01/39602 | 6/2001 |
| WO | 01/42433 | 6/2001 |
| WO | WO 01/39602 | 6/2001 |
| WO | 01/47363 | 7/2001 |
| WO | 01/66711 | 9/2001 |
| WO | 01/78524 | 10/2001 |
| WO | WO 01/75083 | 10/2001 |
| WO | 01/83559 | 11/2001 |
| WO | 01/83770 | 11/2001 |
| WO | 01/92502 | 12/2001 |
| WO | 02/00852 | 1/2002 |
| WO | 02/03805 | 1/2002 |
| WO | 02/06457 | 1/2002 |
| WO | WO 02/00852 A2 | 1/2002 |
| WO | WO 02/03805 A1 | 1/2002 |
| WO | WO 02/06508 | 1/2002 |
| WO | 02/24881 | 3/2002 |
| WO | 02/30207 | 4/2002 |
| WO | WO 02/39828 | 5/2002 |
| WO | 02/055679 | 7/2002 |
| WO | 02/062973 | 8/2002 |
| WO | 02/065854 | 8/2002 |
| WO | 02/066622 | 8/2002 |
| WO | WO 02/065854 A2 | 8/2002 |
| WO | WO 02/066622 A2 | 8/2002 |
| WO | 02/094123 | 11/2002 |
| WO | 2003/020923 | 3/2003 |
| WO | WO 03/020923 | 3/2003 |
| WO | WO 03/020941 | 3/2003 |
| WO | WO 2006/031699 | 3/2003 |
| WO | 03/040091 | 5/2003 |
| WO | 03/060112 | 7/2003 |
| WO | 03/070013 | 8/2003 |
| WO | 03/089620 | 10/2003 |
| WO | 03/097825 | 11/2003 |
| WO | WO 03/097835 | 11/2003 |
| WO | 03/099016 | 12/2003 |
| WO | 03/102118 | 12/2003 |
| WO | 2003100044 | 12/2003 |
| WO | WO 03/100044 | 12/2003 |
| WO | 04/004467 | 1/2004 |
| WO | 2004004467 | 1/2004 |
| WO | 2004/018660 | 3/2004 |
| WO | 04/053152 | 6/2004 |
| WO | 2004/053039 | 6/2004 |
| WO | 2004/053152 | 6/2004 |
| WO | 2004/059075 | 7/2004 |
| WO | WO 2004/064537 | 8/2004 |
| WO | WO 2004/084638 | 10/2004 |
| WO | 04/097012 | 11/2004 |
| WO | 2004/111216 | 12/2004 |
| WO | 2005/003339 | 1/2005 |
| WO | 2005/005977 | 1/2005 |
| WO | 97/07205 | 2/2005 |
| WO | 2005/066347 | 7/2005 |
| WO | 2005/066351 | 7/2005 |
| WO | 05069762 | 8/2005 |
| WO | 2005/080540 | 9/2005 |
| WO | 2005/087918 | 9/2005 |
| WO | WO 2005/111203 | 11/2005 |
| WO | 2006/008508 | 1/2006 |
| WO | 2006/008653 | 1/2006 |
| WO | 06018205 | 2/2006 |

| | | |
|---|---|---|
| WO | 2006/032279 | 3/2006 |
| WO | WO 2006/045354 | 5/2006 |
| WO | 2005/056782 | 6/2006 |
| WO | WO 2006/066590 | 6/2006 |
| WO | WO 2008/003420 | 1/2008 |
| WO | WO 2008/036863 | 3/2008 |
| WO | WO 2008/090395 | 7/2008 |
| WO | WO 2008/094847 | 8/2008 |
| WO | WO 2009/002480 | 12/2008 |
| WO | WO 2009/024736 | 2/2009 |
| WO | WO 2009/024862 | 2/2009 |
| WO | WO 2009/081094 | 7/2009 |

OTHER PUBLICATIONS

Arskog and Joergensen, "Baking performance of prior art lipases from *Candida cylindracea* and *Aspergillus foeditus* and their activity on galactolipids in dough", Novozymes Report Jul. 18, 2005.
Arskog and Joergensen, "Baking performance of prior art lipases from *Humicola Lanuginosa, Aspergillus tubigensis, Rhizopus delemar* and *Rhizomucor miehei*, and their activity on galactolipids in dough", Novozymes Report Jul. 17, 2005.
Aust K., "Applications of lecithin in bakery foods," AIB Research Technical Bulletin, vol. XV, issue 12, Dec. 1993, p. 1-6.
Banas A. et al., "Cellular sterol ester synthesis in plants is performed by an enzyme (Phospholipid: Sterol Acyltransferase) different from the yeast and mammalian Acyl-CoA: Sterol AcylTransferase", Journal of Biological Chemistry, 2005, vol. 280, No. 41, p. 34626-34634.
Beggs J.D., Transformation of yeast by a replicating hybrid plasmid, Nature (London), 1978, vol. 275, p. 104.
Bessette, "Efficient folding or proteins with multiple disulphide bonds in the *Escherida coli cytoplasm*", Proc. Natl. Acad. Sci. USA, 1999, vol. 96, p. 13703-13708.
Bo Yang et al., "Optimization of Enzymatic Degumming Process for Rapseed Oil," JAOCS, 2006, vol. 83, No. 7, p. 653-658.
Briand et al, "Substrate Specificity of the Lipase from *Candida parapsilosis*", Lipids, Aug. 1995, vol. 30, No. 8, p. 747-754.
Bru R., López-Nicolás J.M., García-Carmona F., (1995) "Aggregation of polyunsaturated fatty acid in the presence of cyclodextrins", Colloids and Surfaces A: Physiochemical and Engineering Aspects. 97, p. 263-269.
Brunel et al, "High-Level expression of *Candida parapsilosis* lipase/acyltransferase in *Pichia pastoris*," J Biotechnology, Jul. 1, vol. 111, No. 1, p. 41-50, 2004.
Buchold H. et. al., "Enzymatische Phosphatidentfernung aus Pflanzenolen" Technologies, 1993, vol. 95, No. 8, p. 300-304, ISSN:0931-5985.
Buckley J. Thomas et al., Substrate specificity of bacterial glycerophospholipid: Cholesterol Acyltransferase, Biochemistry, 1982, vol. 21, p. 6699-6703.
Bylund G. (ed), 1995, Dairy Processing Handbook, Chapter 2, p. 17-42, Lund, Sweden.
Bylund G. (ed), 1995, Dairy Processing Handbook, Chapter 9, p. 227-246, Lund, Sweden.
Ceci L.N. et al, Oil recovery and lecithin production using water degumming sludge of crude soybean oils, Journal of the Science of Food and Agriculture, 2008, vol. 88, No. 14, p. 2460-2466.
Cereghino et al., Heterologous protein expression in the methylotrophic yeast *Pichia pastoris*, FEMS Microbiology Review, 2000, vol. 24, No. 1, p. 45-66.
Chica et al, "Semi-rational approaches to engineering enzyme activity: combining the benefits of directed evolution and rational design" Current Opinion in Biotechnology, 2005, vol. 16, p. 378-384.
Christou P., Genetic engineering of crop legumes and cereals: current status and recent advances, Agro-Food-Industry Hi-Tech, Mar./Apr. 1994, p. 17-27.
Davis R.H. and de Serres, Genetic and Microbiological Research Techniques for *Neurospora crassa*, Methods Enzymology, 1971, vol. 17A, p. 79-143.
EC 1.1.3.10 (downloaded—Jul. 12, 2010).
EC 1.1.3.4 (downloaded—Jul. 12, 2010).
EC 1.1.3.5 (downloaded—Nov. 16, 2009).
EC 2.3.1.43.
EC 2.4.1.19 (Downloaded Jul. 12, 2010).
EC 3.1.1.26 (downloaded—Dec. 18, 2008).
EC 3.1.1.3 (downloaded—Dec. 18, 2008).
EC 3.1.1.32 (downloaded—May 22, 2008).
EC 3.1.1.4 Phospholipase A2 enzyme Enzyme Entry 1983 (downloaded Apr. 21, 2009).
EC 3.1.1.5.
EC 3.2.1.3 (downloaded Jul. 12, 2010).
EC 3.2.1.32 (Downloaded Jul. 12, 2010).
EC 3.2.1.60 (downloaded Apr. 28, 2009).
Eliasson A-C. and Larssen K., "Cereals in Breadmaking: a molecular colloidal approach," Marcel Dekker Inc, 1993, ISBN0824788168, p. 31-45.
Garzillo et al, "Production, Purification, and Characterization of Glucose Oxidase from Penicillium Variable P16," Biotechnol. Appl. Biochem., 1995, vol. 22, p. 169-178.
Genbank accession code NC_003888.1:8327480..8328367.
Genbank accession No. AL646052.
Genbank accession No. AL939131.1:265480..266367.
Genbank accession No CAC42140.
Genbank accession No. NC_003888.1:8327480..8328367.
Genbank accession No. NP_631558.
Genbank accession No. P41734.
Genbank accession No. Z75034.
Hammond E.G. et al., "Soybean Oil" in Bailey's Industrial Oil and Fat Products, Sixth edition, John Wiley, 2005, vol. 3, chapter 13, p. 577-653. ISBN 978047138401.
Hinchcliffe E., Kenny E., "Yeast as a vehicle for the expression of heterologous genes", Yeasts, 1993, vol. 5, Anthony H. Rose and J. Stuart Harrison, eds. 2nd edition, Academic Press Ltd.
Hinnen A. et al., Transformation of yeast, Proceedings of the National Academy of Sciences of the USA, 1978, vol. 75, p. 1929.
Hollenberg C.P. et al., Production of recombinant proteins by methylotrophic yeasts, Current Opinion in Biotechnology Oct, vol. 8, No. 5, p. 554-560 (1997).
Horwell DC, "The 'peptoid' approach to the design of non-peptide, small molecular agonists and antogonists of neuropeptides", Trends Biotechnol., 1995, vol. 13, No. 4, p. 132-134.
Hossen, Monjur, "Enzyme catalyzed synthesis of structured phospholipids with conjugated linoleic acid and plant sterols," A Dissertation by MD Monjur Hossen, May 2005, p. 1-152.
HUI, Bailey's Industrial Oil and Fat Products, 5th edition vol. 2 Edible Oil and Fat Products: Oils and Oilseeds, Wiley Interscience11995 ISBN 0471594261 p. 513-516.
International Dairy Federation Bulletin Document 116, 1979, p. 5, "Definition of recombined milk".
Ito H. et al., "Transformation of Intact Yeast Cells Treated with Alkali Cations," J. Bacteriology, 1983, vol. 153, p. 163-168.
Jost R., Milk and Dairy Products, 2007, Wiley-VCH, pp. 1-62.
Kalscheuer et al, "Synthesis of Novel Lipids in *Saccharomyces cerevisiae* by Heterologous Expression of an Unspecific Bacterial Acyltransferase," Applied and Environmental Microbiology, vol. 70, No. 12, p. 7119-7125, 2004.
Kane, "Effects of rare codon clusters on high-level expression of heterolgous proteins in *E. coli*" Current Opinion Biotechnology, 1995, vol. 6, p. 494-500.
Kimmel, A. et al. "Preparation of cDNA and the Generation of cDNA Libraries: Overview," Methods in Enzymology, 1987, vol. 152, p. 307-316.
LaVallie T.M., 2-Methoxyestradiol Inhibits Proliferation and Induces Apoptosis Independently of Estrogen Receptors $\alpha$ and $\beta$, Current Opinion in Biotechnology, 1995, vol. 6, No. 5, p. 501-506.
Leon et al., "A new approach to study starchy changes occurring the double-baking process and during bread storage," Z. Lebensn. Unters Forsch A, 1997, vol. 204 p. 316-320.
McIntyre et al., "Distribution of Glycerophospholipid-Cholesterol Acyltransferase in Selected Bacterial Species," Journal of Bacteriology , Jul. 1979, vol. 139, No. p. 132-136.
NCBI protein accession code AAK84028.1 GI:15082088.
NCBI protein accession code CAB39707.1 GI:4529178.
NCBI protein accession code CAB62724.1 GI:6562793.
NCBI protein accession code CAB88833.1 GI:7635996.
NCBI protein accession code CAB89450.1; GI:7672261.
NCBI protein accession code CAC01477.1 GI:9716139.
NCBI's Genbank database accession No. 1IVN_A; GID:33357066.

Nerland A.H., "Glycerophospholipid-cholesterol acyltransferase precursor", SwissProt, Feb. 11, 2005 XP002318368.
Oil Mill Gazetteer, "Enzymatic Degumming Improves Oil Refining in China," Jul. 2005 vol. 111, p. 2-4.
Phospholipase C, E.C. 3.1.4.3.
Poldermans B and Schoppink P, "Controlling the baking process and product quality with enzymes", Cereal Foods World, Mar. 1999, 44 (3), p. 132-135.
Potrykus I., Gene Transfer to Plants: assessment of published approaches and results, Annu. Rev. Plant Physiol. Plant Mol. Biol., 1991, vol. 42, p. 205-225.
PreSens Manual HydroPlate® HP96U and HydroPlate® HP96C.
Seffernick et al, "Melamine Deaminase and Atrazine Chlorohydrolase: 98 Percent Identical but Functionally Different", Journal of Bacteriology, Apr. 2001, vol. 183, No. 8, p. 2405-2410.
Seino et al, "Enzymatic Synthesis of Carbohydrate Esters of Fatty Acid (10 Esterification of Sucrose, Glucose, Frutose and Sorbitol", J. Am. Oil Chem. Soc., Nov. 1984, vol. 61, No. 11, p. 1761-1765.
Sequence alignment of database accession No. Q44268 (database: UNIProtKB/TrEMBL) with SEQ. ID No. 16.
Sequence alignment of database accession No. Q44268 (database: UNIProtKB/TrEMBL) with SEQ. ID No. 70.
Simon RJ et al.,"Peptoids: a modular approach to drug discovery", Proc. Natl. Acad. Sci. USA, 1992, vol. 89, No. 20, p. 9367-9371.
Stryer, "Conformation and Dynamics," Biochemistry, 2nd Edition, 1981, WH Freeman & Co., San Francisco, p. 16.
Sutrisno, A. et al, "Expression of a gene Encoding Chitinase (pCA 8 ORF) from *Aeromonas* sp. No. 10S-24 in *Esxherichia* coli and Enzyme Characterization," Journal of Bioscience and Bioengineering, vol. 91, No. 6, p. 599-602, 2001.
Szuhaj B.F., "Lecithins" in Bailey's Industrial Oil and Fat Products, Sixth edition, John Wiley, 2005, vol. 2, chapter 13, p. 361-456. ISBN 978047138401.
Tanji M.et al., "Lipase hydrolysis of milk fat and its soft fractions", Research Bulletin of Obihiro University, 2001, vol. 22, No. 2, p. 89-94.
Tiden E.B. and Hudson C.S., Preparation and Properties of the Amylases Produced by *Bacillus Macerans* and *Bacillus Polymyxa*, J. Bacteriology, 1942, vol. 43, p. 527-544.
Torres C.F. et al., A two steps enzymatic procedure to obtain sterol esters, tocopherols and fatty acid ethyl esters from soybean oil deodorizer distillate, Process Biochemistry, 2007, vol. 42, No. 9, p. 1335-1341.
Trueman L.J., "Heterologous Expression in Yeast," Methods Molecular Biology, vol. 49, p. 341-354 (1995).
Turner G. Vectors for generic manipulation, in Martinelli S.D, Kinghorn J.R. (editors), *Aspergillus*: 50 years on. Progress in industrial microbiology, 1994, vol. 29, p. 641-666.
Verenium Corporation leaflet Purifine® Enzyme"Convert Gums to Oils Significantly Increase Oil Yields no increase in Free Fatty Acids", San Diego, Jan. 2008.
Witkowski et al, "Conversion of a B-Ketoacyl Synthase to a Malonyl Decarboxylase by Replacement of the Active-Site Cysteine with Glutamine," Biochemistry, Sep. 7, 1999, vol. 38, No. 36, p. 11643-11650.
U.S. Appl. No. 60/039,791, filed Mar. 4, 1997, Clausen.
U.S. Appl. No. 60/189,780, filed Mar. 16, 2000, Soe.
U.S. Appl. No. 60/489,441, filed Jul. 23, 2003, Kreji.
Acker, L. "Die Lipide des Getreides, ihre Zusammense und inre Bedeutung", Getreide Mehl Brot (1974) 28:181-187.
Adamzcak, Marek, et al., "Application of Enzymatic Glycerolysis for Production of Monoglycerides from Waste Fats", Polish Journal of Food and Nutrition Science, Mar. 1994, p. 129-133.
Adhikari, B., et al., "Stickiness in Foods: A Review of Mechanisms and Test Methods", International Journal of Food Properties, vol. 4, No. 1, 2001, 1pg.
Agarwal et al., "Lipase Activity of Some Fungi Isolated from Groundnut", Current Science, Dec. 5, 1984, vol. 53, No. 23, p. 1253.
Aires-Barros M.R. et al., Isolation and purification of lipases, in "Lipases their structure, biochemistry and application", editors Woolley et al., Cambridge University Press, 1994, ISBN 0521445469 NZAS-00354436 p. 242-270.
Aisaka, Kazuo et al., "Production of Lipoprotein Lipase and Lipase by *Rhizopus japonicu*", Agri. Biol. Chem., vol. 43, No. 10, pp. 2125-2129, 1979.
Akoh, Casimir C., et al., "GDSL family of serine esterases/lipases" Progress in Lipid Research, vol. 43, 2004, pp. 534-552.
Allan Svendsen et al., "Biochemical properties of cloned lipases from the Pseudomonas family", Biochimica et Biophysica Acta, vol. 1259, 1995, pp. 9-17.
Al-Obaidy, K A, "Dough and Gluten Characteristics of Good and Poor Quality Flours: Lipid-Protein Bindings affected by Mixing time, water absorption, chemicals and heat," Dissertation Abstracts International B (1987) vol. 47(9) 3597, order No. DA8624641, pp. 266.
Amano Enzyme Inc., http://www.amano-enzyme.co.jp/english/productuse/oil_fat.html. Date of visit: Jun. 21, 2004; (Copyright 2003) pp. 1-2.
Amano Enzymes "Enzymes for Gastrointestinal Digestion" Oct. 1997, pp. 1-2.
Amano Enzymes, Amano Enzyme Europe Ltd, Sep. 1994, pp. 1-4.
Amin, Neelam S., et al., "Direct transformation of site-saturation libraries in *Bacillus subtilis*", BioTechniques, Dec. 2003, vol. 35 p. 1134-1140.
Amino acid composition of lipases, Alignment of of *F. oxysporium f.sp. lini* and *F. oxysporum* (DSM 2672) lipase amino acid sequences, D59. (Date Unknown).
Andersson, L., et al., "Hydrolysis of galactolipids by human pancreatic lipolytic enzymes and duidenal contents", Journal of Lipid Research, 1995, vol. 36, pp. 1392-1400.
Sander, Andreas, et al., "Herstellung und Anwendungsmoelichkeiten von Eiweiss-Fettsaeurekondensaten/Production and application of acylated proten hydrolysates", Fett/Lipid 99 (1997) Nr. 4, pp. 115-120.
An-I Yeh et al., "Effects of Oxido-reductants on rheological properties of wheat flour dough and comparison with some characteristics of extruded noodles", Cereal Chemistry, 1999, vol. 76, No. 5, pp. 614- 620.
Application of Fusarium oxysporum phospholipase (FoL) in baking, Trial performed at Novozymes A/S, D34 (Date Unknown).
Arbige, Michael A et al, "Novel lipase for cheddar cheese flavor development" Food Technology, vol. 40, 1996, p. 91-98.
Archer, David B., et al., "Proteolytic degradation of heterologous proteins expressed in *Aspergillus Niger*", Biotechnology Letter, vol. 14, No. 5, May 1992, pp. 357-362.
Arcos J.A. et al, "Quantative Enzymatic Production of 6.O-Acylglucose Esters", Biotechnology and Bioengineering 1998 vol. 57, No. 5, p. 505-509.
Arpigny Jean Louis et al, "Bacterial lipolytic enzymes: Classification and properties", Biochemical Journal, vol. 343, No. 1, Oct. 1, 1999, pp. 177-183, XP002375631.
Assignment Document for Enzymatisk detergent additiv, detergent og vaskemetode, executed Aug. 13, 1986 p. 1-3.
Atomi H, et al., "Microbial lipases—from screening to design", In: Barnes PJ, ed. Oils-Fats-Lipids, 21st World Congress Int Soc Fat Res. England: Bridgwater, 1995: pp. 49-50, vol. 1. NZAS-0016055-NZAS-0016056.
August C.A.P.A. et al. "The use of genetic engineering to obtain efficient production of porcine pancreatic phospholipase A2", Biochimica et Biophysica Acta, vol. 1089, 1991, pp. 345-351.
Aunstrup, Knud et al., "Production of Microbiol Enzymes", Microbiol Technology, Academic Press, 1979, 2nd edition, vol. 1, chap. 9, p. 281-309.
Ausubel, Frederick M., et al. (editors), "Short Protocols in Molecular Biology—A Compendium of Methods from Current Protocols in Molecular Biology", 1995, John Wiley & Sons, Inc, NZAS-0028441-NZAS-002844.
Bachmatova, I., et al., "Lipase of Pseudomonas mendocina 3121-1 and its Substrate Specificty", Biologija, 1995, p. 57-59.
"Fat Splitting, Esterification, and Interesterification", in Bailey's Industrial Oils and Fat Products, vol. 2, 4th Edition, John Wiley and Sons, New York pp. 97-173, 1982.
Bakezyme PH 800 Product Data Sheet, DSM Bakery ingredients, pp. 1-2. NZAS-0299424-NZAS-0299425. (Date After Mar. 19, 2002).

Balashev, K., "Surface studies of enzymes using Atomic force microscopy (AFM)" Chemistry Department, University of Michigan, Ann Arbor, MI, pp. 1-5, NZAS-0439472-NZAS-0439476. (Date Unknown).
Balcao V.M et. al., "Bioreactors with immobilized lipase: State of the art," Enzyme Microb Technhol, May 1, 1996; 18(6):392-416.
Balcao, V. et. al. "Lipase Catalyzed Modification of Milkfat," (1998), Biotechnology Advances, vol. 16, No. 2, pp. 309-341.
Ballance, D.J., et al., "Transformation of *Aspergillus Nidulans* by the orotidine-5'-phosphate decarboxylase gene of neurospora crassa", Biochemical and biophysical Research Communications, vol. 112, No. 1, 1983, pp. 284-289.
Ballance, "Transformation Systems for Filamentous Fungi and an Overview of Fungal Gene Structure", Molecular Industrial Mycology, Systems and Applications for Filamentous Fungi, Leong and Berka (eds.), Marcel Dekker Inc, New York 1991, pp. 1-29.
Barbesgaard, Peder et al, "On the safety of *Aspergillus oryzae*: a review," Applied Microbiology and Biotechnology (1992) 36: 569-572.
Barnes, P.J., "Lipids in Cereal Technology", Food and Science Technology, Academic Press, 1983, pp. 167-171.
Basrl, M., et al., "Amidination of Lipase with Hyrdophobic Imidoesters", JAOCS, vol. 69, No. 6, Jun. 1992, pp. 579-582.
Bateman A et. al., "HMM-based databases in InterPro," Briefings in Bioinformatics vol. 3, No. 3, pp. 236-245 (2002).
Bateman A et al, (2002), "The Pfam Protein Families Database," Nucleic Acids Res. vol. 30, No. 1, p. 276-280.
Becker T. "Separation and Purification Processes for Recovery of Industrial Enzymes" in R.K. Singh, S.S.H. Rizvi (eds): Bioseparation processes in Foods, Marcel Dekker, New York (1995) pp. 427-445.
Bedre Brod med nyt enzyme, Et nyt enzymkompleks reed hexose oxidase giver besparelser i produktionen og bedre brod, pp. 1-2, NZAS-0488041-NZAS-0488042 (Date Unknown).
Bekkers et al, "The use of genetic engineering to obtain efficient production of porcine pancreatic phospholipase A2 by Saccharomyces cerevisiae," (1991) Biochim Biophys Acta vol. 1089 No. 3, p. 345-51.
Bengtsson Olivecrona Gunilla et al. "Phospholipase activity of milk lipoprotein lipase," Methods in Enzymology, vol. 197, 1991 pp. 345-356.
Bentley S D et al, Complete genome sequence of the model actinomycete Streptomyces coelicolor A3(2), Nature vol. 417, 2002, pp. 141-147.
Berger K.G. (1990) "Recent developments in palm oil." Oleagineux, vol. 45, pp. 437-443.
Berks, Ben C., "A common export pathway for proteins binding complex redox cofactors?" Molecular Microbiology, 1996, vol. 22, pp. 393-404.
Beucage S.L. et al, (1981), "Deoxynucleoside Phosphoramidites—A New class of Key Intermediates for Deoxypolynucleotide Synthesis," Tetrahedron Letters 22, p. 1859-1869.
Bieleski R.L., Sugar Alcohols, in Loewus F A & Tanner W (eds), Plant Carbohydrates I. Intercellular Carbohydrates Encyclopedia Plant Physiol. N. S., 1982, 13A, chapter 5, p. 158-192, Springer, Berlin.
Bilyk, Alexander, et al., "Lipase-catalyzed triglyceride Hydrolysis in Organic Solvent", pp. 320-323, J, vol. 68, No. 5, May 1991.
Biocatalysts, Limited, Product Sheet for Lipomod(TM) 627P - L627P, published Jan. 9, 2002, Pontypridd UK, p. 1.
Jakobsen, Soren, "Biotekkomet falder hardt til jorden", Borsens, p. 6, Aug. 28, 2002. NZAS-0564031.
Birch et al., "Evidence of Multiple Extracellular Phospholipase Activities of *Aspergillus fumigatus*", Infection and Immunity, Mar. 1996, vol. 64, No. 3, 1996.
Birgitte Hugh-Jensen et al., "*Rhizomucor miehei* Triglyceride Lipase is Processed and Secreted from Transformed *Aspergillus oryzae*", Lipids, vol. 24, No. 9, 1989.
Biswas, et al., "Interfacial Behavior of Wheat Puroindolines: Study of Adsorption at the Air-Water Interface from Surface Tension Measurement Using Wilhelmy Plate Method", Journal of Colloid and Interface Science, vol. 244, pp. 245-253, 2001.
Bjorkling, F., et al., "Lipase Catalyzed Organic Synthesis", S. Servie (ed.), Microbial Reagents in Organic Synthesis, pp. 249-260, 1992.
Bjorkling, Frederik, et al., "Lipase Catalyzed Synthesis of Perozycarboxylic Acids and Lipase Mediated Oxidations", Tetrahedron, vol. 48, No. 22, pp. 4587-4592, 1992.
Bjorkling, Frederik, et al., "Lipase-mediated Formation of Peroxycarboxylic acids used in Catalytic Epoxidation of Alkenes", J. Chem. Soc., Chemical Communications, Issue 19, 1990.
Bjurlin et al. Identification of carboxylesterase activities of commercial triacylglycerol hydrolase (lipase) preparations, Eur. J. Lipid Sci. Technol. 104 (2002) 143-155.
Blain Ja et al, The Nature of Mycelial Lipolytic enzymes in filamentous fungi, Fems Microbiol. Lett., 1978, vol. 3, 85-87.
Blecker et al, Improved emulsifying and foaming of whey proteins after enzymic fat hydrolysis, (1997) J Food Science, vol. 62, No. 1.
Blumenthal, Cynthia Z., "Production of toxic metabolites in *Aspergillus niger, Aspergillus oryzae, and Trichoderma reesei*: justification of mycotoxin testing in food grade enzyme preparations derived from the three fungi", Regulatory Toxicology and Pharmacology, vol. 39, 2004, p. 214-228.
Boel, Esper, et al.; "*Rhizomucor miehei* Triglyceride Lipase is Synthesized as a Precursor"; Novo Research Institute; vol. 23; No. 7; Jul. 1988.
Bornscheuer U T et al, "Optimizing lipases and related enzymes for efficient application," Trends in Biotechnology, Elsevier Publications, Cambridge GB, vol. 20, No. 10, Oct. 1, 2002, pp. 433-437.
Bornscheuer, Uwe T., "Lipase-catalyzed syntheses of monoacylglycerols", Enzyme and Microbiol Technology, vol. 17, pp. 578-586, 1995.
Brady, Leo, et al., "A serine protease triad forms the catalytic centre of a triacylglycerol lipase", Nature, vol. 343, 1990, p. 767-770.
Brockerhoff, Hans, et al., "Lipolytic Enzymes", Academic Press, 1974, 1 page.
Brumlik, Michael J., et al., "Identification of the Catalytic Triad of the Lipase/Acyltransferase from *Aeromonas hydrophila*", Journal of Bacteriology, Apr. 1996, vol. 178, No. 7, pp. 2060-2064.
Brzozowski, A.M., et al., "A model for interfacial activation in lipases from the structure of a fungal lipase-inhibitor comples", Nature, vol. 351, 1991, pp. 491-494.
Buckley J. Thomas et al, "Purification and Partial Characterization of a Bacterial Phospholipid: Cholesterol Acyltransferase," Journal of Biological Chemistry, vol. 257, No. 6, pp. 3320-3325, 1982.
Buckley, "Mechanism of action of a bacterial glycerophospholipid cholesterol acyltransferase," Biochemistry 1983, 22, 5490-5493.
Bulkacz J et al, "Phospholipase a activity in supernatants from cultures of *Bacteroides melaninogenicus*," Biochim. Biophys. Acta (1981) vol. 664, pp. 148-155.
Van Den Berg. G, Regulatory status and use of lipase in various countries, Bulletin of the IDF 294/1994—The use of lipases in cheesemaking, pp. 19-20, (1994).
Burdge, Graham C., et al., "A method for separation of phosphatidylcholine, triacylglycerol, non-esterified fatty acids and cholesterol esters from plasma by solid-phase extraction", British Journal of Nutrition, 2000, vol. 84, pp. 281-787.
Butcher, Bronwyn G., et al., "The divergent chromosomal ars operon of Acidithiobacillus ferrooxidans is regulated by an atypical ArsR protein," Microbiology, 2002, vol. 148, pp. 3983-3992.
Buxton et al, "Transformation of *Aspergillus niger* using the argB gene of *Aspergillus nidulans*," Gene, 1985, 37:207-214.
Cao, Shu-Gui, et al., "Enzymatic Preparation of Monoglycerides via Glycerolysis of Fats and Oils Catalyzed by Lipase from *Pseudomonas* Species" National Laboratory of Enzyme Engineering. Monoglycerides, Enzyme Engine, Annals New York Academy of Sciences, 1996, vol. 799, issue 1, p. 670-677.
Carriere et al, "Pancreatic Lipase Structure—Function Relationships by Domain Exchange", American Chemical Society-Biochemistry (1997), 36, pp. 239-248.
Carriére, Frédéric , et al., "Structural basis for the substrate selectivity of pancreatic lipases and some related proteins", Biochemica et Biophysica Acta, vol. 1376, pp. 417-432, 1998.
Caruthers MH et al (1980) "New Chemical methods for Synthesizing polynucleotides," Nuc Acids Res Symp Ser 215-223.
Casimir C A et al "GDSL family of serine esterases/lipases," Progress in Lipid Research, 2004, pp. 534-552.

Castello, P., et al., "Technological and Biochemical effects of exogenous lipases in breadmaking", 2nd European Symposium on enzymes in Grain Processing, Dec. 8-10, 1999, Helsinki, p193-199. Published by VTT, Espoo, 2000.
Castello, Phillippe, et al., "Effect of exogenous lipase on dough lipids during mixing of wheat flours", Cereal Chemistry, 1998, vol. 75, No. 5, pp. 595-601.
Castello, Phillippe, et al., "Effects of mixing conditions and wheat flour dough composition on lipid hydrolysis and oxidation levels in the presence of exogenous lipase", Cereal Chemistry, 1999, vol. 76, No. 4. pp. 476-482.
Chakravarti DN et al, Biol. Abstracts, 1981, vol. 72, abstract No. 012592.
Cheng Cheng et al., "Transformation of Trichoderma viride using the *Neurospora crassa* pyr4 gene and its use in the expression of a Taka-amylase A gene from *Aspergillus oryzae*", Curr. Genet., 18: 453-456, 1990.
Christensen et al, "A new and simple method to immobilise lipases by means of granulation", 1998 Nachwachsende Rohstoff 10, 98-105.
Christie, William et al., "New Procedures for Rapid Screening of Leaf Lipid Components from Arabidopsis", Phytochemical Analysis, vol. 9, pp. 53-57, 1998.
Christophersen, Claus, et al., "Enzymatic Characterisation of Novamyl a Thermostable α-Amylase", Starch/Sturke, vol. 50, 1998, p. 39-45.
Chung O K et al, "Defatted and Reconstituted wheat flours. VI. Response to shortening addition and Lipid Removal in Flours that vary in Bread-making Quality" Cereal Chemistry (1980), vol. 57(2), p. 111-117.
Chung OK et al, "Recent Research on Wheat Lipids" Bakers Digest Oct. 1981.
Ciuffreda, Pierangela, et al., "Spectrophotometric Assay of Lipase Activity: A New 40nitrophenyl Ester of a Dialkylglycerol Suitable as a Chromogenic Substrate of Pseudomonas cepacia Lipase", Biocatalysis and Biotransformation, vol. 21, No. 3, pp. 123-127, 2003.
Claesson et al., "Techniques for measuring surface forces", Advances in Colloid and Interface Science, vol. 67, 1996, pp. 119-183.
Clausen, Kim, "Enzymatic oil-degumming by a novel microbial phospholipase", European Journal of Lipid Science And Technology, vol. 103, 2001, pp. 333-340.
Clausen, Kim, "New enzyme for degumming", Oils and Fats International, vol. 17, No. 4, Jun. 2001, pp. 24-25.
Cloning of rad51 and rad52 homologues from Aspergillus oryzae and the effect of their overexpression on homologous recombination, Novozymes internal document Feb. 9, 2001.
Collar C, et al, "Lipid binding fresh and stored formulated wheat breads. Relationships with dough and bread technological performance", Lab de Cereales Inst de Agroquimica y Tec de Alimentos, CSIC, Food Science and Technology International 2001, vol. 7(6), p. 501-510.
Colombo, Diego, et al., "Optically Pure 1-0- and 3-0-β-D-Glucosylk- and Galactosyl-sn-glycerols through Lipase-catalyzed Transformations", Tetrahedron Letters, vol. 36, No. 27, pp. 2865-4868, 1995.
Conference May 6-8, 1999 in Santorini, Greece—Lipases & Lipids Structure, Function and Biotechnological Applications—Slides presented by Charlotte Poulsen.
Cordle et al, "The hydrophobic surface of colipase influences lipase activity at an oil-water interface", Journal of Lipid Research, vol. 39 (1998), 1759-1767.
Coteron, A., et al., "Reactions of Olive Oil and Glycerol over Immobilized Lipases", JAOCS, vol. 75, No. 5, 1998, p. 657-660.
Council Directive of Dec. 21, 1988 (89/107/EEC).
Council Regulation (EC) No. 2991/94 May 12, 1994 Official Journal of the European Communities, Sep. 12, 1994, No. L316/2-7.
Courtin, Christophe M., et al., "Recent Advances in Enzymes in Grain Processing", Laboratory of Food Chemistry, Leuven, Belgium, 2003, p. 267-274, ISBN 90-9016671-8.
Creveld, Lucia D, et al., "Identification of Functional and Unfolding Motions of Cutinase as Obtained from Molecular Dynamics Computer Simulations", Proteins: Structure, Function, and Genetics, 33:253-264, 1998.
Cromie, Susan. Psychrotrophs and their Enzyme residues in cheese milk, The Australian Journal of Dairy Technology, vol. 47, Nov. 1992.
Cui et al., "Purification and characterization of an intracellular carboxylesterase from Arthrobacter viscosus NRRL B-1973", Enzyme and Microbial Technology, vol. 24, pp. 200-208, 1999.
Daboussi et al, "Heterologous expression of the Aspergillus nidulans regulatory gene nirA in Fusarium oxysporum," (1991) Gene vol. 109, No. 1, p. 155-60.
Daboussi et al., "Transformation of seven species of filamentous fungi using the nitrate reductase gene of Aspergillus nidulans", Curr. Genet., 15:453-456, 1989.
Daftary R.D. et al., Functional Bread-making Properties of Wheat Flour Lipids, Functional Bread-Making Properties of Lipids chapter 2, in Food Technology, Mar. 1968m vol. 22, No. 327, p. 79-82, NZAS-0487568.
Dahlquist, Anders, et al., "Phospholipid: diacylglycerol acyltransferase: An enzyme that catalyzes the acyl-CoA-independent formation of triacylglycerol in yeast and plants", PNAS, vol. 97, No. 12, pp. 6487-6492, 2000.
Dalrymple, Brian D., et al., "Three Neocallimastic patriciarum esterases associated with the degradation of complex polysaccharides are members of a new family of hydrolases", Microbiology, vol. 142, pp. 2605- 2614, 1997.
Danisco, "Unique Chance for Better Bread" *Direct, A Newsletter from Danisco Ingredients* (1996).
Danisco, Hexose oxidase—nyt enzym med mange mulingheder (advert) Mar. 15, 1999.
Darnell et al., Eds., "Synthetic Peptide and Nucleotide Sequences: Their Use in Isolating and Identifying Genes", in *Molecular Cell Biology*, Chapter 6, Manipulating Macromolecules, 1990, Scientific American Books, Baltimore.
Accession No. P10480 "Glycerophosphospholipid-cholesterol acyltransferase" created Jul. 1, 1989, available at www.ncbi.nlm.nih.gov/entrez.
Database accession No. Q44268—& Database UniProt 'Online! Nov. 1, 1996.
Database accession No. Q9F7Y6 Database UniProt 'Online!, Mar. 1, 2001.
Database FSTA International Food Information Service (IFIS), Frankfurt/Main, De Mine Y:"Application of the enzymatic methods to the determination of contaminated yolk in egg white." XP002077295 see abstract & Food Research International, vol. 29, No. 1, pp. 81-84 , 1976.
Database FSTA International Food Information Service (IFIS), Frankfurt/Main, De Nicolas J:"Action of oxidoreductases in breadmaking. Maturation of soft wheat flours and kneading of doughs." XP002077286 see abstract & Annales de Technologie Agricole, vol. 28, No. 4, 1979, pp. 445-468.
Database FSTA International Food Information Service (IFIS), Frankfurt/Main, De Qi Si J: "New enzymes for the baking industry" XP002077284 see abstract & Food Tech Europe vol. 3, No. 1, 1996, pp. 60-64, Novo Nordisk Ferment Ltd.
Database FSTA International Food Information Service (IFIS), Frankfurt/Main, De Weipert D:"Rheologie von Roggenteigen. II. Der einfluss der enzyme unterschiedlicher spezifitat auf das rheologische verhalten des teiges." XP002077285 see abstract & Getreide, Mehl Und Brot, vol. 26, No. 10, 1972, pp. 275-280.
Database Uniprotkb Jun. 1, 2003, S. Omura et al: "putative secreted hydrolase from streptomyces avermitilis" XP002376340 retirieved from EBI, Hinxton, UK Database accession No. Q828T4 abstract.
Database Uniprotkb May 1, 2000, S.D. Bentley et al: "Putative Secreted Hydrolase from Streptomyces coelicolor" XP002376339 retrieved from EBI, Hinxton, UK Database accession No. Q9S2A5 abstract.
Davies, Progress in Industrial Microbiology, Martinelli and Kinghorn (eds.), Elsevier, Amsterdam 1994, 29:525-560.
De Haas Gh et al, "Purification and Properties of Phospholipase A from Porcine Pancreas" Biochim. Biophys. ACTA, 1968, vol. 139, pp. 103-117.
Declaration by Clive Graham Phipps Walter (Dec C) Jul. 4, 2003.
Declaration by Dr Jorn Borch Soe (Dec F) Dec. 2, 2003.
Declaration by Dr Mark Turner (Dec G) Feb. 4, 2005, pp. 1-6.

Declaration by Henrik Pedersen (Dec A) Jul. 7, 2003, pp. 1-3.
Declaration by Henrik Pedersen, Masoud Rajabi Zargahi and Clive Graham Phipps Walter (Dec 2) Feb. 7, 2005, pp. 1-26, D46.
Declaration by Janne Brunstedt (Dec D) Jul. 4, 2003.
Declaration by Kazuko Kato, Henrik Pedersen, Masoud Rajabi Zaghari, Clive Phipps Walter, and Janne Brunstedt (Dec I) Feb. 7, 2005.
Declaration by Kim Borch Oct. 17, 2005.
Declaration by Luise Erlandsen Oct. 21, 2005.
Declaration by Masoud Rajabi Zargahi (Dec B) Jul. 7, 2003.
Declaration by Masoud Rajabi Zargahi (Dec E) Jul. 15, 2003.
Declaration by Tina Spendler Oct. 14, 2005.
Delcros, Jean-Francois, et al., "Effect of mixing conditions on the behavior of lipoxygenase, peroxidase, and catalase in wheat flour doughs", Cereal Chemistry, 1998, vol. 75, No. 1, pp. 85-93.
Dellaporta, et al.; "A Plant DNA Minipreparation Version II"; Plant Molecular Biology Reporter(1983); vol. 1(4); pp. 19-21.
Derewenda et al, "The crystal and molecular structure of the Rhizomuxor miehei Triacylglyceride Lipase at 1•9 Å Resolution", J. Mol. Biol. 1992, 227:818-839.
Derewenda, Urszula, et al., "Catalysis at the Interface: The Anatomy of a Conformational Change in a Triglyceride Lipase", Biochemistry, vol. 31, pp. 1532-1541, 1992.
Dictionary of Biochemistry and Molecular Biology, Stenesh, J. Second Edition, John Wiley, 1975, p. 16, ISBN 0471840890, p. 1-3.
Dinkci. N, Mucor miehei den elde edilen lipaz, Ege Univeraitesi Ziraat Fakultesi Dergisi Cilt, 37, Saiy 2-3, 2000, 141-148.
Direct, "The Road to Success: New Stabilizers Rouses Big Interest," A Newsletter from Danisco Ingredients, Sep. 1996, p. 1-4.
Directive 2000/36/EC. Http://europa.eu.int/scadplus/leg/en/lvb/121122b.htm. Dato: Jun. 16, 2004.
Drost-Lustenberger, C and Spendler T Lipopan F BG—Application and Mechanism of a new lipase for baking, Novozymes. Spanish version of EP869167, Novozymes, Oct. 7, 1998.
Drost-Lustenberger, C. et al., Novozymes, "Lipopan F BG—application and mechanism of a new lipase for bread baking" Cereal Food (2003), Novozymes internal draft.
Drost-Lustenberger, Cornelia, et al., "Lipopan F BG—unlocking the natural strengthening potential in dough", Cereal Food, 2004. Novozymes internal draft, p. 1-6.
Duan, Rui Dong, Fat Digestion and Absorption (2000), p. 25-46, publisher AOCS Press, Champaign III CODEN 69ACBA Conference; general review written in English.
Dubreil, Laurence, et al., "Localization of Puroinoline-a and Lipids in Bread Dough Using Confocal Scanning Laser Microscopy", J. Agric. Food Chem., 2002, vol. 50, pp. 6078-6085.
Ducancel, Frederic, et al., "Complete amino acid sequence of a PLA2 from the tiger snake Notechis sculatus scutatus as deduced from a complementary DNA", Nucleic Acids Research, vol. 16, No. 18, 1988.
Dugi Ka et al, "Human hepatic and lipoprotein lipase: the loop covering the catalytic site mediates lipase substrate specificity", Journal of Biological Chemistry (1995), vol. 270, pp. 25, 396-pp. 25, 401.
Dugruix, A. , et al., Preparation and Handling of Biological Macromolecules, Oxford University Press (1992) p. 31-39.
Dutilh & Groger, "Improvement of Product Attributes of Mayonnaise by Enzymic Hydrolysis of Egg Yolk with Phospholipase A2", 1981 J. Sci. Food Agric. 32, 451-458.
Dybdal, L., et al., "Enzymes in Cereals Processing", Novo Nordisk A/S, DK-2880, Denmark . NZAS-0254380, p. 1-11(Date Unknown).
Eddine et al, "Cloning and expression analysis of NhL1, a gene encoding an extracellular lipase from the fungal pea pathogen Nextria haematococca MP VI (Fusarium solani f. sp. pisi) that is expressed in planta", Mol. Genet. Genomics (2001) 265: 215-224.
EFEMA Index of Food Emulsifiers, Mono- and diglycerides of fatty acids, Jan. 2004, 4th Edition, p. 1-3 and 51-55.
Efthymiou CC et al., "Development of domestic feta cheese", Journal of Dairy Science 1964, vol. 47, No. 6, p. 593-598.
Eliasson et al., "Cereals in Breadmaking—A molecular colloidal approach", NZNA-0006056.
Ellaiah et al., "Production of lipase by immobilized cells of Aspergillus niger", Process Biochemistry, vol. 39, 2004, pp. 525-528.
Elyk, Alexander, et al., "Lipase-Catalyzed . . .", JAOCS, vol. 8, No. 5, May 1991, pp. 320-323.
Engelhorn and Raab, "Rapid Electroblotting of Small DNA Fragments from Polyacrylamide Gels", Biotechniques (1991) 11(5):594-6.
Engelhorn et al., "Rapid Electroblotting of Small DNA Fragments from Polyacrylamide Gels"; Biotechniques(1991); vol. 11(5); pp. 594-596.
Nagodawithana, T. "Enzymes in food processing" (3rd Ed.), Academic press 1993, p. 205-219.
EPO, Mobay Chemical Corporation—Decision of the Technical Board of Appeal 3.3.1 dated Jul. 1, 1982, *Official Journal EPO*, Oct. 1982, pp. 394-402.
Ettinger, William F. et al., "Structure of Cutinase Gene, cDNA, and the Derived Amino Acid Sequence from Phytopathogenic Fungi", Biochemistry, vol. 26, pp. 7883-7892, 1987.
Euromonitor International, "The World Market for Dairy Products—Introduction, Executive Summary, Operating Environment, World Market Overview, Key Trends and Developments" in *Euromonitor, Strategy 2000*, Feb. 2001.
European Parliament and Council Directive No. 95/2/EC of Feb. 20, 1995 on food additives other than colours and sweeteners. OJ No. L61 Mar. 18, 1995 p. 1-53.
European Parliament and Council Directive No. 98/72/EC of Oct. 15, 1998 amending Directive 95/2/EC on food additives other than colours and sweeteners. OJ No. L295 Nov. 4, 1998 p. 18-30.
European Journal of Biochemistry, vol. 166, 1987, Published by Springer International on behalf of the Federation of European Biochemical Societies.
Ezra, David, et al., "Coronamycins, peptide antibiotics produced by a verticillate Streptomyces sp. (MSU-2110) endophytic on Monstera sp.", Microbiology, 2004, vol. 150, p. 785-793.
Fauvel, et al.; "Purification of Two Lipases With High Phospholipase A, Activity from Guinea-Pig Pancreas"; Biochimica et Biophysica Acta(1981); vol. 663; pp. 446-456.
Fennema, Owen F., "Food Chemistry Second Edition, Revised and Expanded," Food Science and Technology, p. 371-475.
Fernandez-Garcia et al., "The use of lipolytic and proteolytic enzymees in the manufacture of manchego type cheese from ovine and bovine milk", 1994 J. Dairy Sci. 77: 2139-2149.
Fernandez-Lafuente, Roberto, et al., The coimmobilization of D-amino acid oxidase and catalase enables the quantitative transformation of D-amino acids (D-phenylalanine) into α-keto acids (phenylpyruvic acid), Enzyme and Microbial Technology, vol. 23, pp. 28-33, 1998.
Ferrer et al, 2000, "Purification and properties of a lipase from Penicillium chrysogenum isolated from industrial wastes," J. Chem. Technol. Biotechnol. 75, 569-576.
Finizym Technical Information, Novo Enzymes, 1981.
Fødevarenubusteriet (2003). Bekendtgørelse om indhold af transfedtsyrer I olier og fedtstoffer. Bekendtgørelse nr. 160 af Nov. 3, 2003.
Food Enzymes: Stalingase L, Gist-brocades Food Ingredients, p. 1-2 (Date after 2000).
Vafiades D, "Embracing Enzymes", Food R&D, Dairy Fields ingredient technology section, Mar. 1996 p. 39-44.
Forman, Todd, "Enzymes Used in Bread Baking: An Application Update", Technical Bulletin, vol. XXVI, Issue Oct. 10, 2004.
Fox, et al.; "Isolation and some Properties of Extracellular Heat-Stable Lipases: from *Pseudomonas Fluorescens* Strain AFT 36"; Journal of Dairy Research (1988); vol. 50; pp. 77-89.
Frenken N. et al (1992) "cloning of the Pseudomonas glumae Lipase Gene and Determination of the Active Site Residues," Appl. Envir. Microbiol. 58 3787-3791.
Freshzyme™, Novozymes Product Sheet Baking/2000-11814, NZAS-0265916. Mar. 12, 2001, p. 1-3.
Frohman, et al.;"Rapid Production of Full-Length cDNAs from Rare transcripts: Amplification using a single gene-specific oligonucleotide primer"; Proc. Natl. Acad. Sci. USA (1988); vol. 85; pp. 8998-9002.
Frost & Sullivan leaflet for report #7954-88 U.S. Market for Enzymes for Food Applications, May 2001, NZAS-0413133.

Fugman, Douglas A et al "Lipoprotein Lipase and phospholipase A2—Catalyzed hydrolysis of phospholipid vesicles with an encapsulated fluorescent dye," Biochemica et Biophysica acia 795 (1984) 191-195.
Daftary, R. D. et. al "Functional Bread-Making Properties of Wheat Flour Lipids", Food Technology, vol. 22, p. 327-330.
Galliard T and Dennis S (1974) Phospholipase, Galactolipase, and Acyl Transferase Activities of a Lipolytic Enzyme from Potatoe, Phytochemistry vol. 13, pp. 1731-1735.
Galliard, "The Enzymic Breakdown of Lipids in Potato Tuber by Phospholipid- and Galactolipid- Acyl Hydrolase Activities and by Lipoxygenase", Phytochemistry, 1970, vol. 9, pp. 1725-1734.
Gan, Z. et al., "Rapid Communication- Antisera agains: Wheat Diacylgalactosylglycerol (MGDG) and Diacyldigalactosylglycerol (DGDG)", Journal of Cereal Science, vol. 18, pp. 207-210, 1993.
Ganghro AB & Dahot MU, Sci Int. (Lahore), 1992, vol. 4, pp. 169-172.
Gemel J et al., "Comparison of galactoplipase activity and free fatty acid levels in chloroplasts of chill-sensitve and chill-resistant plants", European Journal of Biochemistry, vol. 166, 1987, Published by Springer International on behalf of the Federation of European Biochemical Societies, p. 229-233.
Geus et al (1987) Nucleic Acids Research 15(9) p. 3743-3759.
Gilbert, E. Jane, et al., "Purification and properties of extracellular lipase from Pseudomonal aeruginosa EF2", Journal of General Microbiology, 1991, vol. 137, pp. 2223-2229.
Gillian, B., Turgeon et al., "Cochliobolus heterostrophus using the Aspergillus nidulans amdS gene", Mol Gen Genet, 201: 450-453, 1985.
Gist-brocades, Amylase P Information Sheet, (Date Unknown).
Godfrey, Tony, et al., "Industrial Enzymology Second Edition", Macmillan Press, 1996, ISBN 0333594649, Chapter 2.17, Olive and other Edible Oils, p. 299-300.
Goodey et al, "Expression and secretion of foreign polypeptides in Yeast," Yeast Biotechnology, Berry et al (eds.), Allen and Unwin, London 1987, pp. 401-429.
Graille J, "Possible applications of acyltransferases in Oleotechnology," Lipid Technology, vol. 5, No. 1, 1993, pp. 11-16.
GRAS Notification dated Apr. 11, 2001 by Novozymes for LecitaseR and LipopanTM F. Gregg L. et al., A lipases preparation produced by Aspergillus oryzae expressing the gene encoding a lipases from Fusarium oxyporum. Novo Nordisk A/S product Sheet for Lecitase Novo, Oct. 2000.
Greenough et al (1996) "Safety evaluation of a lipase expressed in Aspergillus oryzae," Food Chem Toxicology 34:161-166 and PubMed abstract in respect thereof.
Greenough R J et al, "Safety Evaluation of a Lipase Expressed in Aspergillus oryzae," Food and Chemical Toxicology, vol. 34(2), 1996, pp. 161-166.
Grindsted Products, Grindsted Bakery News, p. 1-3. (Date Unknown).
Grindsted, "Emulsifiers for the baking industry" p. 1-35. (Date Unknown).
Grindsted, "Grindamyl Fungal Alpha-Amylase", p. 1-13. (Date Unknown).
Haas and Berka, 1991, "cloning, expression and characterization of a cDNA encoding a lipase from Phizopus delemar," Gene, 109:107-113.
Haas, et al., "Enzymatic Phosphatidylcholine Hydrolysis in Organic Solvents: an Examination of Selected Commercially Available Lipases", JAOCS, vol. 71, No. 5, May 1994, pp. 483-490.
Haas, et al.; "Lipases of the Genera *Rhizopus* and *Rhizomucor*: Versatile Catalysts in Nature and the Laboratory"; Food Biotechnology Micro-organisims (1995); pp. 549-588.
Haggag H F et al. Egypt J Food Sci vol. 22, No. 1 pp. 99-107 (1994).
Marion D et al., "Lipids, Lipid-protein interactions and the quality of baked cereal products", chapter 6 in Hamer, Rob J., et al., "Interaction: The Keys to Cereal Quality", American Association of Cereal Chemists, S Paul, Minnesota, 1998, ISBN 0913250996, p. 131-167.
Hanlin, Richard T., "Illustrated Genera of Ascomycetes"; The American Phytopathological Society, 1992, St Paul, Minnesota, p. 48, 49, 234, 235, 244, 245.
Hansen, Chr., Danisco and Novozymes, Apr. 3, 2002, Food Ingredients day, R&D—the main ingredients for growth.
Hara, et al.; "Comparative Study of Comercially Available Lipases in Hydrolysis Reaction of Phosphatidylcholine"; JAOCS (1997); vol. 74; No. 9, pp. 1129-1132.
Hawker, Kim L., et al., "Heterologous expression and regulation of the Neurospora crassa nit-4 pathway-specific regulartory gene for nitrate assimilation in Aspergillus nidulans", Gene., vol. 100, pp. 237-240, 1991.
Hedin, Eva M.K., et al., "Selective reduction and chemical modification of oxidized lipase cysteine mutants", Journal of Chemistry (2002) vol. 89, p. 529-539.
Helmsing, "Purification and Properties of Galactolipase", Biochim., Biophys., Acta, vol. 178, pp. 519-533, 1969.
Henderson, H.E., et al., "Structure-function relationships of lipoprotein lipase: mutation analysis and mutagenesis of the loop region", Journal of Lipid Research, vol. 34, 1993, pp. 1593-1602.
Henke, Erik, et al., "Activity of Lipases and Esterases towards Tertiary Alcohols: Insights into Structure-Function Relationships", Angew. Chem. Int. Ed., 2002, vol. 41, No. 17.
Hernquist L & Anjou K (1993) Diglycerides as a stabilizer of the β'-crystal form in margarines and fats, in Fette Seifen Anstrichmittel 2:64-66.
Hernquist L. Herslof B. Larsson K & Podlaha O. (1981) Polymorphism of rapeseed oil with low content of erucic acid and possibilities to stabilize the β'-crystal form in fats, in Journal of Science and Food Agriculture 32:1197-1202.
Hilton S et al, "Purification and spectral study of a microbial fatty acyltransferase:activation by limited proteolysis," Biochemistry vol. 29, No. 38, 1990, pp. 9072-9078.
Hilton S, Buckley JT, "Studies on the reaction mechanism of a microbial lipase/acyltransferase using chemical modification and site-directed mutagenesis," J Biol Chem. Jan. 15, 1991; 266(2): 997-1000.
Hirayama O et al, "Purification and properities of a lipid acylhydrolase from potatoe tubers," Biochim Biophys Acta. 1975, vol. 384(1), p. 127-137.
Hirose, Yoshihiko et al., "Characteristics of Immobilized Lipase PS on Chemically Modified Ceramics", Amano Pharmaceutical, p. 239 (Date Unknown).
Hjorth, Annegrethe, et al., "A Structural Domain (the lid) Found in Pancreatic Lipases is Absent in the Guinea Pic (Phospho) lipase", Biochemistry, vol. 32, pp. 4702-4704, 1993.
Hüfelmann et al, J. Food Sci., 1985, 50:1721-1731.
Holmquist et al., "Lipases from Rhizomucor miehei and Humicola lanuginosa: Modification of the Lid covering the active site alters enantioselectivity", Journal of Protein Chemistry, vol. 12, No. 6, 1993.
Holmquist et al., "Trp89 in the Lid of Humicola lanuginosa Lipase is Important for Efficient Hydrolysis of Tributyrin", Lipids, vol. 29, No. 9, 1994.
Horn T et al, Synthesis of oligonucleotides on cellulose. Part II: design and synthetic strategy to the synthesis of 22 oligodeoxynucleotides coding for Gastric Inhibitory Polypeptide (GIP), Nuc Acids Res Symp Ser No. 7, pp. 225-232 (1980).
Hoshino, et al.; "Calcium Ion Regulates the Release of Lipase of *Fusarium oxysporum*"; J. Biochem (1991); vol. 110; pp. 457-461.
Hoshino, Tamotsu, et al., "Purfication and Some Characteristics of Extracellular Lipase from Fusarium oxysporum", Biosci. Biotech. Biochem., vol. 56, No. 4, pp. 660-664, 1992.
Hossen, Monjur and Hernandez, Ernesto, "Phospolipase D-Catalyzed Synthesis of Novel Phospholipid-Phytosterol Conjugates", Lipids, vol. 39, Aug. 2004, pp. 777-782.
Hou, Ching T, "pH dependence and thermostability of lipases from cultures from the ARS Culture Collection", Journal of Industrial Microbiology, vol. 13, No. 4, 1994, pp. 242-248.
Hübner et al., "Interactions at the lipid-water interface", Chemistry and physics of Lipids, vol. 96, 1998, pp. 99-123.
Hugh-Jensen, Birgitte, et al., "Rhizomucor miehei Triglyceride Lipase is Processed and Secreted from Transformed Aspergillus oryzae", Lipids, vol. 24, No. 9, pp. 781-785, 1989.

Humum et al., "Enzyme Catalysed Synthesis in Ambient Temperature Ionic Liquids", Biocatalysis and Biotransformation, 2001, vol. 19, pp. 331-338, NZAS-0215170.
Icard-Verniere, Christele, et al., "Effects of mixing conditions on pasta dough development on biochemical changes", Cereal Chemistry, 1999, vol. 76, No. 4, pp. 558-565.
Igrejas, Gilberto, et al., "Genetic and Environmental Effects on Puroindoline-a and Puroindoline-b Content and their Relationship to Technological Properties in French Bread Wheats", Journal of Cereal Science, vol. 34, 2001, pp. 37-47.
Ikeda H et al, "Complete genome sequence and comparative analysis of the industrial microorganism *Streptomyces avermitilis*", Nature Biotech, vol. 21, pp. 526-531, May 2003.
Godfrey, Tony, et al., editors, Industrial enzymology (2nd Ed.), The Macmillan press, pp. 299-300, (1996).
Ishihara et al., "Studies on Lipase from *Mucor Javanicus* * I. Purification and Properties", Biochimica et Biophysica Acta vol. 388, pp. 413-422, (1975).
Isobe and Nokihara, "Primary structure determination of mono- and diacylglycerol lipase from *Penicillium camembertti*", Febs. Left., Federation of European Biochemical Societies, vol. 320, No. 2, pp. 101-106, (1993).
Isobe K et al, "A new enzymatic method for glycoaldehyde production from ethylene glycol", Journal of Molecular Catalysis B: Enzymatic 1 (1995), pp. 37-43.
Iwai and Tsujisaka, "Fungal lipase", (in Lipases, Borgström and Brockman (eds.), Elsevier, Amsterdam, 1984, pp. 443-468.
Iwai, Mieko, et al., "Hydrolytic and Esterifying Actions of Crystalline Lipase of Aspergillus Niger", J. Gen. Appl. Microbiol., 1964, vol. 10, No. 1, p. 13-21.
Izco et al., "Capillary electrophoresis: Evaluation of the effect of added enzymes on casein proteolysis during the ripening of a ewe's-milk cheese", Adv Food Sci, vol. 21, No. ¾, pp. 110-116, (1999).
Jacob, Jules S., et al., "The Effects of Galactolipid Depletion on the Structure of a Photosynthetic Membrane", The Journal of Cell Biology, vol. 103, Oct. 1986, pp. 1337-1347.
Jacobsberg B. & Oh C.H. (1976) Studies in Palm Oil Crystallisation, in Journal of the American Oil Chemist Society 53: pp. 609-616.
Jan-Willem F. A. Simons et al., "Cloning, purification and characterisation of the lipase from Staphylococcus epidermidis", Eur. J. Biochem., vol. 253, pp. 675-683, 1998.
Jeng-yen Lin, Matthew, "Wheat Polar Lipids—A Theseis Submitted to the Graduate Faculty of the North Dakota State University of Agriculture and Applied Science", May 1972, pp. 34-45.
Jensen B et al "Effect and Activity of Lipases in Dough and Bread" (translation), 48th Conference on Baking technology and 3rd Conference on Cake & Pastry Technology, Nov. 4-6, 1997, pp. 67-76.
Jensen, B., et al., "Effekt and Wirksamkeit von Lipasen in Teig and Brot" 48th Conference on Baking technology and 3rd Conference on Cake & Pastry Technology, Nov. 4-6, 1997, pp. 67-76.
Owens JJ, "Lecithinase Positive Bacteria in Milk", Process Biochemistry, Jan. 1978, vol. 13, pp. 13-14, 30.
Joerger et al., "Alteration of Chain Length Selectivity of a Rhizopus delemar Lipase through Site-Directed Mutagenesis", Lipids, vol. 29, No. 6, 1994, pp. 377-384.
Jong et al.; "American Type Culture Collection Catalogue of Filamentous Fungi"; Eighteenth edition (1991) p. 80.
List of Cultures, Fungi and Yeasts, 32 edition, Institute of the Royal Netherlands Academy of Arts and Sciences, p. 38. (1990).
JCM Catalogue of Strains, Fifth Edition, "Filamentous Fungi & Yeasts", p. 246, (1992).
List of Cultures, 1992 Microorganisms Ninth Edition, Institute for Fermentation, Osaka, Japan, p. 325, (1992).
Joshi, et al.; "Specificity of Fungal Lipase in Hydrolytic Cleavage of Oil"; Acta Microbiologica Hungarica (1987); vol. 34(2); pp. 111-114.
Joshi, Sunita, et al., "Specificity of Lipase isolated from Fusarium oxysporum", Department of Chemistry, Indian Institute of Technology, vol. 25, No. 1 & 2, pp. 76-78, (Jan.-Jun. 1985).
Juffer, A.H., et al., "Adsorption of Proteins onto Charged Surfaces: A Monte Carlo Approach with Explicit Ions", Journal of Computational Chemistry, vol. 17, No. 16, pp. 1783-1803, 1996.
Jurgens, Catharina, et al., "Directed evolution of a ($\beta\alpha$)8-barrel enzyme to catalyze related reactions in two different metabolic pathways", PNAS, Aug. 29, 2000, vol. 97, No. 18, pp. 9925-9930.
Kaniuga Z, "Galactolipase and chilling sensitivity of plants", Acta Biochim Pol. (1997), vol. 44(1), pp. 21-35.
Kapur J & Sood ML, J. "Effect of pH and Temperature on Lipase and Phospholipase of Adult *Haemonchus contortus* (Nematoda: Trichostrongylidae)" J. Parasit., 1986, vol. 72, No. 2, pp. 346-347.
Kasai, Naoya, et al., "Chiral C3 epoxides and halophydrins: Their preparation and synthetic application", Journal of Molecular Catalysis B: Enzymatic, vol. 4, 1998, pp. 237-252.
Kasai, Naoya, et al., "Optically Active Chlorohydrins as Chiral C3 and C4 Building Units: Microbial Resolution and Synthetic Applications", Chirality, vol. 10, pp. 682-692, (1998).
Kawamura, F., et al., "Construction of a *Bacillus subtilis* Double Mutant Deficient in Extracellular Alkaline and Neutral Proteases", J. of Bacteriology, vol. 160, No. 1, Oct. 1984, pp. 442-444.
Keller, R.C.A., et al., "Competitive Adsorption Behaviour of Wheat Flour Components and Emulsifiers at an Air-Water Interface", Journal of Cereal Science, vol. 25, 1997, pp. 175-183.
Keum J S et al., "Effect of Commercial Protease and Lipase on the Ripening of Cheddar Cheese", Korean J Dairy Sci 15 (2): pp. 103-117, (1993).
Kim, Hyung Kwoun, et al., Expression and characterization of Ca2+—independent lipase from Bacillus pumilus B26, Biochimica et Biophysica Acta, vol. 1583, 2002, pp. 205-212.
Kim, Myo-Jeong, et al., "Thermal Inactivation Kinetics and Application of Phospho and Galactolipid-Degrading Enzymes for Evaluation of Quality Changes in Frozen Vegetables", J. Agric. Food Chem., 2001, vol. 49, pp. 2241-2248.
Kimura, Yoshiharu, et al., "Application of Immobilized Lipase to Hydrolysis of Triacylglyceride", Eur J. Appl Microbiol Biotechnol, 1983, vol. 17, pp. 107-112.
Kindstedt et al., Rapid Quantative test for free oil (Oiling off) in melted Mozzarella cheese, J. Dairy Sci., 1990, vol. 73, pp. 867-873.
King et al, "The production of proteins and peptides from *Saccharomyces cervisiae*", Molecular and Cell Biology of Yeasts, Walton and Yarronton (eds.), Blackie, Glasgow, 1989, pp. 107-133.
Kirk, Ole, et al., "Fatty Acid Specificity in Lipase-Catalyzed Synthesis of Glucoside Esters" Biocatalysis, 1992, vol. 6, pp. 127-134.
Klein, Robert R., et al., "Altered Acyl Chain Length Specificity of Rhizopus delemar Lipase Through Mutagenesis and Molecular Modeling", Lipids, 1997, vol. 32, No. 2, pp. 123-130.
Klein, Robert R., et al., "Additive Effects of Acyl-Binding Site Mutations on the Fatty Acid Selectivity of Rhizopus delemar Lipase", JAOCS, vol. 74, No. 11, 1997, p. 1401-1407.
Kocak et al., Effect of lipase enzyme (palatase A 750 L) on the ripening of tulum cheese, Tr. J. of Agriculture and Forestry, 1995, vol. 19, p. 171-177.
Kocak et al., Effect of added fungal lipase on the ripening of Kasar cheese, Milchwissenschaft 51(1), 1996, p. 13-17.
Kochubei et al., Role of lipids in the organization of the closest surroundings of the reaction centers, Molekulyarnaya Biologiya vol. 12, No. 1, pp. 47-54, Jan.-Feb. 1978.
Kochubei S M et al, "Nature of Longwave Fluorescence of Particles Enriched with Photosytem I", Biophysics (1981), vol. 26(2), pp. 299-304.
Kochubei S M et al, "Differences in the Structure of Long Wave Fluorescence Molecular Aggregates in Photosytems I and II" Institute of Plant Physiology, Academy of Sciences of the Ukranian SSR, Kiev, (Translated from Molekulyarnaya Biologiya vol. 9, No. 2, pp. 190-193, Mar.-Apr. 1975) pp. 150-153, (1975).
Kochubei SM et al, "Role of Lipids in the Organization of the Closest Surroundings of the Reaction Centers of Photosytem 1", Institute of Plant Physiology, Academy of Sciences of the Ukranian SSR, Kiev, (Translated from Molekulyarnaya Biologiya vol. 12, No. 1, pp. 47-54, Jan.-Feb. 1978) pp. 32-37, (1978).
Kolkovski et al., "The Effect of Dietary Enzymes with Age on Protein and Lipid Assimilation and Deposition in *Sparus Aurata* Larvae", in Fish Nutrition in Practice, Biarritz (France), Jun. 24-27, 1991, Ed. INRA Paris, 1993, les Colloques, No. 61, p. 569-578.

Kostal, Jan, et al., "Enhanced Arsenic Accumulation in Engineered Bacterial Cells Expressing ArsR", Applied and Environmental Microbiology, Aug. 2004, vol. 70, No. 8, pp. 4582-4587.
Kouker, et al.; "Specific and Sensitive Plate Assay for Bacterial Lipases"; Applied and Environmental Microbiology (1987); vol. 53(1); pp. 211-213.
Krishna, Sajja Hari, et al., "Enantioselective transesterification of a tertiary alcohol by lipase A from Candida antarctica", Tetrahedron: Asymmetry, vol. 13, 2002, pp. 2693-2696.
Kristensen A.C.J., "Preparation of margarine and spreads by enzyme-generated emulsifiers", Master thesis, The Royal Veterinary and Agricultural University, Frederiksberg, Copenhagen, (Jan. 2004) pp. 1-154.
Krog, Niels J., "Dynamic and Unique Monoglycerides", Cereal Foods World, The American Association of Cereal Chemists, Jan. 1979, vol. 24, No. 1, p. 10.
Krupa, Zbigniew et al., "Requirement of Galactolipids for Photosystem J Activity In Lyophilized Spinach Chloroplasts", Biochimica et Biophysica Acta, 408, pp. 26-34, 1975.
KSV-5000—The Ultimate Langmuir/Langmuir-Blodgett System Brochure, KSW Instruments Ltd, Helsinki, Finland, pp. 1-14.
Kuipers, Oscar P., et al., "Enhanced Activity and Altered Specificity of Phospholipase A2 by Deletion of a Surface Loop", Science, vol. 244, 1989, p. 82-85 NZAS-0668767.
Kunze, Hans, et al., "On the mechanism of lysophospholipase activity of secretory phospholipase A2 (EC 3.1.1.4): deacylation of monoacylphosphoglycerides by intrinsic sn-1 specificity and Ph-dependent acyl migration in combination with sn-2 specificity", Biochimica et Biophysica Acta, vol. 1346, 1997, pp. 86-92.
Kuwabara, et al., "Purification and Some Properties of Water-soluble Phospholipase B from Torulaspora delbrueckii", J. Biochem., vol. 104, pp. 236-241, 1988.
Kuwabara, et al., "Purification and Some Properties of Water-soluble Phospholipase", Agric. Biol. Chem., vol. 52, No. 10, pp. 2451-2458, 1988.
Kweon et al., "Phospholipid Hydolysate and Antistaling Amylase Effects on Retrogradation of Starch in Bread", Journal of Food Science, vol. 59, No. 5, pp. 1072-1076, 1994.
Larchenkova LP et al. "Effect of starter and souring temperature on reproduction of *E coli* and lactobacili in milk," International Dairy Congress XXI, vol. 1, book 2. Moscow, Jul. 12-16, 1982, Brief Communications, p. 539.
Larsen N G et al, "The Effect of Ball-milling on Phospholipid Extractability and the Breadmaking Quality of Flour", Journal of Cereal Science (1990), vol. 12(2), p. 155-164.
Lecointe et al., "Ester Synthesis in Aqueous Media in the Presence of Various Lipases" Biotechnology Letters, vol. 18, No. 8 (August) pp. 869-874, (1996).
Lee, Keun Hyeung, et al., "Identification and characterization of the antimicrobial peptide corresponding to C-terminal B-sheet domain of tenecin 1, an antibacterial protein of larvae of Tenebrio molitor", Biochem. J., 1996, vol. 334, pp. 99-105.
Lee, Kyung S., et al., The Saccharomyces cerevisiae PLB1 Gene Encodes a Protein Required for Lysophospholipase and Phospholipase B Activity, The Journal of Biological Chemistry, vol. 269, No. 31, Issue of Aug. 5, pp. 19725-19730, NZAS-0418807.
Leggio, Leila Lo, et al., "The 1.62 A structure of Thermoascus aurantiacus endoglucanase: completing the structural picture of subfamilies in glycoside hydrolase family 5", FEBS Letters, vol. 523, 2002, pp. 103-108.
Leidich et al., "Cloning and Disruption of caPLB1, a Phospholipase B Gene Involved in the Pathogenicity of Candida albicans", The Journal of Biological Chemistry, vol. 273, No. 40, pp. 26078-26086, 1998.
Li, W., et al., "Surface properties and locations of gluten proteins and lipids revealed using confocal scanning laser microscopy in bread dough", Journal of Cereal Science, vol. 39, 2004, pp. 403-411.
Lih-ling Wang et al, "Inhibition of Listeria monocytogenes by monoacylglycerols synthesized from coconut oil and milkfat by lipase-catalyzed glycerolysis." Journal of Agricultural Food Chemistry (1993), vol. 41, No. 8, pp. 1000-1005.
Lima, Vera L.M., et al., "Lecithin-cholesterol acyltransferase (LCAT) as a plasma glycoprotein: an overview", Carbohydrate Polymers, vol. 55, 2004, pp. 179-191.
Lin M JY et al, "Effect on quality of bread and pasta products" Cereal Chemistry (1974), vol. 51(1), pp. 34-45.
Lin S et al, "Purification and characterization of a glycerol oxidase from *Penicillium* sp. TS-622" Enzyme and Microbial Technology 18 (1996), pp. 383-387.
"Lipase A Amano" Technical Bulletin No. Lez-1 (Product Specification from Armano Pharmaceutical Co Ltd Nagoya Japan), Dec. 16, 1985, pp. 1-6.
Lipase A "Amano" 6 Assay Note from Armano Pharmaceutical Co Ltd Nagoya Japan, Aug. 27, 1985, p. 1.
Lipase A "Amano" 6 product sheet, Amano Enzyme Inc, Apr. 1, 1999, pp. 1-2.
Lipase SP677 as a Baking Enzyme, from Novo Nordisk, Denmark, Mar. 17, 1994, pp. 1-5.
Lipomod L338P Data Sheet, Biocatalysts Limited, Aug. 15, 2003, pp. 1-2.
Lipopan F: Keep the quality—cut your costs 2000 Novozymes A/S. www.enzymes.novo.dk/cgl-bin/bvisapi.dll/biotimes/one_article.jsp?id=16947&lang=en&t=b1, pp. 1-2. (2000).
Litthauer, Derek, et al., "*Pseudomonas luteola* lipase: A new member of the 320—residue *Pseudomonas* lipase family", Enzyme and Microbial Technology, vol. 30, pp. 209-215, 2002.
Llustenberger, Cornelia, et al., "Application of Noopazyme in Asian Noodles and Non-Durum Pasta", Cereal Food, 2002-18584-01, p. 1, vol. 11.
Llustenberger, Cornelia, et al., "Enzymes in Frozen Dough and Parbaked Bread", Cereal Food, 2001-17056-01, p. 1, vol. 19.
Lo Y-C et al. Crystal structure of *Escherichia coli* Thioesterase I/ProteaseI/Lysophospholipase L1: Consensus sequence blocks constitute the catalytic center of SGNH-hydrolases through a conserved hydrogen bond network. Journal of Molecular Biology, London, GB, vol. 330, No. 3, 539-551.
Longhi, Sonia, et al., "Atomic Resolution (1.0 Å) Crystal Structure of Fusarium solani Cutinase: Stereochemical Analysis" J. Mol. Biol. vol. 268, pp. 779-799, 1997.
Lozano et al., "Over-stabilization of Candida antarctica lipase B by ionic liquids in ester synthesis", Biotechnology Letters, vol. 23, pp. 1529-1533, 2001.
Lustenberger, Cornelia et al., Abstract of "Application of lipase in Asian Noodles and Non-durum Pasta" AACC 2000 Annual Meeting, Nov. 5-9, 2000, pp. 1-2, available at http://aaccnet.org/meetings/2000/Abstracts/a00ma031.htm.
Luzi, Paola et al,, "Structure and organization of the human galactocerebrosidase (GALC) gene",Genomics (1995), vol. 26, No. 2, p. 407-409.
Madsen J.S. & Qvist K.B., "Hydrolysis of milk protein by *Bacillus licheniformis* protease specific for acidic amino acid residues" Journal of Food Science, vol. 62, pp. 579-582, (1997).
Mao, Cungui, et al., "Cloning and Characterization of a Saccharomyces cerevisiae Alkaline Ceramidase with Specificity for Dihydroceramide", The Journal of Biological Chemistry, vol. 275, No. 40, 2000, pp. 31369-31378.
Maria Teres Neves Petersen, PhD, "Total Internal Reflection Fluorescence Flow System with Electrochemical Control", TIRF-EC Flow System, University of Aalborg, pp. 1-13, Sep. 2002.
Marion D et al., "Lipids, Lipid-protein Interactions and the Quality of Baked Cereal Products" from Interactions The Keys to Cereal Quality, Chapter 6, Editors Hamer & Hoseney, American Association of Cereal Chemists, Inc., St. Paul, Minnesota, pp. 131-167, (1998). ISBN 0 913250-99-6.
Marion D et al., Wheat Lipids and Lipid-binding proteins: structure and function, in "Wheat Structure Biochemistry & Functionality", editor Schofield JP, 2000, Royal Society of Chemistry Special publication 212 pp. 245-260 ISBN 085404777-8 (It states that it is the Proceedings of Conference organised by Royal Soc of Chemistry Food Chemistry Group held on Apr. 10-12, 1995, in Reading, UK. However, it is unclear why there was such a delay).

Marsh, Derek, et al., "Derivatised lipids in membranes. Physicochemical aspexts of N-biotinyl phosphatidylethanolamines and N-acyl ethanolamines", Chemistry and Physics of Lipids, vol. 105, 2000, pp. 43-69.
Martinelle et al., "The Role of Glu87 and Trp89 in the lid of Humicola lanuginosa lipase", Protein Engineering, vol. 9, No. 6, 1996, pp. 519-524.
Martinez, Chrislaine, et al., "Engineering cysteine mutants to obtain crystallographic phases with a cutinase from Fusarium solani pisi", Protein Engineering, vol. 6, No. 2, pp. 157-165, 1993.
Martinez, Diego, et al., "Genome sequence of the lignocellulose degrading fungus Phanerochaete chrysosporium strain RP78", Nature Biotechnology, Nature Publishing Group, pp. 1-6, published online on May 2, 2004.
Mase et al., "Purification and Characterization of a new Lipase from Fusarium sp. TM-30", Biosci. Biotech. Biochem., vol. 59, No. 9, pp. 1771-1772, 1995.
Mason, "Use of Lipolytic Enzyme From *Aeromonas* in Detergents", Research Disclosure, Kenneth Mason Publications, Westbourne GB No. 390, Oct. 1996, pp. 661-662.
Masuda, Naoko, et al., "Primary structure of protein moiety of Penicillium notatum phospholipase B deduced from the Cdna", Eur. J. Biochem., vol. 202, pp. 783-787, 1991.
Matos, A.R., et al., "A patatin-like protein with galactolipase activity is induced by drought stress in Vigna unguiculata leaves", Biochemical Society Transactions, Lipid Catabolism: Lipid Degradation, vol. 28, part 6, p. 779-781, Jun. 30, 2000.
Matos, Ar et al, "A novel patatin-like gene stimulated by drought stress encodes a galactolipid acyl hydrolase", FEBS Letters, 491, pp. 188-192, (First published online Feb. 9, 2001).
Matsuda H et al, "Purification and properties of a lipolytic acylhydrolase from potato leaves", Biochimica et Biophysica Acta, vol. 573(1), p. 155-165, (1979).
Matsuoka, et al.; "Purification and properties of a Phospholipase C That has High Activity toward Sphingomyelin from *Aspergillus Saitoi*"; Biotechonology and Applied Biochemistry (1987); vol. 9, pp. 401-409.
Matthes et al, "Simultaneous rapid chemical synthesis of over one hundred oligonucleotides on a microscale" The EMBO Journal, vol. 3, No. 4, pp. 801-805, (1984).
Reetz M.T., Max-Planck-Institut fur Kohlenforschung et al., "Controlling the enantioselectivity of enzymes by directed evolution: Practical and theoretical ramifications", PNAS, Apr. 20, 2004, vol. 101, No. 16, pp. 5716-5722. NZAS-0441867.
McAuley, Katherine E., et al., "Structure of a feruloyl esterase from Aspergillus niger", Acta Crystallographica, Section D, D60, Biological Crystallography, pp. 878-887, 2004.
McCoy M G et al, "Characterization of the lipolytic activity of endothelial lipase", Journal of Lipid Research (2002), vol. 43, pp. 921-929.
McNeill G.P. & Berger R.G., Enzymatic glycerolysis of palm oil fractions and palm oil based model mixture: Relationship between fatty acid composition and monoglyceride yield, in Food Biotechnology 7: pp. 75-87, (1993).
McNeill, Gerald P., et al., "Further Improvements in the Yield of Monoglycerides During Enzymatic Glycerolysis of Fats and Oils", JAOCS, Jan. 1991, vol. 68, No. 1, pp. 6-10. NZAS-0213370.
McNeill, Gerald P., et al., "High-Yield Enzymatic Glycerolysis of Fats and Oils", JAOCS, vol. 68, No. 1, pp. 1-5, Jan. 1991.
McNeill, Gerald P., et al., "Selective Distribution of Saturated Fatty Acids into the Monoglyceride Fraction During Enzymatic Glycerolysis", JAOCS, vol. 69, No. 11, pp. 1098-1103, Nov. 1992.
McNeill, Gerald P., et al., "Solid Phase Enzymatic Glycerolysis of Beef Tallow Resulting in a High Yield of Monoglyceride", JAOCS, vol. 67, No. 11, pp. 779-783, (Nov. 1990).
Mechanism studies of the new lipase, Novozymes Article, No. 14, pp. 1-13. NZAS-0298034.
Memo: From Charlotte Johanson, "Short introduction/ status on Ferulic Acid Esterases and Acetyl Xylan Esterases", Protein Biochemistry, pp. 1-2, Jan. 9, 2004.
Meyer, V., et al., "Transcriptional regulation of the Antifungal Protein in Aspergillus giganteus", Mol Genet Genomics, 2002, vol. 266, pp. 747-757.
Meyers, Robert A., "Molecular Biology and Biotechnology—A Comprehensive Desk Reference" VCH Publishers, pp. 731-737, (1995). ISBN1560815698, NZAS-015769.
Michalski et al., "Photosynthetic apparatus in chilling-sensitive plants. VII. Comparison of the effect of galactolipase treatment of chloroplasts and cold-dark storage of leaves on photosynthetic electron flow", Biochimica et Biophysica Acta, vol. 589, pp. 84-99, 1980.
Mielgo, I., et al., "Covalent immobilisation of manganese peroxidases (MnP) from *Phanerochaete chrysosporium* and *Bjerkandera* sp. BOS55", Enzyme and Microbial Technology, vol. 32, pp. 769-775 (2003).
Miller, Byron S., et al., "A Comparison of Cereal, Fungal, and Bacterial Alpha-Amylases as Supplements for Breadmaking", Food Technology, pp. 38-42, (Jan. 1953). NZAS 0225991.
Mine Y, "Application of the enzymatic methods to the determination of contaminated yolk in egg white", Food Research International, vol. 29, No. 1, pp. 81-84, (1996).
Ministerio da Ciencia e Tecnologia, *Diario Oficial da Uniao*, No. 134, p. 6, Jul. 15, 2003. ISSN 1677-7042, NZNA-0046369.
Mogensen, Jesper E., et al., "Activation, Inhibition, and Destabilization of Thermomyces lanuginosus Lipase by Detergents", Biochemistry, vol. 44, pp. 1719-1730, 2005.
Mohsen et al., "Specificity of Lipase Produced by Rhyopus Delemar and Its Utilization in Bread Making", Egypt. J Food. Sci. vol. 14, No. 1, pp. 175-182.
Molecular Biological Methods for Bacillus—Chapter 3 Plasmids (Ed. C.R. Harwood and S.M. Cutting) John Wiley and Sons Ltd, Chichester, UK, p. 75-174, 1990.
Mølgaard, Anne, et al., "Rhamnogalacturonan acetylesterase elucidates the structure and function of a new family of hydrolases", Structure, vol. 9, No. 4, pp. 373-383, 2000. NZNA-0056695.
Umanskii M.S. et al., Effect on quality of Kostroma cheese of bacterial cultures selected on phospholipase activity, Molochnaya Promyshlennost 1980 No. 11 21-25, 47—abstract from Food Sci & Tech Abs.
Monick John A., Alcohols, Their Chemistry, Properties and Manufacture, Reinhold Book Cooperation, pp. 3, 6, 14, 47, 48, (1968).
"Mono- and Diglycerides of Edible Fatty Acids", in Monographs for Emulsifiers for Foods, 2nd Edition, The European Food Emulsifier Manufacturers' Association (EFEMA), pp. 47-51, Nov. 1985.
Moore, Charles M., et al., "Metal ion homeostasis in *Bacillus subtilis*", Current Opinion in Microbiology, vol. 8, pp. 188-195, 2005.
Morgan, Keith R., et al., "Stalling in Starch Breads: The Effect of Antistaling α-Amylase", Starch/Stärke, vol. 49, pp. 59-66,1997.
Morgan-Jones, Gareth; "Notes on Coelomycetes.II. Concerning the *Fusicoccum Anamorph* of *Botryosphaneria Ribis*"; Mycotoxon, vol. 30, pp. 117-125; Oct.-Dec. 1987.
Morinaga et al., "Improvement of Oligonucleotide-Directed Site-Specific Mutagenesis Using Double-Stranded Plasmid DNA", Biotechnology 2, pp. 636-639, (1984).
Morten, T. & A., Letter, Rodovre, Jul. 2004.
Mukherjee, Kumar D. et al., "Enrichment of y-linolenic acid from fungal oil by lipase-catalysed reactions", Appl. Microbiol Biotechnol (1991), vol. 35, pp. 579-584.
Murakami, Mototake, et al., "Transesterification of Oil by Fatty Acid-Modified Lipase", Technical Research Institute, JAOCS, Jun. 1993, vol. 70, No. 6, p. 571-574 NZAS-0457255.
Murakami, Nobutoshi, et al., "Enzymatic Transformation of Glyceroglycolipids into sn-1 and sn-2 Lysoglyceroglycolipids by use of Rhizopus arrhizus Lipase", Tetrahedron, vol. 50, No. 7, pp. 1993-2002, (1994).
Mustranta, Annikka, et al., "Comparison of Lipases and Phosphlipases in the Hydrolysis of Phospholipids", Process Biochemistry, vol. 30, No. 5, pp. 393-401, 1995.
General Conditions of the company limited by shares N.V. Nederlandsch Octrooibureau, Terms and Conditions, Jan. 2004. NZAS-0012567.
Nagano, et al.; "Cloning and Nucleotide Sequence of cDNA Encoding a Lipase from *Fusarium keteroporum*"; J. Biochem (1994); vol. 116; pp. 535-540.

Nagao T. et al, "C-Terminal Peptide of *Fusarium heterosporum* Lipase is Necessary for its Increasing Thermostability", J. Biochem., vol. 124, 1124-1129, 1998.
Nagao, T., et al, "Amino Acid Residues Contributing to Stabilization of *Fusarium heterosporum* Lipase", J. of Bioscience and Bioengineering, vol. 89, No. 5, pp. 446-450, 2000.
Nagao, T., et al, "Review: Increase in stability of *Fusarium heterosporum* lipase", J. of Molecular Catalysis B: Enzymatic 17 (2002) pp. 125-132.
Nagao, T., et al, "Use of Thermostable *Fusarium heterosporum* Lipase for Production of Structured Lipid Containing Oleic and Palmitic Acids in Organic Solvent-Free System", JAOCS vol. 78, No. 2, pp. 167-172, (2001).
Nagao, Toshihiro et al., "Cloning and Nucleotide Sequence of CDNA Encoding a Lipase from *Fusarium heterosporum*", J. Biochem., vol. 116, pp. 535-540, 1994.
Nagao, Toshihiro et al., "Expression of Lipase cDNA from *Fusarium heterosporum* by *Saccharomyces cereviisiae*: High-Level Production and Purification", Journal of Fermentation and Bioengineering, 1996, vol. 81, No. 6, pp. 488-492.
Godtfredsen S E, "Lipases", in "Enzymes in food processing" (3rd Ed.), Nagodawithana T and Red G (editors), Academic Press, New York, 1993, ISBN 0125136307, chapter 8, p. 205-219 NZAS-0665885.
National Research Council (U.S.) Committee on Specifications of the Food Chemicals Codex, "Lipase Activity" in *Food Chemicals Codex* (1981) National Academy Press, Washington, D.C. pp. 492-493.
Needleman & Wunsch (1970), J. of Molecular Biology 48, 443-453.
Nelson and Long, Analytical Biochemistry (1989), 180, p. 147-151.
Nerland A H, Journal of Fish Diseases, vol. 19, No. 2, 1996, pp. 145-150.
Néron, et al., "Effects of lipase and the phosphlipase on the lipids hydrolysis during mixing in correlation with the oxygen consumption by wheat flour dough during kneading", poster 125 Ko at AACC/Tia, San Diego, Calfornia, Sep. 20-22, 2004, available at http://www.cnam.fr/biochimie.
Ness, Jon. E., et al., "DNA shuffling of subgenomic sequences of subtilisin" Nature Biotechnology, vol. 17, Sep. 1999.
Nestle Research Center, Brochure for "Food Colloids 2006" in Montreux, Switzerland, Apr. 23-26, 2006.
Neugnot Virginie et al, European Journal of Biochemistry, 2002, vol. 269, pp. 1734-1745.
Newport, G., et al., "KEX2 Influences Candida albicans Proteinase Secretion and Hyphal Formation", The Journal of Biological Chemistry, 1997, vol. 272, No. 46, pp. 28954-28961.
Nicolas, Anne, et al., "Contribution of Cutinase Serine 42 Side Chain to the Stabilization of the Oxyanion Transition State", Biochemistry, vol. 35, pp. 398-410, 1996.
Nielsen et al., "Lipases A and B from the yeast Candida antarctica", in "Biotechnological Applications of Cold-Adapted Organisms" Margesin R & Shimmer F (editors), Springer, 1999, ISBN 3540649727 p. 49-61 NZAS-0214451.
Nierle W et al, Fette Seifen Anstrichmittel (Wheat Lipids: Function and Effect in Flour Processing) (1981), vol. 83(10), p. 391-395.
Nierle, Von W. et al. "Weizenlipide: Funktion and Einflub bei der Verarbeitung des Mehles".
Nierle, W., et al., "Versuche zur Verlangerung der Haltbarkeit von Dartoffelprodukten", Chem. Mikrobiol. Technol. Lebensm., 1975, vol. 3, pp. 172-175.
Nobutoshi M et al, Tetrahedron Letters (1991), vol. 31(1), p. 1331-4.
Novozymes data dated Jul. 17, 2005 entitled "Baking performance of prior art lipases from *Humicola lanuginosa, Aspergillus tubigensis, Rhizopus delemar* and *Rhizomucor miehei*, and their activity on galactolipids in dough".
Novozymes Memo—Test of lipases for EP1193314B1, Jul. 6, 2005, p. 1-5.
Novozymes Report 2002 Annual Report, "Successfor new baking enzyme," p. 1-2.
Novozymes journal BioTimes, "Biowhitening—a new concept for steamed bread", Jan. 2005 http://www.biotimes.com/en/Articles/2005/March/Pages/Biowhitening-anewconceptforstearnedbread.aspx, p. 1-2.
Novozymes, "Breakthrough: Less Fattening Fried Food" *BioTimes*, Jun. 2001, No. 2, p. 1-12.
Novozymes, "Enzymes for dough strengthening", 2001, p. 16-21.
Novozymes, "Lipopan F BG—application and mechanism of a new lipase for bread baking" (Draft) *Cereal Food* (2003) (Author: Drost-Lustenberger, C. et al.), p. 1-29.
Novozymes, Drost-Lustenberger, C., "Lipopan F BG: Application and Mechanism of a new Lipase for baking.", *Cereal Foods*, p. 1-9.
Novozymes article, "Mechanism studies of the new lipase,"Cereal Foods, No. 14, p. 1-9.
Novozymes, "Product Sheet for Lipopan F BG", *Cereal Food*, (2001), p. 1-3.
Novozymes, "Product Sheet for Lipopan FS BG", *Cereal Food* (2002), p. 1-3.
Novozymes, "Product Sheet for Lipopan S BG", *Cereal Food* (2002), p. 1-3.
Novozymes, "Product Sheet for Noopazyme", Cereal Food (2002) p. 1-3.
Novozymes, "Product Sheet for Novozym 27016," Baking (2000), p. 1-6.
Novozymes, "Product Sheet for Novozym 27019," Baking (2000), p. 1-6.
Novozymes, "Product Sheet for Novozym 27080," Cereal Food (2003), p. 1-3.
Novozymes, "Product Sheet for Novozym 27106" p. 1-2.
Novozymes, "Product Sheet: Enzyme Business, Noopazyme" p. 1-2.
Novozymes, "Product Sheet: Enzyme Business, Novozym 27019" p. 1-2.
Novozymes, "Product Sheet: Enzyme Business, Novozym 677 BG," p. 1-2.
Novozymes, "Revolutionizing baking", *BioTimes* (Dec. 2002) pp. 6-7.
Novozymes, "Strong sales for lipase that makes dough stronger" *BioTimes*, Dec. 2003, p. 1-2.
Novozymes, "The Novozyme Touch: Make your mark on the future," p. 1-3.
Novozymes, "The perfect roll every time for steers", *BioTimes*, Sep. 2003, p. 1-2.
Novozymes, "The value of innovation", *BioTimes*, Mar. 2004, p. 8-9.
Novozymes, "The vital role of technical service in baking", *BioTimes*, Jun. 2004, p. 8-9.
Novozymes, Lipopan 50 BG, Product Sheet, p. 1-3.
Novozymes, Lipopan 50 BG, Product Specification, p. 1-3.
Novozymes, Lipopan F BG, Product Data Sheet, p. 1-2.
Novozymes, Lipopan FS BG, Product Sheet, Cereal Food, p. 1-3.
Novozymes brochure "Enzymes at work" 2004, p. 1-60.
NY metode til aktivitetsbestemme fedtnedbrydende vaskemiddelenzy, p. 1.
Nylander et al., "Interaction between lipids and lipases A collection of papers presented at the European Meeting on lipid and lipase interaction at Lund University" Sep. 2000.
Ognjenovic Radomir et al, Acceleration of ripening of semi-hard cheese by proteolytic and lipolytic enzymes, Proceedings for Natural Sciences, 1996, vol. 91, p. 5-17.
Ohm, J.B., et al., "Relationships of Free Lipids with Quality Factors in Hard Winter Wheat Flours", Cereal Chem., vol. 79, No. 2, pp. 274-278, 2002.
Ohta, S. et al., "Application of Enzymatic Modification of Phospholipids on Breadmaking", Abstract from AACC 68th Annual Meeting in Kansas City, MO, Oct. 30th-Nov. 3, 1983, published in Cerial Foods World, p. 561.
Ohta, Yoshifumi, et al , "Inhibition and Inactivation of Lipase by Fat Peroxide in the Course of Batch and Continuous Glycerolyses of Fat by Lipase", Agric. Biol. Chem., vol. 53, No. 7, pp. 1885-1890, 1989.
Okiy D.A. (1977) "Partial glycerides and palm oil Crystallisation," in Journal of Science and Food Agriculture vol. 28, p. 955.
Okiy D.A. (1978) "Interaction of triglycerides and diglycerides of palm oil," in Oleagineux, vol. 33 p. 625-628.
Okiy D.A., Wright, W.B., Berger, K.G. & Morton I.D. (1978), The physical properties of modified palm oil, in Journal of Science of Food and Agriculture 29:1061-1068.

Oluwatosin, Yemisi E., et al., "Phenotype: a Possible Role for the Kex2 Endoprotease in Vacuolar Acidification", Molecular and Cellular Biology, 1998, pp. 1534-1543.
Oluwatosin, Yemisi E., et al., "Mutations in the Yeast KEX2 Gene Cause a Vma-Like Phenotype: a Possible Role for the Kex2 Endoprotease in Vacuolar Acidification", Molecular and Cellular Biology, vol. 18, No. 3, pp. 1534-1543, Mar. 1998.
O'Mahony et al. "Hydrolysis of the lipoprotein fractions of milk by Phospholipase C," Journal of Dairy Science, 1972, vol. 55, No. 4, p. 408-412.
Orberg, Marie-Louise, "Self-assembly Structures Formed by Wheat Polar Lipids and their Interaction with Lipases", Master of Scient Thesis, Apr. 2005.
Orskov, Janne, et al., "Solubilisation of poorly water-soluble drugs during in vitro lipolysis of medium- and long-chain triacylglycerols", European Journal of Pharmaceutical Sciences, vol. 23, 2004. pp. 287-296.
Osman, Mohamed, et al., "Lipolytic activity of Alternaria alternata and Fusarium oxysporum and certain properties of their lipids", Microbios Letters, vol. 39, pp. 131-135, 1988.
Ostrovskaya L K et al, "Spectral Features of the Action of Galactolipase on Native Forms of Chlorophyll," Dokl Akad Nauk SSSR, (vol. 186(4), p. 961-963) p. 59-61.
O'Sullivan et al, "A Galactolipase activity associated with the thylakoids of Wheat Leaves (*Triticum aestivum* L.)," J Plant Physiol, vol. 313, (1987) p. 393-404.
Outtrup, Günther H., et al., "Properties and Application of a Thermostable Maltogenic Amylase Produced by a Strain of *Bacillus* Modified by Recombinant-DNA Techniques", Starch/Starke (2003) vol. 36, No. 12, pp. 405-411.
Palomo, Jose M., et al., "Enzymatic production of (3S, 4R)-(−)-4-(4'-fluoropheny1)-6-oxo-piperidin-3-carboxylic acid using a commerical preparation of lipase A from Candida antarctica: the role of a contaminant esterase" Tetrahedron: Asymmetry, vol. 13, 2002, pp. 2653-2659.
Palomo, Jose M., et al., "Enzymatic resolution of (±)-glycidyl butyrate in aquenous media. Strong modulation of the properties of the lipase from Rhizopus oryzae via immobilization techniques", Tetrahedron: Asymmetry, vol. 15, 2004, pp. 1157-1161.
Palomo, Jose M., et al., "Modulation of the enantioselectivity of Candida antarctica B lipase via conformational engineering: kinetic resolution of (±)-α-hydroxy-phenylacetic acid derivatives", Tetrahedron: Asymmetry, vol. 13, 2002, pp. 1337-1345.
Pariza, Michael, et al., "Evaluating the safety of Microbiol Enzyme Preparations Used in Food Processing: Update for a New Century", Regulatory Toxicology and Pharmacology (2001) vol. 33, pp. 173-186.
Patent Abstracts of Japan vol. 016, No. 528 (C-1001), Oct. 29, 1992 & JP 04 200339 A see abstract.
Patent Abstracts of Japan vol. 095, No. 001, Feb. 28, 1995 & JP 06 296467 A see abstract.
Peelman F, et al, "A proposed architecture for lecithin cholesterol acyl transferase (LCAT): Identification of catalytic triad and molecular modeling," Protein Science Mar. 1998 7(3): 587-99.
Penninga et al, "Site-directed mutations in Tyrosine 195 of Cyclodextrin Glycosyltransferase from *Bacillus circulans* Strain 251 affect qctivity and product Specificity," Biochemistry (1995), 3368-3376.
Persson, Mattias, et al., "Enzymatic fatty acid exchange in digalactosyldiacylglycerol", Chemistry and Physics of Lipids, vol. 104, 2000, pp. 13-21.
Peters, G.H., et al., "Active Serine Involved in the Stabilization of the Active Site Loop in the Humicola lanuginosa Lipase", Biochemistry, 1998, vol. 37, pp. 12375-12383.
Peters, G.H., et al.; "Dynamics of *Rhizomucor miehei* lipase in a lipid or aqueous environment: Functional role of glycines"; Draft for Biophys. J, Nov. 1996 vol. 71, No. 5, p. 2245-2255 NZAS-0031441.
Peters, G.H., et al.; "Essential motions in lipases and their relationship to the biological function", Proceedings of the German Conference on Bioinformatics, GCB '96, Leipzig, Germany, Sep. 30 -Oct. 2, 1996, poster, p. 280-282 NZAS-0031438.
Peters, Günther H., et al., "Theoretical Investigation of the Dynamics of the Active Site Lid in *Rhizomucor miehei* Lipase", Biophysical Journal, vol. 71, 1996, pp. 119-129.
Philippine Patent Application Serial No. 31068.
*Harborne J.B. et al.* (*editors*), *Phytochemical Dictionary: A Handbook of Bioactive Compounds from Plants, Taylor & Francis, 1993, ISBN 978050667363 Chapter 4, "Sugar Alcohols and Cyclitols", p. 20-23.*
Picon et al., "Release of Encapsulated Proeinase from Dehydration-Rehydration Liposomes by a Co-encapsulated Phospholipase," Biotechnology Letters, Oct. 1995, vol. 17, No. 10, pp. 1051-1056.
Plijter J and JHGM Mutsaers, "The surface rheological properties of dough and the influence of lipase on it, Gist-brocades," Bakery Ingredients Division, Oct. 1994.
Plou et al, "Enzymatic acylation of di- and trisaccharides with fatty acids: choosing approiate enzyme, support and solvent," J. Biotechnology 92 (2002) 55-66.
Ponte J G, "Note on the Separation and Baking properties of Polar and Nonpolar Wheat Flour Lipids," Cereal Chemistry (1969), vol. 46(3), p. 325-329.
Poulsen, C.H., et al., "Effect and Functionality of Lipases in Dough and Bread", in Angelino SAGF, Hamer RJ, van Hartingsveldt W, Heidekamp F, van der Lugt JP (editors), First European Symposium on Enzymes and Grain Processing, Zeist, The Netherlands, TNO Nutrition and Food Research Institute, ISBN 90-75202-04-0, p. 204-214. Proceedings of ESEGP-1, Noordwijkerhout, The Netherlands, Dec. 2-4, 1996. NZAS-0158559.
Poulsen, Charlotte, et al. "Purification and Characterization of a Hexose Oxidase with Excellent Strenghening Effects in Bread" Cereal Chem. (1998) vol. 75(1); pp. 51-57.
Product Data Sheet, Bakezyme p. 500 BG, DSM Food Specialties, p. 1-2.
Product Description PD 40084-7a Grindamyl Exel 16 Bakery Enzyme, pp. 1-2.
Product Sheet B1324a-GB —"Lecitase® Novo", Novo Nordisk, Oct. 2000, pp. 1-4.
Product Sheet, Enzyme Business Lipozyme® 10.000 L, Novo Nordisk, p. 1-2.
Punt, P. et. al., "Transformation of Filamentous Fungi Based on Hygromycin B and Phleomycin Resistance Markers," Meth. Enzym., 1992, 216:447-457.
Pyler, E.J., "Baking Science and Technology," Third Edition vol. 1, 1988, p. 1-602.
Pyler, E.J., "Baking Science and Technology," Third Edition, vol. II, 1988, p. 1-784.
Queener et al. (1994), "Improved Expression of a Hybrid: Streptomyces clavuligerus cefE Gene in Penicillium chrysogenum," Ann N Y Acad Sci. 721, p. 178-193.
Rambosek, J., "Recombinant DNA in Filamentous Fungi: Progress and Prospects," CRC Crit. Rev. Biotechnol., 1987, vol. 6, No. 4, p. 357-393.
Rapp, Peter, et al., "Formation of extracellular lipases by filamentous fungi, yeasts, and bacteria", Enzyme Microb. Technol., 1992, vol. 14, November.
Rapp, Peter; "Production, regulation, and some properties of lipase activity from *Fusarium Oxysporum* f. sp. *vasinfectum*"; Enzyme and Microbial Technology(1995); vol. 17; pp. 832-838.
Reetz M.T et. al., "Overexpression, immobilization and biotechnological application of *Pseudomonas* lipases," Chem Phys Lipids. Jun. 1988; 93(1-2): 3-14.
Reetz Manfred T, "Lipases as practical biocatalysts," Current Opinion in Chemical Biology, Apr. 2002, vol. 6, No. 2, pp. 145-150.
Reiser J et al.(1990). "Transfer and Expression of Heterologous Genes in Yeasts other than *Saccharomyces cerevisiae*," Adv Biochem Eng Biotechnol. 43, p. 75-102.
Richardson & Hyslop, "Enzymes", pp. 371-476 in "Food Chemistry Second Edition, Revised and Expanded", 1985, second edition, Owen R. Fennema (ed), Marcel Dekker, Inc, New York and Basel.
Richardson and Hyslop, "Enzymes: XI—Enzymes Added to Foods During Processing" in *Food Chemistry*, Marcel Dekker, Inc., New York, NY 1985.

Arskog and Joergensen, "Baking performance of prior art lipases from *Candida cylindracea*and *Aspergillus foeditus* and their actiivty on galactolipids in dough", Novozymes Report 2005.
Arskog and Joergensen, "Baking performance of prior art lipases from *Humicola lanuginosa, Aspergillus tubigensis, Rhizopus delemar* and *Rhizomucor miehei*, and their actiivty on galactolipids in dough", Novozymes Report 2005.
Richardson, Toby H., et al., "A Novel, High Performance Enzyme for Starch Liquefaction", The Journal of Biological Chemistry, vol. 277, No. 29, Issue of Jul. 19, pp. 25501-26507, 2002.
Roberts et al. (1992) . "Heterologous gene expression in *Aspergillus niger*: a glucoamylase-porcine pancreatic prophospholipase A2 fusion protein is secreted and processed to yield mature enzyme," Gene 122(1), 155-161.
Roberts, et al.; "Extracellular Lipase Production by Fungi from Sunflower Seed"; Mycologia(1987); vol. 79(2); pp. 265-273.
Roberts, Ian N., et al., Heterologous gene expression in *Aspergillus niger*: a glucoamylase-porcine pancreatic prophospholipase A2 fusion protein is secreted and processed to yield mature enzyme.
Robertson et al, "Influence of Active Site and Tyrosine Modification on the Secretion and Activity of the *Aeromonas hydrophila* Lipase/Acyltransferase," Journal of Biological Chemistry, 1994, vol. 259, No. 3, p. 2146-2150.
Rodrigues, et al.;"Short Communication: Bioseparations with Permeable Particles"; Journal of Chromatography & Biomedical Applications(1995); vol. 655; pp. 233-240.
Rogalska, Ewa, et al., "Stereoselective Hydrolysis of Triglycerides by Animal and Microbial Lipases", Chirality, vol. 5, pp. 24-30, 1993.
Rose, et al.;"CODEHOP (Consensus-Degenerate Hybrid Oligonucleotide Primer) PCR primer design"; Nucleic Acids Research(2003); vol. 31(13); pp. 3763-3766.
Rousseau, Derick, et al., "Tailoring the Textural Attributes of Butter Fat/Canola Oil Blends via *Rhizopus arrhizus* Lipase-Catalyzed Interesterification. 2. Modifications of Physical Properties", J. Agric. Food Chem., vol. 1998, vol. 46, pp. 2375-2381.
Rydel, Timothy J. et al., "The Crystal Structure, Mutagenesis and Activity Studies Reveal that Patatin Is A Lipid Acyl Hydrolase with a Ser-Asp Catalytic Dyad", Biochemistry, 2003, vol. 42, pp. 6696-6708.
Sahsah, Y., et al., "Enzymatic degradation of polar lipids in Vigna unguiculata leaves and influence of drought stress", Physiologia Plantarum, vol. 104, pp. 577-586, 1998.
Sahsah, Y., et al., "Purification and characterization of a soluble lipolytic acylhydrolase from Cowpea (*vigna unguiculata* L.) leaves", Biochimica et Biophysica Acta, vol. 1215, pp. 66-73, 1994.
Saiki R.K. et al, "Primer-Directed Enzymatic Amplification of DNA with a Thermostable DNA Polymerase," Science (1988) 239, pp. 487-491.
Saito, Kunihiko, et al., "Phospholipase B from Penicillium notatum", Methods in Enzymology, 1991, vol. 197, p. 446-456 NZAS-0418833.
Sakai, Norio, et al., "Human glactocerebrosidase gene: promoter analysis of the 5'-flanking region and structural organization", Biochimica et Biophysica Acta, vol. 1395, pp. 62-67, 1998.
Sakaki T et al, Advanced Research on Plant Lipids, Proceedings of the International Symposium on Plant Lipids, 15th, Okazaki, Japan, May 12-17, 2002 (2003) p. 291-294, Publisher Kluwer Academic Publishers.
Sales Range for Baking Improver and Premix Manufacturers from DSM Bakery Ingredients, p. 1.
Sambrook et al, Chapters 1, 7, 9, 11, 12 and 13—Molecular Cloning a laboratory manual, vol. 3, p. 1.1-13.104, Cold Spring Harbor Laboratory Press (1989).
Sambrook, J., et al. "Molecular Cloning: A Laboratory Manual, Second Edition", Plasmid Vectors, 1989, p. 1-462.
Sanchez et al., "Solution and Interface Aggregation States of Crotalus atrox Venom Phospholipase A2 by Two-Photon Excitation Fluorescence Correlation Spectroscopy", Biochemistry, 2001, vol. 40, pp. 6903-6911.
Sarney Douglas B. et al, "Enzymatic Synthesis of Sorbitan Esters Using a Low-Boiling-Point Azeotrope as Reaction Solvent", Biotechnology and Bioengineering, 1997, vol. 54(4).
Saxena, et al.; "Purification Strategies for Microbial Lipases"; Journal of Microbilogical Methods (2003); pp. 1-18.
Scheib et al.; "Stereoselectivity of Mucorales lipases toward triradylglycerols—A simple solution to a complex problem"; Protein Science (1999); vol. 8; pp. 215-221.
Schiller, Jurgen, et al., "Lipid analysis of human spermatozoa and seminal plasma by MALDI-TOF mass spectrometry and NMR spectroscopy—effects of freezing and thawing" Chemistry and Physics of Lipids, vol. 106, 2000, pp. 145-156.
Schofield, J. David, "Wheat Structure, Biochemistry and Functionality", Department of Food Science and Technology, Apr. 2000, p. 243-260.
Scopes, Robert K., "Section 8.4: Ultrafiltration" in *Protein Purification Principles and Practice, Third Edition* (1994) Springer-Verlag, New York, p. 267-269.
Sequence alignment of the nucleotide sequences of SEQ ID No. 2 of EP'167 and SEQ ID No. 7 of D20 and the amino acid sequences of SEQ ID No. 2 of EP'167 and SEQ ID No. 8 of D20.
Shehata, A. "Manufacture of Blue Cheese by Direct Acidification Methods," University of Wisconsin, Nov. 30, 2005, p. 1-90.
Shillcock, Julian C., et al., "Equilibrium structure and lateral stress distribution of amphiphilic bilayers from dissipative particle dynamics simulations", Journal of Chemical Physics, vol. 117, No. 10, Sep. 8, 2002.
Shillcock, Julian C., et al., "Tension-induced fusion of bilayer membranes and vesicles", Advance Online Publication Feb. 13, 2005, Nat. Mater., 2005, vol. 4, No. 3, p. 225-228 NZAS-0231181.
Shimada et al, "Enzymatic Purification of Polyunsaturated Fatty Acids," J. Of Bioscience and Bioengineering vol. 91, No. 6, 529-538 (2001).
Shimada et al, "Purification and Characterization of a Novel Solvent-Tolerant Lipase from *Fusarium heterosporum*," J. of Fermentation and Bioengineering vol. 75, No. 5, 349-352 (1993).
Shimada et al, "Enrichment of Polyunsaturated Fatty Acids with *Geotrichum candidum* Lipase," JAOCS vol. 71, No. 9, (Sep. 1994), p. 951-954.
Shin, et al.; "Butyl-Toyopearl 650 as a New Hydrophobic Adsorbent for Water-Soluable Enzyme Proteins"; Analytical Biochemistry(1984); vol. 138; pp. 259-261.
Shogren, M.D., et al., "Functional (Breadmaking) and Biochemical Properties of Wheat Flour Components. I. Solubilizing Gluten and Flour Protein", Cereal Chemistry, vol. 46, No. 2, Mar. 1969, p. 93-103.
Si, Joan Qi, "Enzymes, Baking, Bread-Making", Encyclopedia of Bioprocess Technology, Wiley, 1999, ISBN 0471138223 NZAS-0255053, p. 1-18.
Si, Joan Qi, "Synergistic Effect of Enzymes for Breadbaking", Novo Nordisk publication A-06513b, p. 1-18, based on presentation No. 300 at AACC Annual Meeting 1996, Baltimore. Also Encyclopedia of Bioprocess Technology, Wiley, 1999, ISBN 0471138223.
Si, Joan Qi, et al. "Enzymes for bread, noodles and non-durum pasta", Cereal Food 2002 p. 1:3-3:4. Also in Enzymes in Food Technology, RJ Whitehurst & BA Law, Enzymes in Food Technology, Sheffield Academic Press, ISBN 1-84127-223-X, p. 19-54.
Si, Joan Qi, et al., "Novamyl—A true Anti-Staling Enzyme", Cereal Food, Oct. 2001, p. 1-20.
Si, Joan Qi, et al., "Synergistic Effect of Enzymes for Breadbaking", Cereal Food, Oct. 2001, p. 1:21, based on presentation No. 300 at AACC Annual Meeting 1996, Baltimore. Also Encyclopedia of Bioprocess Technology, Wiley, 1999, ISBN 0471138223.
Si, Joan Qi; "New Enzymes for the Baking Industry"; Food Tech Europe (1996) pp. 60-64.
Sias B et al, "Human Pancreatic Lipase-Related Protein 2 Is a Galactolipase," Biochemistry, (2004), vol. 43(31), p. 10138-48.
Siew W.L. et. al. (1999) "Influence of diglycerides on crystalisation of palm oil," in Journal of Science of Food and Agriculture 79:722-726.
Siew W.L. & Ng W.L. (2000) Differential scanning thermograms of palm oil triglycerides in the presence of diglycerides, in Journal of Oil Palm Research 12:107.

Siew W.L. (2001) Understanding the Interactions of Diacylglycerols with oil for better product performance, paper presented at the 2001 PIPOC International Palm Oil Congress—Chemistry and Technology Conference Aug. 20-23, 2001, Kuala Lumpur, Malaysia.
Skovgaard, et al.;"Comparison of Intra- and extracellualr isozyme banding patterns of *Fusarium Oxysporum*"; Mycol. Res. (1998); vol. 102(9); pp. 1077-1084.
Slotboom et al, "Hydrolysis of Phosphoglycerides by Purified Lipase Preparation," Chem. Phys. Lipids vol. 4 (1970) 15-29.
Smith, George P.; "The Progeny of sexual PCR"; Nature; vol. 370; No. 18; Aug. 4, 1994 p. 324-325.
Smith, Timothy L., et al., "The promoter of the glucoamylase-encoding gene of *Aspergillus niger* functions in Ustilago maydis", Gene. 88, 259-262, 1990.
Soe, J.B., "Analyses of *Monoglycerides* and Other *Emulsifiers* by Gaschromatography", Fette, Seifen, Anstrichmittel, 1983, 85 Jahrgang, nr. 2, p. 72-76NZNA-0005896.
Solares, Laura F., et al., "Enzymatic resolution of new carbonate intermediates for the synthesis of (S)-(+)-zopiclone", Tetrahedron: Asymmetry, vol. 13, 2002, pp. 2577-2582.
Sols and De Le Fuente, "On the substrate specificity of glucose oxidase", Biochem et Biophysica Acta (1957) 24:206-7.
Sonntag N.O.V. (1982a) Glycerolysis of Fats and methyl esters—status, review and critique, in Journal of American Oil Chemist Society 59:795-802A.
Soragni, Elisabetta, et al., "A nutrient-regulated, dual localization phospholipase A2 in the symbiotic fungus" The EMBO Journal, vol. 20, No. 18, pp. 5079-5090, 2001.
Sorensen, H.R., et al., "Effects of added enzymes on the physicochemical characteristics on fresh durum-pasta", Internal # A-6780 (Date unknown).
Sosland, Josh, "Alive and kicking", Milling & Baking News, Feb. 24, 2004. http://www.bakingbusiness.com/co_articles.asp?ArticleID=70026 downloaded Sep. 16, 2004 p. 1-13.
Soumanou, Mohamed M., et al., "Two-Step Enzymatic Reaction for the Synthesis of Pure Structured Triacylglycerides", JAOCS, vol. 75, No. 6, 1998.
Spargeon, Brad, "In China, a twist: Forgers file patents" 1 page.
Spendler, et al., "Functionality and mechanism of a new 2nd generation lipase for baking industry"—Abstract. 2001 AACC Annual Meeting; Symposia at Charlotte, NC. Oct. 14-18, 2001.
Spradling J.E., "Tailoring Enzyme Systems for Food Processing, in Biocatalysis in Agricultural Biotechnology", ACS Symposium Series 389, ed. Whitaker, John R. et al., 1989, ISBN 0-8412-1571-5 p. 24-43 NZAS-0213683.
Sreekrishna K et al (1988) "High level expression of heterologous proteins in methylotrophic yeast *Pichia pastoris*," J Basic Microbiol. 28(4), 265-78.
Stadler et al., "Understanding Lipase Action and Selectivity", CCACAA, vol. 68, No. 3, pp. 649-674, 1995.
Steinstraesser, et al., "Activity of Novispirin G10 against *Pseudomonas aeruginosa* In Vitro and in Infected Burns", Antimicrobial Agents and Chemotherapy, Jun. 2002, vol. 46, No. 6, pp. 1837-1844.
Stemmer, Willem P.C.; "DNA shuffling by random fragmentation and reassembly: In vitro recombination for molecular evolution"; Proc. Natl. Acad. Sci. USA, vol. 91, pp. 10747-10751; Oct. 1994.
Stemmer, Willem P.C.; "Rapid evolution of a protein in vitro by DNA shuffling"; Affymax Research Institute, Nature, vol. 370, Aug. 4, 1994.
Sternberg, M., "Purification of Industrial Enzymes with Polyacrylic Acids", Process Biochemistry, Sep. 1976.
Strickland, James A., et al., "Inhibition of Diabrotica Larval Growth by Patatin, the Lipid Acyl Hydrolase from Potato Tubers", Plant Physiol, vol. 109, pp. 667-674, 1995.
Sudbery et al (1988) Biochem Soc Trans. 16(6), 1081-3.
Sugatani, Junko, et al., "Studies of a Phospholipase B from Penicillium Notatum Substrate Specificity and Properties of Active Site", Biochimica et Biophysica Acta, vol. 620, 1980, pp. 372-386.
Sugimoto et al., Agric. Biol. Chem. 47(6), 1201-1206 (1983).
Sugiyama et al., "Molecular cloning of a second phospholipase B gene, caPLB2 from Candida albicans", Medical Mycology, vol. 37, 1999.
Svendsen, A. "Engineered lipases for practical use", INFORM (1994) 5(5):619-623.
Svendsen, Allan, "Lipase protein engineering" Biochimica et Biophysica Acta, vol. 1543, 2000, pp. 223-238.
Svendsen, Allan, et al., "Biochemical properties of cloned lipases from the *Pseudomonas* family", Biochimica et Biophysica Acta, vol. 1259, 1995, pp. 9-17.
Sweigard, James A., et al., "Cloning and analysis of CUT1, a cutinase gene from *Magnaporthe grisea*", Mol. Gen. Genet., 232:174-182, 1992.
Swinkels et al (1993) Antonie van Leeuwenhoek 64, 187-201.
Sztajer H et al Acta Biotechnol, vol. 8, 1988, pp. 169-175.
Talker-Huiber, Cynthia Z., et al., "Esterase EstE from *Xanthomonas vesicatoria* (Xv_EstE) is an outer membrane protein capable of hydrolyzing long-chain polar esters", Appl. Microbiol Biotechnol, 61:479-487, 2003.
Terasaki, Masaru, et al., "Glycerolipid Acyl Hydrolase Activity in the Brown Alga Cladosiphon okamuranus Tokida", Biosci. Biotechnol. Biochem., vol. 67, No. 9, pp. 1986-1989, 2003.
The First European Symposium of Enzymes on Grain Processing—Proceedings.
The New Enzyme Operatives, Ingredient Technology, 50, Aug. 1997.
Thommy L-G; Carlson, "Law and Order in Wheat Flour Dough; Colloidal Aspects of the Wheat Flour Dough and its Lipid and Protein Constitutents in Aqueous Media", Fortroligt, Lund 1981.
Thornton et al 1988 Biochem. Et Biophys. Acta. 959, 153-159.
Tiss, Aly, et al., "Effects of Gum Arabic on Lipase Interfacial Binding and Activity", Analytical Biochemistry, vol. 294, pp. 36-43, 2001.
Toida J et al, Bioscience, Biotechnology, and Biochemistry, Jul. 1995, vol. 59, No. 7, pp. 1199-1203.
Tombs and Blake, Biochim. Biophys (1982) 700:81-89.
Topakas, E., et al. "Purification and characterization of a feruloyl esterase from *Fusarium oxysporum* catalyzing esterification of phenolic acids in ternary water—organic solvent mixtures", Journal of Biotechnology, vol. 102, 2003, pp. 33-44.
Torossian and Bell (Biotechnol. Appl. Biochem., 1991, 13:205-211.
Tsao et al. (1973) J Supramol Struct. 1(6), 490-7.
Tsuchiya, Atsushi et al, Cloning and Nucelotide Sequence of the Mono-and Diacylglycerol Lipase Gene (mdlB) of *Aspergillus Oryzae*, Fems Microbiology Letters (1996) vol. 143, pp. 63-67.
Tsuneo Yamane et al., "Glycerolysis of Fat by Lipase", Laboratory of Bioreaction Engineering, vol. 35, No. 8, 1986.
Tsychiya, Atsushi, et al., "Cloning and nucleotide sequence of the mono- and diacylglycerol lipase gene (mdlB) of *Aspergillus oryzae*", Fems Microbiology Letters, vol. 143, pp. 63-67, 1996.
Turnbull, K.M., et al., "Early expression of grain hardness in the developing wheat endosperm", Planta, 2003, vol. 216, pp. 699-706.
Turner, Nigel A., et al., "At what temperature can enzymes maintain their catalytic activity?", Enzyme and Microbial Technology, vol. 27, 2000, pp. 108-113.
Turner, Progress in Industrial Microbiology, Martinelli and Kinghorn (eds.), Elsevier, Amsterdam, 1994, 29:641-666.
Unknown, "Appendix: Classification and Index of Fungi mentioned in the Text" in *Unknown*, p. 599-616.
Unknown, "Section I: Structure and Growth—Chapter 1: An Introduction to the Fungi" in *Unknown* pp. 1-16.
Unknown, *Studies on Lipase* (1964) p. 21.
Uppenberg, Jonas, et al., "Crystallographic and Molecular-Modeling Studies of Lipase B from Candida antarctia Reveal a Stereospecificity Pocket for Secondary alcohols", Biochemistry, 1995, vol. 34, pp. 16838-16851.
Uppenberg, Jonas, et al., "The Sequence, crystal structure determination and refinement of two crystal forms of lipase B from Candida antarctica", Structure 1994, vol. 2, No. 4.
Upton C et al TIBS Trends in Biochemical Sciences, Elsevier Publication (1995), vol. 20, pp. 178-179.
USDA, United States Department of Agriculture Agriculture Research Services, "Production of an Industrially Useful Fungal Lipase by a Genetically Altered Strain of *E. coli*", New Technology. http://www.ars.usda.gov/Main/docs.htm?docid=8785.
Uusitalo et al. (1991) J Biotechnol. 17(1), 35-49.
Uwajima T et al, Agricultural and Biological Chemistry, 43(12), pp. 2633-2634, 1979.

Uwajima T et al, Agricultural and Biological Chemistry, 44(9), pp. 2039-2045, 1980.
Uwajima T et al, Methods in Enzymology, 89(41), pp. 243-248.
Vaidehi, et al.; "Lipase Activity of Some Fungi Isolated from Groundnut"; Current Science (1984); vol. 53(23); p. 1253.
Van Binsbergen, Jan, et al., "Substitution of PHE-5 and ILE-9, Amino Acids Involved in the Active Site of Phospholipase A2 (PLA), and Chemical Modification of Enzymatically Generated (LYS-6)-PLA.", Proceedings of the 20th European Peptide Symposium, Sep. 4-9, 1988, University of Tubingen.
Van Den Berg. G, Regulatory status and use of lipase in various countries.
Van Gemeren, I.A., et al., "Expression and Secretion of Defined Cutinase Variants by *Aspergillus awamori*" Applied and Environmental Microbiology, vol. 64, No. 8, pp. 2794-2799, Aug. 1998.
Van Kampen, M.D., et al., "The phospholipase activity of *Staphylococcus hyicus* lipase strongly depends on a single Ser to Val mutation", Chemistry and Physics of Lipids, vol. 93, 1998, pp. 39-45.
Van Nieuqenhuyzen W., "Lecithins Open Doors to baked goods", International Food Ingredients, 1998, No. 2, p. 32-36.
Van Oort, Maarten G et al, Biochemistry 1989 9278-9285.
Van Solingen, Pieter, et al., "The cloning and characterization of the acyltransferase gene of penicillium chrysogenum", Agricultural University, Wageningen, the Netherlands p. 47, (Date unknown).
Vaysse et al J. Of Biotechnology 53 (1997) 41-46.
Villenueva, Infonn, vol. 8, No. 6, Jun. 1997.
Vujaklija, Dušica, et al., "A novel streptomycete lipase: cloning, sequencing and high-level expression of the *Streptomyces rimosus* GDS (L)-lipase gene", Arch. Microbiol, vol. 178, pp. 124-130, 2002.
Wahnelt S.V., Meusel D, & Tülsner M, (1991) Zur kenntnis des diglyceride influsses auf das kristallisationsverhalten von Fetten, in Fat Science Technology 4:117-121.
Waninge, Rianne, et al., "Milk membrane lipid vesicle structures studied with Cryo-TEM", Colloids and Surfaces B: Biointerfaces 31 (2003), pp. 257-264.
Warmuth et al, 1992, Bio Forum 9, 282-283.
Watanabe et al. Bio sci Biochem 63(5) 820-826, 1999.
Watanabe, Yasuo et al., "Cloning and sequencing of phospholipase B gene from the yeast Torulaspora delbrueckii", FEMS Microbiology Letters, vol. 124, 1994, pp. 29-34.
Webb EC, Enzyme Nomenclature, 1992, p. 310.
Weber et al. J Agric Food Chem 1985, 33, 1093-1096.
Welter, et al; "Identification of Recombinant DNA"; pp. 424-431.
Wen-Chen Suen et al., "Improved activity and thermostability of Candida antarctica lipase B by DNA family shuffling", Protein Engineering, Design & Selection, vol. 17, No. 2, pp. 133-140, 2004.
West S.; "Olive and Other Edible Oils"; Industrial Enzymology (1996); pp. 295-299.
Whitaker, John R., et al., "Biocatalysis in Agricultural Biotechnology", ACS Symposium Series, American Chemical Society, 1989, p. 25-43.
Whitehead, Michael, et al., "Transformation of a nitrate reductase deficient mutant of Penicillium chrysogenum with the corresponding *Aspergillus niger* and A. nidulans niaD genes", Mol Gen Genet, 216: 408-411, 1989.
Wilhelm et al., "A Novel Lipolytic Enzyme Located in the Outer Membrane of *Pseudomonas aeruginosa*", Journal of Bacteriology, vol. 181, No. 22, Nov. 1999, pp. 6977-6986.
Williams K.R. et al., "Protein Analysis by Integrated Sample Preparation, Chemistry, and Mass Spectrometry", in Molecular Biology and Biotechnology—A Comprehensive Desk Reference, VCH, 1995, ISBN 1-56081-569-8 edited by Meyers R.A., p. 731-737.
Winnacker et al., "Identification of Recombinant DNA", chapter 11 in "From genes to clones: introduction to gene technology," by E. -L. Weinnacke, VCH, Weinheim, ISBN 0-89573-614-4, pp. 424-431.
Winnacker, E. "Chapter 11: Identification of Recombinant DNA" in *From Genes to Clones: Introduction to Gene Technology*, 1987 John Wiley & Sons.
Winther, Ole, et al., "Teaching computers to fold proteins", Physical Review, vol. 70, No. 030903, 2004.
Helmerich G. et al., Strukur-Wirkungsbeziehehungen von Phospholipiden in Backwaren, Wirkung von Phospholipiden, Getreide Mehl and Brot, 2003, vol. 57, No. 5, p. 270-273 NZAS-0301096.
Withers-Martinez, Chrislaine, et al., "A pancreatic lipase with a phospholipase A1 activity: crystal structure of a chimeric pancreatic lipase-related protein 2 from guinea pig", Structure, 1996, vol. 4, No. 11.
Witt, Wolfgang et al., "Secretion of Phospholipase B From Saccharomyces Cerevisiae", Biochimica et Biophysica Acta, vol. 795, 1984, pp. 117-124.
Kelley R.L. And Reddy C.A., Glucose Oxidase of Phanerochaete chrysosporium, in "Biomass, Part B, Lignin, Pectin, and Chitin", Wood et al., Eds., Methods in Enzymology (1988) vol. 161, Academic Press, San Diego, p. 307-316.
Woolley et al., "Lipases their structure, biochemistry and application", Cambridge University Press (1994) p. 242-270.
WPI Acc No. 93-298906(38) and JP05211852 Preparation of low fat content cream-by adding lipase to mixture of fat and water, Nisshin Oil and Fat Corp. Aug. 24, 1993.
Xu, Jun, et al., "Intron requirement for AFP gene expression in Trichoderma viride", Microbiology, 2003, vol. 149, pp. 3093-3097.
Yamaguchi et al, 1991, Gene 103:61-67.
Yamane et al., "High-Yield Diacylglycerol Formation by Solid-Phase Enzymatic Glycerolysis of Hydrogenated Beef Tallow", JAOCS, vol. 71, No. 3, Mar. 1994.
Yamano Y et al., Surface activity of lysophosphatidyl choline from soybean, 4th World Surfactants Congress, 1996, p. 24-34.
Yamauchi, Asao et al., "Evolvability of random polypetides through functional selection within a small library", Protein Engineering, vol. 15, No. 7, pp. 619-626, 2002.
Yang, Baokang, et al., "Control of Lipase-Mediated Glycerolysis Reactions with Butteroil in Dual Liquid Phase Media Devoid of Organic Solvent", J. Agric. Food Chem., 1993, vol. 41, pp. 1905-1909.
Yount, Nannette Y., et al., "Multidimensional signatures in antimicrobial peptides" PNAS (2004) vol. 101, No. 10, p. 7363-7368.
Zaks, Aleksey, et al., "Enzyme-catalyzed processes in organic solvents", Proc. Natl. Acad. Sci. USA, vol. 82, pp. 3192-3196, May 1985.
Zaks, Aleksey, et al., "The Effect of Water on Enzyme Action in Organic Media", The Journal of Biological Chemistry, vol. 263, No. 17, Issue of Jun. 15, pp. 8017-8021, 1988.
Zangenbert, Niels Honberg, et al., "A dynamic in vitro lipolysis model 1. Controlling the rate of lipolysis by continuous addition of calcium", European Journal of Pharmaceutical Sciences, vol. 14, 2001, pp. 115-122.
Zangenbert, Niels Honberg, et al., "A dynamic in vitro lipolysis model II. Evaluation of the model", European Journal of Pharmaceutical Sciences, vol. 14, 2001, pp. 237-244.
Zhang, Hong, et al., "Modification of Margarine Fats by Enzymatic Interesterification: Evaluation of a Solid-Fat-Content-Based Exponential Model with Two Groups of Oil Blends", JAOCS, vol. 81, No. 1, 2004.
Nerland A.H., "The Nucleotide Sequence of the Gene Encoding GCAT from *Aeromonas salmonicida* SSP. *Salmonicida*", Journal of Fish Diseases, 1996, vol. 19, No. 2, pp. 145-150, XP008049669.
U.S. Appl. No. 60/083,277, filed Apr. 28, 1998, Spender, Tina, et al.
AACC Method 54-21 Farinograph Method for Flour, from Physical Dough Tests supplied by the British Library, Nov. 3, 1999.
Anguita et al, "Purification, Gene Cloning, Amino Acid Sequence Analysis, and Expression of an Extracellular Lipase from an *Aeromonas hydrophila* Human Isolate", Appl. Environ. Microbiol., vol. 59, No. 8, p. 2411-2417, Aug. 1993.
"AOAC Official method 999.10 (Lead, Cadmium, Zinc, Copper, and Iron in Foods Atomic absorption Spectrophotometry after Microwave Digestion), First Action 1999 NMKL-AOAC Method", AOAC International, pp. 1-3, 2002.
AOCS Method 2c-25 "1997 Moisture and Volatile Matter Air Oven Method" Sampling and Analysis of Commercial Fats and Oils, obtained from The British Library, p. 1, 1997.

AOCS Official Method Ca 20-99: "Analysis of Phosphorus in oil by inductively Coupled Plasma Optical Emission Spectroscopy", Sampling and Analysis of Commercial Fats and Oils, obtained from The British Library, pp. 1-3, 2001.
Arskog and Joergensen, "Baking performance of prior art lipases from *Candida cylindracea* and *Aspergillus foeditus* and their activity on galactolipids in dough", Novozymes Report Jul. 18, 2005, pp. 1-2.
Arskog and Joergensen, "Baking performance of prior art lipases from *Humicola Lanuginosa, Aspergillus tubigensis, Rhizopus delemar* and *Rhizomucor miehei*, and their activity on galactolipids in dough", Novozymes Report Jul. 17, 2005, pp. 1-8.
EC 1.1.3.10 (downloaded—Jul. 12, 2010 from http://www.chem.qmul.ac.uk/iubmb/enzyme/EC1/1/3/10.html).
EC 1.1.3.4 (downloaded—Jul. 12, 2010 from http://www.chem.qmul.ac.uk/iubmb/enzyme/EC1/1/3/4.html).
EC 1.1.3.5 (downloaded— Nov. 16, 2009 from http://www.chem.qmul.ac.uk/iubmb/enzyme/EC1/1/3/5.html).
EC 2.3.1.43 (downloaded Apr. 21, 2009 from http://www.chem.qmul.ac.uk/iubmb/enzyme/EC2/3/1/43.html).
EC 2.4.1.19 (Downloaded Jul. 12, 2010 from http://www.chem.qmul.ac.uk/iubmb/enzyme/EC2/4/1/19.html).
EC 3.1.1.26 (downloaded—Dec. 18, 2008 from http://www.chem.qmul.ac.uk/iubmb/enzyme/EC3/1/1/26.html).
EC 3.1.1.3 (downloaded—Dec. 18, 2008 from http://www.chem.qmul.ac.uk/iubmb/enzyme/EC3/1/1/3.html).
EC 3.1.1.32 (downloaded—May 22, 2008 from http://www.chem.qmul.ac.uk/iubmb/enzyme/EC3/1/1/32.html).
EC 3.1.1.4 Phospholipase A2 enzyme Enzyme Entry 1983 (downloaded Apr. 21, 2009 from http://www.chem.qmul.ac.uk/iubmb/enzyme/EC3/1/1/4.html).
EC 3.1.1.5 (downloaded Dec. 18, 2008 from http://www.chem.qmul.ac.uk/iubmb/enzyme/EC3/1/1/5.html).
EC 3.2.1.3 (downloaded Jul. 12, 2010 from http://www.chem.qmul.ae.uk/iubmb/enzyme/EC3/2/1/3.html).
EC 3.2.1.32 (Downloaded Jul. 12, 2010 from http://www.chem.qmul.ac.uk/iubmb/enzyme/EC3/2/1/32.html).
EC 3.2.1.60 (downloaded Apr. 28, 2009 from http://www.chem.qmul.ac.uk/iubmb/enzyme/EC3/2/1/60.html).
Eliasson A-C. and Larssen K., "Chapter 2: Physiochemical Behavior of the Components of Wheat Flour", *Cereals in Breadmaking: a molecular colloidal approach*, Marcel Dekker Inc, 1993, ISBN0824788168, p. 31-45.
Genbank accession code NC_003888.1:8327480..8328367 (downloaded Apr. 21, 2009), p. 1.
Genbank accession No. AL646052 (downloaded Apr. 21, 2009), pp. 1-2.
Genbank accession No. AL939131.1:265480..266367 (downloaded Apr. 21, 2009), p. 1.
Genbank accession No. CAC42140 (downloaded Apr. 21, 2009), pp. 1-2.
Genbank accession No. NP_631558 (downloaded Apr. 21, 2009), pp. 1-2.
Genbank accession No. P41734 (downloaded Apr. 21, 2009), pp. 1-4.
Genbank accession No. Z75034 (downloaded Apr. 21, 2009), pp. 1-2.
Hinnen A. et al., Transformation of yeast, Proceedings of the National Academy of Sciences USA, Apr. 1978, vol. 75, No. 4, p. 1929-1933.
HUI, Bailey's Industrial Oil and Fat Products, 5th edition vol. 2 Edible Oil and Fat Products: Oils and Oilseeds, Wiley Interscience (1996), pp. 513-516. ISBN 0471594261.
Jost R. et. al., "Milk and Dairy Products," Nestle Product Technology Center, 2007, Wiley-VCH, pp. 1-62, Konolfingen, Switzerland.
NCBI protein accession code AAK84028.1 GI:15082088, (downloaded Dec. 18, 2009), pp. 1-2.
NCBI protein accession code CAB39707.1 GI:4529178, (downloaded Dec. 18, 2009), pp. 1-2.
NCBI protein accession code CAB62724.1 GI:6562793, (downloaded Dec. 18, 2009), pp. 1-2.
NCBI protein accession code CAB88833.1 GI:7635996, (downloaded Dec. 18, 2009), pp. 1-2.
NCBI protein accession code CAB89450.1; GI:7672261, (downloaded Dec. 18, 2009), pp. 1-2.
NCBI protein accession code CAC01477.1 GI:9716139, (downloaded Dec. 18, 2009), pp. 1-2.
NCBI's Genbank database accession number: 1IVN_A; GID:33357066, (downloaded Oct. 14, 2010), pp. 1-2.
Nerland A.H., "Glycerophospholipid-cholesterol acyltransferase precursor", SwissProt, Feb. 11, 2005 XP002318368 citing Nerland, A.H., "The nucleotide sequence of the gene encoding GCAT from *Aeromonas salmonicida* ssp. *Salmonicida*," Journal of Fish Diseases, vol. 19, p. 145-150, 1996.
Phospholipase C, E.C. 3.1.4.3, (downloaded Sep. 8, 2009 from http://www.chem.qmul.ac.uk/iubmb/enzyme/EC3/1/4/3.html), p. 1.
PreSens Manual HydroPlate® HP96U and HydroPlate® HP96C, pp. 1-15, Aug. 17, 2004.
Sequence alignment of database accession No. Q44268 (database: UNIProtKB/TrEMBL) with SEQ. ID No. 16, (downloaded Jan. 27, 2009), pp. 1-2.
Sequence alignment of database accession No. Q44268 (database: UNIProtKB/TrEMBL) with SEQ. ID No. 70, (downloaded Jan. 27, 2009), pp. 1-2.
Notification of Reasons for Refusal: JP Application No. 526105, Feb. 12, 2003 (Translation).
Notification of Reasons for Refusal: JP Application No. 526105, Jun. 4, 2002 (Translation).
Written Argument: JP Application No. 97181706.5, (Dec. 9, 1997) (Translation).
Internal Novo Nordisk Ref. No. DK5559215, p. 3-10 (NZAS-0017041-0017048) submitted during litigation.
Patent Abstracts of Canada, Publication No. CA 805618, Publication Date Feb. 4, 1969.
Kin-Yu Chan et al., "Direct Colorimetric Assay of Free Thiol Groups and Disulfide Bonds in Suspensions of Solubilized and Particulate Cereal Proteins", Cereal Chem., vol. 70, No. 1, pp. 22-26.
Rebeca Garcia et al., "Analysis and Modelling of the Ferulic Acid Oxidation by a Glucose Oxidase-Peroxidase Association. Comparison with a Hexose Oxidase-Peroxidase Association", J. Agric. Food Chem., 2004, vol. 52, pp. 3946-3953 .
Buckley J. Thomas, "Substrate specificity of bacterial glycerophospholipid: Cholesterol Acyltransferase", Biochemistry, 1982, vol. 21, pp. 6699-6703.
U.S. Appl. No. 60/083,277, filed Apr. 28, 1998, Spendler et al.
Marion D—Chapter 6, pp. 131-167 of "*Interactions The Keys to Cereal Quality*" 1998 ISBN 0 913250-99-6 (ed. Hamer & Hoseney).
Marion D et al.—pp. 245-260 of Wheat Structure Biochemistry & Functionality (ed. Schofield JP) ISBN 085404777-8 published in 2000—(Proceedings of Conference organized by Royal Soc of Chemistry Food Chemistry Group held on Apr. 10-12, 1995, in Reading, UK,).
Angelino S A G F et al. ed. The proceedings of the First European Symposium on Enzymes and Grain Processing. TNO Nutrition and Food Research Institute, Zeist, The Netherland, 1997.
Matos et al., "*A novel patatin-like gene stimulated by drought stress encodes a galactolipid acyl hydrolase," Federation of European Biochemical Societies*, published by Elsevier Science B.V., 2001.
Martinez et al., "*A pancreatic lipase with a phospholipase A1 activity: crystal structure of a chimeric pancreatic lipase-related protein 2 from guinea pig," Current Biology Ltd.*, Nov. 15, 1996, 4:1363-1374.
Cordle et al., "*The hydrophobic surface of colipase influences lipase activity at an oil-water interface," Journal of Lipid Research*, vol. 39, 1998, 1759-1767.
Sahsah et al., "*Purification and characterization of soluble lipolytic acylhydrolase from Cowpea* (*Vigna unguiculata* L.) *leaves," Biochimica et Biophysica Acta 1215* (1994), 66-73.
O'Sullivan et al., *A Galactolipase Activity Associated with the Thylakoids of Wheat Leaves* (*Triticum aestivum* L.), *J. Plant Physiol*, vol. 131, pp. 393-404 (1987).
Carriere et al., "*Pancreatic Lipase Structure—Function Relationships by Domain Exchange," American Chemical Society—Biochemistry*, 1997, 36, pp. 239-248.
Bornscheur, "*Lipase—catalyzed syntheses of monoacylglycerols," Enzymes Microb. Technol.*, 1995, vol. 17, Jul., pp. 578-586.
Krog, "*Dynamic and Unique Monoglycerides," Cereal Foods World*, The American Association of Cereal Chemists, p. 10, Jan. 1979, vol. 24, No. 1, pp. 10-11.
Hou, "*pH dependence and thermostability of lipases from cultures from the ARS Culture Collection," Journal of Industrial Microbiology*, Society for the Industrial Microbiology, 13 (1994), 242-248.
Villenueva et al., "*Lipase specificities: Potential application in lipid bioconversions," Inform*, vol. 8, No. 6, (Jun. 1997).

LANE 1-3:
POOL FROM PQ10

NATIVE-PAGE
(NU-PAGE, 4-12%, MES-BUFFER)

THIS PART OF THE GEL
WAS CUT OUT AND THEN
SUBJECTED
TO ELECTRO ELUTION

ACTIVITY STAINING, DGDG-PLATE
40°C, 18 HOURS

GALACTOLIPASE
ACTIVITY

PROTEIN: COW PEA LIPASE
FILE ORIGIN: NO: 0
CLEAVAGE CONDITIONS: /K/R-\P

[GPMAW] 16/ 5/2002
MASS FILE: CM-CYS

---

MASS SHOWN IS: AVERAGE

| NO | FROM- | TO | MASS | CH | B&B | HPLC | SEQ. |
|---|---|---|---|---|---|---|---|
| 1 | 1- | 9 | 934.09 | 1 | 2820 | 9.39 | MAATQTPSK |
| 2 | 10- | 27 | 1771.01 | -2 | -2070 | 23.25 | VDDGALITVLSIDGGGIR |
| 3 | 28- | 44 | 1841.23 | -1 | -7540 | 29.28 | GIIPGILLAFLESELQK |
| 4 | 45- | 51 | 716.75 | -1 | 2290 | 9.23 | LDGADAR |
| 5 | 52- | 86 | 3656.14 | -1 | -1710 | 27.25 | LADYFDVIAGTSTGGLVTAMLTAPNENNRPLYAAK |
| 6 | 87- | 89 | 374.44 | 0 | -380 | 6.68 | DIK |
| 7 | 90- | 98 | 1149.27 | 0 | -2210 | 17.71 | DFYLEHTPK |
| 8 | 99- | 114 | 1794.11 | 1 | -3010 | 24.71 | IFPQSSSWNLIATAMK |
| 9 | 115- | 115 | 146.19 | 1 | 460 | 1.09 | K |
| 10 | 116- | 117 | 231.26 | 1 | 1500 | 2.11 | GR |
| 11 | 118- | 127 | 1095.25 | 0 | 170 | 16.42 | SLMGPQYDGK |
| 12 | 128- | 131 | 559.67 | 2 | -1930 | 12.20 | YLHK |
| 13 | 132- | 134 | 386.50 | 1 | -1710 | 8.75 | LVR |
| 14 | 135- | 136 | 275.31 | 0 | 970 | 1.51 | EK |
| 15 | 137- | 141 | 531.61 | 1 | 800 | 5.45 | LGNTK |
| 16 | 142- | 157 | 1010.13 | 0 | -5040 | 22.49 | LEHTLTNVVIPAFDIK |
| 17 | 158- | 170 | 1478.72 | 1 | -2320 | 22.19 | NLQPAIFSSFQVK |
| 18 | 171- | 171 | 146.19 | 1 | 460 | 1.09 | K |
| 19 | 172- | 201 | 3368.74 | 1 | -2990 | 30.83 | RPYLNAALSDICISTSAAPTYLPAHCFETK |
| 20 | 202- | 208 | 740.82 | 1 | 970 | 9.94 | TSTASFK |
| 21 | 209- | 234 | 2673.00 | -3 | 590 | 21.46 | FDLVDGGVAANNPALVAMAEVSNEIR |
| 22 | 235- | 243 | 965.01 | 0 | 2830 | 12.66 | NEGSCASLK |
| 23 | 244- | 250 | 875.08 | 2 | -2110 | 14.08 | VKPLQYK |
| 24 | 251- | 251 | 146.19 | 1 | 460 | 1.09 | K |
| 25 | 252- | 267 | 1803.08 | 1 | -1100 | 23.26 | FLVISLGTGSQQHEMR |
| 26 | 268- | 272 | 582.62 | 0 | 670 | 7.13 | YSADK |
| 27 | 273- | 313 | 4353.84 | 0 | -4340 | 35.98 | ASTWGLVGWLSSSGGTPLIDVFSHASSDMVDFHISSVFQAR |
| 28 | 314- | 321 | 1030.11 | 1 | 1280 | 12.48 | HAEQNYLR |
| 29 | 322- | 340 | 1977.11 | -4 | 1650 | 18.47 | IQDDTLTGDLGSVDVATEK |
| 30 | 341- | 354 | 1481.76 | 0 | -2350 | 18.34 | NLNGLVQVAEALLK |
| 31 | 355- | 359 | 557.70 | 2 | 420 | 4.85 | KPVSK |
| 32 | 360- | 363 | 514.63 | 1 | -1520 | 10.70 | INLR |
| 33 | 364- | 381 | 1939.07 | -2 | 3980 | 14.73 | TGIHEPVESNETNAEALK |
| 34 | 382- | 382 | 174.21 | 1 | 690 | 1.41 | R |
| 35 | 383- | 386 | 463.54 | 1 | 390 | 9.62 | FAAR |
| 36 | 387- | 391 | 616.68 | 1 | 1320 | 7.10 | LSNQR |
| 37 | 392- | 392 | 174.21 | 1 | 690 | 1.41 | R |
| 38 | 393- | 394 | 321.38 | 1 | -830 | 8.94 | FR |
| 39 | 395- | 395 | 146.19 | 1 | 460 | 1.09 | K |
| 40 | 396- | 400 | 552.59 | 0 | 770 | 10.45 | SQTFA |

FIG. 13

METHOD OF IMPROVING DOUGH AND BREAD QUALITY

Matter enclosed in heavy brackets [ ] appears in the original patent but forms no part of this reissue specification; matter printed in italics indicates the additions made by reissue.

This application claims benefit of 60/347,007 filed on Jan. 9, 2002.

FIELD OF THE INVENTION

The present invention relates to dough manufacture and flour dough based products and in particular, but not exclusively, to improving the strength and machinability of doughs and the volume, softness and crumb structure of bread and other baked products.

TECHNICAL BACKGROUND

Additives are widely used within the food industry in order to improve the quality of the food product. One of the most widely used food additives is the emulsifier and in particular monoglyceride.

Monoglyceride was originally produced as a mixture of mono-, di- and triglycerides. However, later technology was developed to produce highly purified monoglyceride by molecular distillation. Monoglyceride is traditionally produced by a glycerolysis reaction, wherein triglyceride and glycerol are reacted at high temperature above 200° C. using alkaline catalysts.

As an alternative to using alkaline catalysts and high temperatures many attempts have been made to use enzymes such as lipases in the production of monoglycerides. In a review article, Bornscheuer (Enzyme and Microbial Technology 17:578-585, 1995) mentions the enzymatic glycerolysis of triglycerides in the presence or absence of solvents and that monoglyceride can be produced by enzymatic glycerolysis in a solid phase.

Monoglyceride can be used as an emulsifier for many food applications. Within the baking industry, monoglyceride has been used to improve bread softness by complexing with starch and thereby retarding the crystallisation of amylopectin and the onset of bread staling.

Lipases (E.C. 3.1.1.3) have also been used directly in bread production. For instance, in EP 0 585 988 it is claimed that lipase addition to dough resulted in an improvement in the antistaling effect. It is suggested that a lipase obtained from Rhizopus arrhizus when added to dough can improve the quality of the resultant bread when used in combination with shortening/fat. WO94/04035 teaches that an improved softness can be obtained by adding a lipase to dough without the addition of any additional fat/oil to the dough. Castello, P. ESEGP 89-10 December 1999 Helsinki, shows that exogenous lipases can modify bread volume. Thus, lipases (E.C. 3.1.1.3) which hydrolyse triacylglycerols were known to be advantageous for use in the baking industry.

It has been shown in WO 98/45453 that the level of monoglyceride in doughs treated with lipase only increases very slightly, as the lipase added to the dough easily degrades monoglyceride to glycerol and free fatty acids. This is explained by the fact that lipases recognise the fatty acid part of the molecule in the active site and as monoglycerides and diglycerides are more orientated at the interface where the lipase is active, monoglycerides and diglycerides are easily degraded during lipase addition to a matrix containing fat/oil emulsions. Even with regard to 1.3 specific lipases, which only hydrolyse the fatty acids of a triglyceride in the 1 and 3 position leaving 2-monoglyceride as the reaction product, the resultant 2-monoglyceride easily rear-ranges to 1-monoglyceride, which can be hydrolysed by 1.3 specific lipases.

During enzymatic degradation of triglycerides by conventional lipases monoglycerides, diglycerides, free fatty acids and glycerol are formed.

Typically, the increase in monoglycerides in dough treated with one or more lipases is less than 0.1% (based on flour weight) with or without added fat or oil. However, the conventional dosage of monoglyceride required in dough to result in an improvement in, for instance, softness of the resultant bread is typically about 0.3-0.8% based on flour weight (Krog, N. Cereal Food World, 24, 10, 1979). Thus, any beneficial effect of adding conventional lipases to dough, as suggested in EP 0 585 988 and WO94/04035, is not a result of an increased monoglyceride content alone.

Some lipases in addition to having a triglyceride hydrolysing effect, are capable of hydrolysing polar lipids such as glycolipids, e.g. digalactosyldiglyceride (DGDG), and phospholipids (see for instance WO01/39602).

The substrate for lipases in wheat flour is 2-3% endogenous wheat lipids, which are a complex mixture of polar and non-polar lipids. The polar lipids can be divided into glycolipids and phospholipids. These lipids are built up of glycerol esterified with two fatty acids and a polar group. The polar group contributes to surface activity of these lipids. Enzymatic cleavage of one of the fatty acids in these lipids leads to lipids with a much higher surface activity. It is well known that emulsifiers, such as DATEM, with high surface activity are very functional when added to dough.

It has been found, however, that the use of lipases (E.C. 3.1.1.3) in dough may under certain conditions have detrimental consequences, such as the production of off-flavours, a detrimental impact on yeast activity, and/or a negative effect on bread volume. The negative effect on bread volume is often called overdosing. Overdosing can lead to a decrease in gluten elasticity which results in a dough which is too stiff and thus results in reduced volumes. In addition, or alternatively, such lipases can degrade shortening, oil or milk fat added to the dough.

SUMMARY ASPECT

A seminal finding of the present invention is that, surprisingly, the use of an enzyme, which under dough conditions is capable of hydrolysing a glycolipid and a phospholipid, but which is incapable, or substantially incapable, of hydrolysing a triglyceride and/or a 1-monoglyceride, is advantageous, and overcomes the disadvantages associated with the use of lipases (E.C. 3.1.1.3) which are capable of hydrolysing non-polar lipids in a dough.

DETAILED ASPECTS

The present invention provides in a first aspect a method of preparing a flour dough, said method comprising adding to the dough components an enzyme that under dough conditions is capable of hydrolysing a glycolipid and a phospholipid, wherein said enzyme is incapable, or substantially incapable, of hydrolysing a triglyceride and/or a 1-monoglyceride, and mixing the dough components to obtain the dough.

In a second aspect of the present invention, there is provided a method of preparing a dough or baked product prepared from a dough comprising:

(a) testing at least one enzyme for its hydrolytic activity towards a triglyceride, a 1-monoglyceride, a phospholipid and a glycolipid;

(b) selecting an enzyme having hydrolytic activity towards a phospholipid and a glycolipid and having no, or substantially no, hydrolytic activity towards a triglyceride and/or a 1-monoglyceride; and (c) adding the selected enzyme to the dough.

The present invention provides in a third aspect a dough improving composition comprising an enzyme having hydrolytic activity towards a phospholipid and a glycolipid and having no, or substantially no, hydrolytic activity towards a triglyceride and/or a 1-monoglyceride and, optionally, a further dough component.

In a fourth aspect, the present invention provides a dough obtainable by the method according to the present invention.

In a fifth aspect, the present invention provides a dough obtained by the method according to the present invention.

In a sixth aspect, the present invention provides a baked product obtainable by baking a dough according to the present invention.

In a seventh aspect, the present invention provides a baked product obtained by baking a dough according to the present invention.

The present invention further provides, in an eighth aspect, a noodle product made from a dough according to the present invention.

In a ninth aspect, the present invention provides a pasta product made from a dough according to the present invention.

In an tenth aspect, the present invention provides a method of preparing a dough improving composition wherein an enzyme having hydrolytic activity towards a phospholipid and a glycolipid and having no, or substantially no, hydrolytic activity towards a triglyceride and/or a 1-monoglyceride is, optionally, admixed with a further dough component.

In an eleventh aspect, a method of selecting an enzyme according to the present invention may comprise the steps of:

(a) testing at least one enzyme for its hydrolytic activity towards a triglyceride, a 1-monoglyceride, a phospholipid and a glycolipid;

(b) selecting an enzyme having hydrolytic activity towards a phospholipid and a glycolipid and having no, or substantially no, hydrolytic activity towards a triglyceride and/or a 1-monoglyceride.

The present invention provides in a twelfth aspect thereof a method of preparing or developing an enzyme having hydrolytic activity towards a phospholipid and a glycolipid and having no, or substantially no, hydrolytic activity towards a triglyceride and/or a 1-monoglyceride, comprising:

(a) selecting a lipase having hydrolytic activity towards a phospholipid, a glycolipid and a triglyceride and/or a 1-monoglyceride, (b) modifying by insertion, deletion or substitution of at least one amino acid in the amino acid sequence, typically near or in the active site, so as to alter the activity of the lipase in such a way that the lipase is modified to have no, or substantially no, activity against a triglyceride and/or a 1-monoglyceride.

In a thirteenth aspect, the present invention provides the use of an enzyme that under dough conditions is capable of hydrolysing a glycolipid and a phospholipid, wherein said enzyme is incapable, or substantially incapable, of hydrolysing a triglyceride and/or a 1-monoglyceride, in the preparation of a dough to provide a dough with increased bread volume and/or increased gluten strength as compared with a dough without said enzyme.

In a fourteenth aspect, the present invention provides a method for removing polar lipids from an edible oil, said method comprising adding to an edible oil an enzyme that is capable of hydrolysing a glycolipid and a phospholipid, wherein said enzyme is incapable, or substantially incapable, of hydrolysing a triglyceride and/or a 1-monoglyceride.

In a fifteenth aspect, the present invention provides an edible oil, such as a soyabean or rapeseed oil, obtainable or obtained by the method according to the present invention.

In a sixteenth aspect, the present invention provides a protein which under dough conditions has one or more of the following characteristics:

i) is capable of hydrolysing a glycolipid and a phospholipid, wherein said enzyme is incapable, or substantially incapable, of hydrolysing a triglyceride and/or a 1-monoglyceride;

ii) a molecular weight of about 57 and/or about 87 kDa when determined by SDS-PAGE analysis;

wherein said protein is obtainable from Vigna unguiculata.

In a seventeenth aspect, the present invention provides a method of preparing a flour dough, said method comprising adding to the dough components an enzyme comprising the amino acid sequence shown in SEQ ID No. 12, or a variant, homologue or derivative thereof and mixing the dough components to obtain the dough.

For ease of reference, these and further aspects of the present invention are now discussed under appropriate section headings. However, the teachings under each section are not necessarily limited to each particular section.

PREFERABLE ASPECTS

Preferably the enzyme capable of hydrolysing a glycolipid and a phospholipid, wherein said enzyme is incapable, or substantially incapable, of hydrolysing a triglyceride and/or a 1-monoglyceride is a lipolytic acyl hyrolase (LAH) (E.C. 3.1.1.26).

Please note that the enzyme number E.C. 3.1.1.26 according to the International Union of Biochemistry and Molecular Biology (IUBMB) recommendations for Enzyme Nomenclature (1992) refers to a "galactolipase" which also acts on 2,3-di-O-acyl-1-O-(6-O-α-D-galactosyl-β-D-galactosyl)-D-glycerol, and phosphatidylcholine and other phospholipids. In the literature (such as, for example, Biochemica et Biophysica Acta 1215 (1994) 66-73) enzymes falling under the enzyme number E.C. 3.1.1.26 have been referred to as lipolytic acyl hydrolases (LAHs) and other such names. The terms galactolipase and lipolytic acyl hydrolase (LAH) as used herein are considered to be synonyms for the same enzyme, i.e. one falling under the E.C. classification 3.1.1.26 and having activity on both galactolipids and phospholipids.

Preferably the enzyme capable of hydrolysing a glycolipid and a phospholipid, wherein said enzyme is incapable, or substantially incapable, of hydrolysing a triglyceride and/or a 1-monoglyceride is isolated from soluble cowpea leaf extract and/or is isolated from wheat leaf thylakoids.

Suitably, the enzyme capable of hydrolysing a glycolipid and a phospholipid, wherein said enzyme is incapable, or substantially incapable, of hydrolysing a triglyceride and/or a 1-monoglyceride may have the amino acid sequence shown in SEQ ID No. 1 or may be a variant, homologue or derivative thereof.

Suitably, the enzyme capable of hydrolysing a glycolipid and a phospholipid, wherein said enzyme is incapable, or substantially incapable, of hydrolysing a triglyceride and/or a 1-monoglyceride may have the amino acid sequence shown in SEQ ID No. 1 or may have an amino acid sequence which is at least 75%, more preferably at least 85%, more preferably at least 90% homologous to SEQ ID No. 1.

Suitably, the enzyme capable of hydrolysing a glycolipid and a phospholipid, wherein said enzyme is incapable, or substantially incapable, of hydrolysing a triglyceride and/or a 1-monoglyceride may be encoded by the nucleotide sequence shown in SEQ ID No. 2 or may be a variant, homologue or derivative thereof.

Suitably, the enzyme capable of hydrolysing a glycolipid and a phospholipid, wherein said enzyme is incapable, or substantially incapable, of hydrolysing a triglyceride and/or a 1-monoglyceride may be encoded by the nucleotide sequence shown in SEQ ID No. 2 or may be encoded by a nucleotide sequence which is at least 75%, more preferably at least 85%, more preferably at least 90% homologous to SEQ ID No. 2.

Suitably, the enzyme capable of hydrolysing a glycolipid and a phospholipid, wherein said enzyme is incapable, or substantially incapable, of hydrolysing a triglyceride and/or a 1-monoglyceride may be a protein has a molecular weight of about 57 kDa and/or about 87 kDa when determined by SDS-PAGE analysis and which is obtainable from Vigna unguiculata.

Preferably, the protein having a molecular weight of about 57 and/or about 87 kDA is isolated using the same method as detailed herein.

The term "an enzyme that under dough conditions is capable of hydrolysing a glycolipid and a phospholipid, wherein said enzyme is incapable, or substantially incapable, or hydrolysing a triglyceride and/or a 1-monoglyceride includes an enzyme that under dough conditions hydrolyses a glycolipid and a phospholipid, but which does not, or does not substantially, hydrolyse a triglyceride and/or a 1-monoglyceride.

For some embodiments the enzyme may be added in the form of a composition comprising said enzyme.

An effective amount of the enzyme should be added, such that the enzyme, under dough conditions or degumming conditions, is capable of hydrolysing a glycolipid and a phospholipid, and is incapable, or substantially incapable, of hydrolysing a triglyceride and/or a 1-monoglyceride. Alternatively or in addition, an effective amount of a composition containing said enzyme may be added to the dough either directly to an already mixed dough or as a component of one or more dough components.

The term "effective amount" herein means an amount of the added enzyme which is sufficient to effect, under dough conditions or degumming conditions, detectable hydrolysis of one or more glycolipids and one or more phospholipids present in the dough, whilst the added enzyme does not affect, or does not significantly affect, triglyceride and/or 1-monoglyceride levels. More specifically, the term may relate to an amount of the added enzyme which does not only result in detectable hydrolysis of a glycolipid and phospholipid, whilst not substantially affecting the level of triglycerides and/or 1-monoglycerides, but which, in addition, results in the formation of enzymatic end products by hydrolysis of glycolipids and phospholipids, or the lack of formation of enzymatic end products by no, or substantially no, activity on triglycerides and/or 1-monoglycerides, at a level which results in improved properties of the dough or if the dough is baked, an improved quality of the baked product, such as enhanced bread volume, enhanced softness or improved crumb structure or the removal of polar lipids from an edible oil.

The terms "substantially incapable of hydrolysing a triglyceride and/or a 1-monoglyceride" and "having substantially no hydrolytic activity towards a triglyceride and/or a 1-monoglyceride" as used herein mean that the enzyme hydrolyses a triglyceride and/or a 1-monoglyceride only to an insignificant and/or undetectable degree.

Advantageously, at least one of the triglyceride, the 1-monoglyceride, the glycolipid and the phospholipid in the dough is a naturally occurring lipid component occurring in flour used for the dough.

Suitably, the phospholipid is phosphatidylcholine (PC) and/or the glycolipid is digalactosyldiglyceride (DGDG).

When it is the case that a polar lipid is added, suitably the polar Lipid may be a phospholipid, such as one or more selected from the group consisting of phosphotidylinositol (PI), phosphatidylglycerol (PG), phosphatidylcholine (PC) and phosphatidylethanolamine (PE).

Preferably, the dough is a yeast leavened dough. Although, it is preferred to use the method of the present invention for the manufacture of yeast leavened bread products such as bread loaves, rolls or toast bread, the use of the method for any other type of dough and dough based products such as noodle and pasta products and cakes, the quality of which can be improved by the addition of the enzyme according to the present invention, is also contemplated.

Preferably, the enzyme is added in an amount which is in the range of 0.1 to 1000 units enzyme/kg flour. More preferably, the enzyme is added in an amount which is in the range of 1 to 100 units enzyme/kg flour.

Preferably, when the dough is a bread dough, the method comprises as a further step that the dough is baked to obtain a baked product. One particularly desired property of baked bread products is a high specific volume as defined in the examples. Accordingly, the addition of the enzyme of the invention preferably results in an increase of the specific volume of the baked product that is at least 10%, relative to a baked product made under identical conditions except that the enzyme is not added. More preferably, the increase of the specific volume is at least 20% such as at least 30%, e.g. at least 40%. Alternatively, the dough is a dough selected from the group consisting of a pasta dough, a noodle dough, and a cake dough or batter.

Preferably, the enzyme is added in an amount that results in an increase of the specific volume of the baked product that is at least 10%, relative to a baked product made under identical conditions except that the enzyme is not added.

The addition of the enzyme of the invention preferably results in an increase in the gluten index in the dough of at least 5%, relative to a dough without addition of the enzyme, the gluten index being determined by means of a Glutomatic 2200 apparatus.

The gluten index may be measured by means of a Glutomatic 2200 from Perten Instruments (Sweden) using the method detailed below: immediately after proofing, 15 g of dough should be scaled and placed in the Glutamatic 2200 and washed with 500 ml 2% NaCl solution for 10 min. The washed dough should then be transferred to a Gluten Index Centrifuge 2015 and the two gluten fractions should be scaled and the gluten index calculated according to the following equation:

$$\text{Gluten Index} = (\text{weight of gluten remaining in the sieve} \times 100)/\text{total weight of gluten.}$$

It has been found that the enzyme of the invention may be particularly active against certain glycolipids such as for example galactolipids including digalactodiglyceride (DGDG) which is converted into digalactomonoglyceride (DGMG) that is an effective surfactant. Preferably, at least 25% of the glycolipid initially present in the dough is hydrolysed and preferably at least 35% of the glycolipid is hydrolysed, more preferably at least 50%, at least 60% or at least 75% thereof.

Alternatively or in addition thereto, it has been found that the enzyme of the invention may be active against certain phospholipids which are converted into lysophospholipids. Preferably at least 25% of the phospholipid initially present in the dough is hydrolysed and preferably at least 35% of the phospholipid is hydrolysed, more preferably at least 50%, at least 60% or at least 75% thereof.

The activity of a lipase on triglyceride may depend on the pH of the substrate. Preferably, the enzyme has hydrolytic activity against a phospholipid and a glycolipid but no, or substantially no, hydrolytic activity against a triglyceride and/or a 1-monoglyceride in the pH range of 4.5-6.5.

Preferably, the enzyme as defined herein is incapable of hydrolysing a triglyceride and/or a 1-monoglyceride.

Preferably, the enzyme is incapable, or substantially incapable, of hydrolysing both a triglyceride and a 1-monoglyceride. Preferably the enzyme is incapable of hydrolysing both a triglyceride and a 1-monoglyceride. Alternatively, the enzyme may be capable of hydrolysing a triglyceride and a diglyceride, but be incapable, or substantially incapable, of hydrolysing a 1-monoglyceride. Suitably, the enzyme is incapable of hydrolysing a 1-monoglyceride.

It is known in the art that enzymes other than lipases may contribute to improved dough properties and quality of baked products. It is within the scope of the invention that, in addition to the enzyme of the invention, at least one further enzyme may be added to the dough or may be present in the dough improving composition. Such further enzymes include starch degrading enzymes such as endo- or exoamylases, pullulanases, starch degrading enzymes, debranching enzymes, hemicellulases including xylanases, cellulases, lipoxygenases and oxidoreductases, e.g. glucose oxidase, phospholipases and hexose oxidase.

Preferably, the further dough component in the composition, when one is present, is selected from the group consisting of cereal flour, yeast, a chemical leavening agent, a dough strengthening agent, an emulsifier, a sugar, an acylglycerol, a phospholipid, a glycolipid and a salt.

Suitably, the dough can be a fresh dough, optionally packed in a controlled atmosphere. The dough may be frozen.

Suitably, one or more enzymes according to the present invention may be added to the dough and/or be present in the dough improving composition and/or be added to the edible oil. Suitably, two or more, three or more, or four or more, enzymes according to the present invention may be added to the dough and/or be present in the dough improving composition and/or be added to the edible oil.

Preferably, the method of selecting enzymes according to the present invention may comprise screening the activity of enzymes on agar plates each containing either galactolipids, phospholipids, triglycerides or 1-monoglycerides as the substrate. Enzymes which are active towards phospholipids and glycolipids but which have no, or substantially no, activity towards triglycerides and/or 1-monoglycerides are selected.

Suitably, step (a) and/or (b) of the method of selecting an enzyme according to the present invention is carried out at a pH of 4.5-6.5.

Preferably, the enzyme tested by the method of selecting an enzyme according to the present invention is a lipase (E.C. 3.1.1.3) or a lipid acyl hydrolase (E.C. 3.1.1.26).

Preferably, in the method of preparing or developing an enzyme according to the present invention the insertion, deletion or substitution of at least one amino acid is in the lid region and/or near the active site and/or at the C-terminal of the amino acid sequence.

Preferably, the lid region is deleted.

Suitable enzymes may be prepared by modifying lipases (B.C. 3.1.1.3) and lipolytic acyl hydrolases (E.C. 3.1.1.26) to produce enzymes which are active towards phospholipids and glycolipids but which have no, or substantially no, activity towards triglycerides and/or 1-monoglycerides.

Suitable amino acid substitutions include substitutions of amino acids in or near the active site which change the hydrophilic properties around the active site. By way of example only, the amino acid substitutions may increase the number of polar amino acids in or near the active site.

Preferably, an enzyme is prepared in accordance with the present invention, which enzyme is capable of hydrolysing a glycolipid and a phospholipid and wherein said enzyme is incapable, or substantially incapable, of hydrolysing a triglyceride and/or a 1-monoglyceride in the pH range 4.5-6.5.

Suitably, the enzyme according to the present invention may have a greater activity towards glycolipids as compared with phospholipids. Suitably, the ratio of the % of hydrolysis of the initial glycolipids (i.e. DGDG) in the dough: the % hydrolysis of the initial phospholipids (i.e. phophatidylcholin) in the dough may be more than 10:1, for example, such as more than 15:1, more than 20:1, more than 30:1, or more than 40:1.

Alternatively, the enzyme according to the present invention may have a greater activity towards phospholipids as compared with glycolipids. For example, the ratio of the % of hydrolysis of the initial glycolipids (i.e. DGDG) in the dough: the % hydrolysis of the initial phospholipids (i.e. phophatidylcholin) in the dough may be more than 1:3, such as more than 1:5, more than 1:8, more than 1:10 or more than 1:15 for example.

Most cereal flours contain nonpolar lipids including triglycerides and polar lipids including phospholipids and glycolipids. The polar lipids can serve as substrates for the enzyme of the invention. Accordingly, in one embodiment of the method, at least one of the glycolipids, such as a galactolipid, including digalactosyldiglyceride (DGDG), and one of the phospholipids, such as phosphatidylcholine (PC), is a naturally occurring (or endogenous) lipid component occurring in the flour used for the dough.

However, flour dough may not contain sufficient amounts of these lipid substrates for the enzyme of the invention. It is therefore within the scope of the invention to supplement the dough with at least one of a glycolipid and a phospholipid to provide sufficient substrates for the enzyme. It will be appreciated that the expression "sufficient substrate" implies that neither of these lipid substrates is limiting for obtaining a dough improving or baked product improving effect as described above.

In addition or alternatively thereto, a supplementary nonpolar lipid such as an acylglycerol may be added. In accordance with the invention a variety of such lipids can be used such as e.g. vegetable oils, vegetable fats, animal oils, animal fats, such as for example butterfat, and shortening. In this connection, a particularly useful lipid is an oil or a fat derived from cereals such as oat oil. Oat oil typically contains, in addition to triglycerides, 5-25% phospholipids and 5-12% glycolipids. Oat oil can be fractionated to yield fractions having a high content of polar lipids (E. G. Hammond in Lipid in Cereal Technology edited by P. J. Barnes, Academic Press).

It is thus one aspect of the method of the invention that one or more phospholipids can be added to the dough. In this connection, useful phospholipids include phosphatidylinositol (PI), phosphatidylglycerol (PG), phosphatidylcholine (PC), lecithin and phosphatidylethanolamine (PE).

At least one of the triglyceride, the 1-monoglyceride, the glycolipid and the phospholipid may be added to the dough.

Surprisingly it has been found that the addition of an enzyme capable of hydrolysing a glycolipid and a phospholipid, wherein said enzyme is incapable, or substantially incapable, of hydrolysing a triglyceride and/or a 1-monoglyceride together with a glycolipid, in particular digalactosyldiglyceride (DGDG), results in improved bread volume and/or crumb structure. The improvements observed with the enzyme plus the glycolipid are even greater than the improvements observed with the enzyme alone. Thus, suitably, an enzyme having the specific properties defined herein may be used in combination with a glycolipid.

Edible oils, such as vegetable oils, for example soyabean oil or rapeseed oil, typically comprise triglycerides with a lower amount of polar lipids, such as phospholipids and glycolipids. It is often desired to remove the polar lipids from the vegetable oil in order to provide a clear, high quality oil product. The process of removing the polar lipids is often referred to as degumming. Thus, in accordance with the fifteenth apsect of the present invention the edible oil, for example a vegetable oil, may be degummed by use of an enzyme according to the present invention. Degumming is the first step of the edible oil refining process that removes the polar lipids, such as phospholipids, from the crude oil. Normally degumming is done by water or a wet process. For example, the phosphatides are converted to water-soluble lyso-phosphatides by an enzymatic catalysed hydrolysis, the water soluble lyso-phosphatides are then separated from the oil by centrifugation. The residual phosphorous content in the enzymatic degummed oil can be as low as 2 ppm phosphorous.

Preferably, the edible oil according to the fourteenth and fifteenth aspects of the present invention is a vegetable oil.

ADVANTAGES OF THE PRESENT INVENTION

An advantage of the present invention is that the enzyme of the present invention, which is active against glycolipids and phospholipids, but which is incapable, or substantially incapable, of hydrolysing triglycerides and/or 1-monoglycerides, when used in a dough, produces poly-unsaturated fatty acids, because the endogenous wheat glycolipids and phospholipids contain high levels (>70%) of linoleic acid (C18:2) and linolenic acid (C18:3). These fatty acids are substrates for lipoxygenase and contribute to increased gluten strength and a whiter crumb.

A further or alternative advantage of the present invention is that endogenous polar lipids can be modified without the production of excess fatty acids. Thus, the dough is prevented from becoming too stiff and/or resultant bread volume can be increased and/or the production of off-flavours can be reduced and/or the negative effects on yeast activity can be alleviated or overcome. A yet further or alternative advantage of the present invention is that shortening, oil or milk fat added to the dough is not hydrolysed.

DETAILED DESCRIPTION OF THE PRESENT INVENTION

Enzymes According to the Present Invention

The enzyme having the properties as defined herein may be derived from a variety of sources including plants, animals and microorganisms such as bacterial and fungal species including yeast species. The enzyme of the invention may be derived from an organism that naturally produces the enzyme or it may be produced recombinantly by transforming an appropriate host cell with a gene coding for the enzyme. The enzyme can be an enzyme that comprises in itself active sites for all of its enzyme activities, but it is also possible to construct hybrid enzymes having the enzyme activities as defined herein by synthesis or by using recombinant DNA technology.

Alternatively, an enzyme which does not, initially at least, have the specific properties as defined herein can be modified, for example by altering the amino acid sequence thereof, in order to provide an enzyme having the properties as defined herein and having the desired substrate specificity. It is known in the art to modify enzymes by random mutagenesis (U.S. Pat. No. 4,814,331, WO 93/01285 and WO 95/22615) and to modify lipolytic enzymes by site-specific mutagenesis (WO 97/04079) to obtain improved performance thereof. The generally used concept has been to insert, delete or substitute amino acids within the structural part of the amino acid chain of a lipolytic enzyme in question. A suitable enzyme for modification is one that can hydrolyse ester bonds. Such enzymes include, for example, lipases, such as triacylglycerol lipase (E.C. 3.1.1.3), lipo-protein lipase (E.C. 3.1.1.34), monoglyceride lipase (E.C. 3.1.1.23), lysophospholipase, ferulic acid esterase and esterase (E.C. 3.1.1.1, E.C. 3.1.1.2) and lipolytic acyl hydrolases (E.C. 3.1.1.26) and phosphatidylinositol deacylase (E.C. 3.1.1.52).

Suitable enzymes for modification may be derived from a variety of sources including plants, animals and microorganisms, such as bacterial and fungal species including yeast species. Examples of suitable enzymes for modification are the Pseudomonas lipases, for example from P. cepacia (U.S. Pat. No. 5,290,694), P. glumae (Frenken N et al (1992) Appl. Envir. Microbiol. 58 3787-3791), P. pseudoalcaligenes (EP 0 334 462) or Pseudomonas sp. Strain SD 705 (WO95/06720, EP 0 721 981, WO 96/27002, EP 0 812 910). Alternatively, suitable enzymes for modification may be for example fungal lipolytic enzymes, such as lipolytic enzymes of the Humicola family and the Zygomycetes family and fungal cutinases. The Humicola family of lipolytic enzymes consists of the lipase from H. lanuginosa strain DSM 4109 and lipases having more than 50% homology with this lipase. The lipase from H. lanuginosa (synonym Thermomyces lanuginosus) is described in EP 0 258 068 and EP 0 305 216, and has the amino acid sequence shown in positions 1-269 of SEQ ID NO. 2 of U.S. Pat. No. 5,869,438.

Withers-Martinez et al (Structure 1996, 4:1363-1374) studied a guinea pig pancreatic lipase-related protein 2 (GPLRP2) which has activity on galactolipids and phospholipids and reduced activity on triglyceride. The crystal structure of this enzyme is shown and compared with a human pancreas lipase (HPL) with only activity on triglyceride and a chimeric mutant of lipase-related protein 2 (GPLRP2) consisting of the catalytic domain of GPLRP2 and the C-terminal domain of HPL (GPLRP2/HPL). The mutant GPLRP2/HPL has activity against phospholipids and galactolipids, but with further reduced activity on triglyceride as compared with the GPLRP2 enzyme. Also hornet venom (PLA1) was analyzed for comparison. Withers-Martinez et al (Structure 1996 Nov. 15; 4(11): 1363-74) studied the loops located above the active site of the guinea pig pancreatic lipase-related protein 2, human pancreatic lipase and a phospholipase A1 from hornet venom and found a relation between loop configuration and activity to triglyceride and phospholipids.

In GPLRP2 the lid domain is reduced in size compared to HPL, and only the β9 loop is conserved and therefore a less hydrophobic surface around the active site is observed. This may explain the reduced activity on triglyceride of GPLRP2 and GPLRP2/HPL compared to HPL.

Merely by way of example, a variant lipase with no activity on monoglyceride may be obtained by substitution of specific amino acids in or around the catalytic site of a lipase. For example the lipase from Aspergillus tubingensis which has the amino acid sequence as shown in SEQ ID No. 3 and as taught in European Patent Publication No. 0 977 869, and which is encoded by the nucleotide sequence shown in SEQ ID No. 4, may be altered to provide such a variant lipase for use in accordance with the present invention.

The catalytic triad of SEQ ID No. 3 is Serine 173 (Ser173), Aspartic acid 228 (Asp228) and Histidine 285 (His285). Suitably, one or more of these amino acids of the catalytic triad may be substituted to change the hydrophilic properties of the catalytic triad.

One or more of the following amino acids in or around the catalytic site of SEQ ID No. 3 may be substituted to change the hydrophilic properties around the active site: Phe107-Phe123; Gly171-Gly175; Tyr198-Ile203; Thr224-Gly239; Ser270-Leu297.

For example, the procedure for mutating a "parent" lipase to provide a variant lipase with altered substrate activity in accordance with the present invention may include the following steps.

A. Expression Vector Construction

Figure 11:
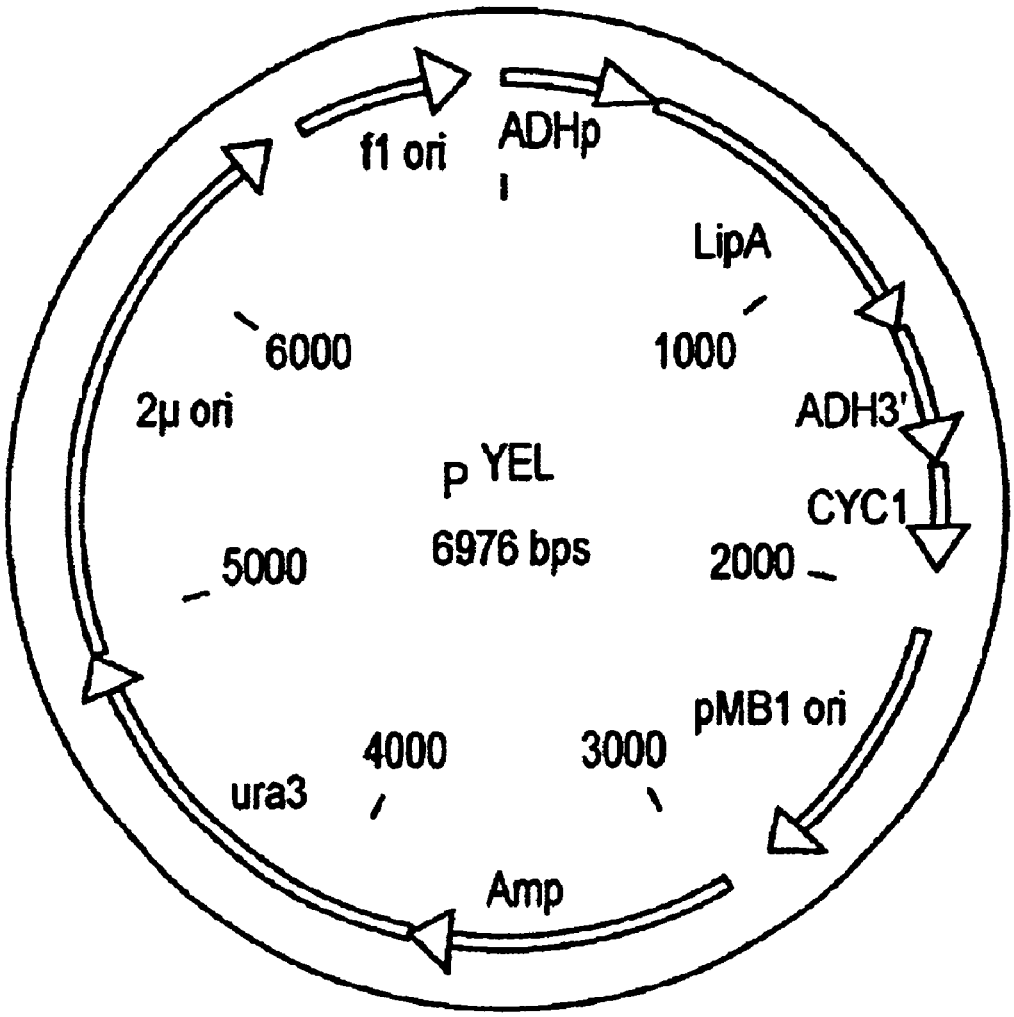

A vector, for example pYEL, may be constructed by replacing the inducible promoter, $Gal1_p$, with the constitutive promoter, $ADH_p$, and a lipase gene (for example the lipase gene from Aspergillus tubigenisis as taught in EP 0 977 869) may be incorporated by in vivo recombination in S. cerevisiae. FIG. 11 shows such an expression vector derived from pYES2

B. Random Mutagenesis by Error Prone PCR (EP-PCR)

Random mutagenesis libraries may then be created, for example, using two EP-PCR procedures; GeneMorph™ PCR Mutagenesis Kit and Diversify™ PCR Random Mutagenesis Kit, henceforward referred to as Genemorph and Diveresify, respectively.

Mutation frequency may be optimised in order to obtain 1-2 amino acid substitutions per lipase gene, for example per LipA gene. Optimisation of mutation frequency may be performed by varying initial amounts of template DNA (~0.65-40 ng) in Genemorph EP-PCR procedure and by varying concentrations of $MnSO_4$ (0-640 μM) and dGTP (40-120 μM) in Diversify EP-PCR procedure. The optimised EP-PCR procedures may contain contain: 0.65 ng DNA template, 2.5 U Mutazyme DNA Polymerase, 125 ng of each primer, 1×Mutazyme reaction buffer and 200 μM dNTP mix in the Genemorph EP-PCR procedure. In Diversify EP-PCR procedure 1 ng DNA template, 2 U Titanium™ Taq DNA Polymerase, 10 μM of each primer, 3.5 mM $MgCl_2$, 480 μM $MnSO_4$ 200 μM dNTP mix and 40 μM dGTP were applied. Both EP-PCR procedures were executed in a total volume of 50 μL.

Primers designed for both EP-PCR procedures are shown in the table below. The primer JOM1 additionally introduces three A's (underscored) upstream of the start codon.

| Primer | Nucleotide sequence | $T_m$ [° C.] | Primer site [bp] | |
|---|---|---|---|---|
| JOM1 | 5'CAAGCTATACCAAGCATA CAATCAACTCCAAAATGTT CTCTGGACGGTTTG3' | 77.6 | 380-398 ($ADH_p$)→ 1-20 (LipA) | SEQ ID No. 5 |

-continued

| Primer | Nucleotide sequence | $T_m$ [° C.] | Primer site [bp] | |
|---|---|---|---|---|
| JOM2 | 5'CAAACCTCTGGCGAAGAA GTCCAAAGCTG3' | 69.3 | 400→428 (ADH3') | SEQ ID No. 6 |

EP-PCR may be performed using a programmable thermal cycler with following conditions; GeneMorph™ PCR Mutagenesis Kit: 94° C. for 30 seconds, followed by 30 cycles of 94° C. for 30 seconds, 55° C. for 30 seconds and 72° C. for 2 minutes. Finally an additional extension of 10 minutes at 72° C. was applied. Diversify™ PCR Random Mutagenesis Kit: 94° C. for 30 seconds, followed by 25 cycles of 94° C. for 30 seconds and 68° C. for 1 minute.

C. Transformation and Expression

Transformed and competent cells may be prepared by a modification of the transformation procedure described in the pYES2 protocol (Catalog no. V825-20, Invitrogen, CA, USA), for example. A single colony of Saccharomyces cerevisiae CEN.PK113-5D may be inoculated in 20 mL YPD and grown overnight at 30° C. with shaking at 200 RPM. The overnight culture may be diluted with YPD to an $OD_{600}$ of 0.2-0.3 and incubated for an additional three hours at 30° C. and 200 RPM. Cells may be harvested by centrifugation at 4750 g and 20° C. for 5 minutes. The pellet may be washed by resuspension in 1 mL 1×TrisEDTA (1×TE), pH 8.0, and centrifuged for 5 minutes at 10000 g. Cells were made competent by adding 0.5 mL of 1×TE and 100 mM Lithium Acetate, pH 7.5.

Transformation may be performed by gently mixing 100 μg DNA with 50 μL competent Saccharomyces cerevisiae cells, 5 μL Yeastmaker Carrier DNA and 300 μL of 100 mM Lithium Acetate, 40% Polethylene glycol 3350 and 1×TE. The mixturemay be incubated at 30° C. with shaking at 1000 RPM for 30 minutes followed by incubation at 42° C. for 15 minutes. Afterwards cells may be transferred to ice and then pelleted at 11300 g for 5 seconds. The pellet may be resuspended in 1 mL YPD and incubated for 45 minutes at 30° C. and 200 RPM. A suspension volume of 150 μL was transferred to plates containing SC-ura and incubated for 3 days at 30° C. Transformation into competent Saccharomyces cerevisiae cells was furthermore utilised for cloning purposes using in vivo recombination, in which 100 ng of the lipase (for example LipA) or variants thereof may be co-transformed with 50 ng of BamHI linearised pYEA.

D. DNA Isolation

Plasmid DNA from Escherichia coli may be isolated by alkaline lysis using High Pure Plasmid Isolation Kit.

Plasmid DNA from Saccharomyces cerevisiae may be isolated as follows: cells may be pelleted by centrifugation at 1100 g for 15 minutes and re-suspended in 1 mL STET and 1.5 mL glass beads (425-600 microns). Additionally a volume of 1 mL STET was added and the mixture was incubated at 100° C. for 5 minutes. The solution may then be centrifuged for 15 minutes at 6500 g and supernatant may be transferred to an eppendorf tube, which was centrifuged for an additional 15 minutes at 27000 g. DNA may be extracted and purified from the supernatant using Qiagen-tip 20 from Plasmid Mini Purification Kit.

E. DNA Sequencing

Lipase (for example LipA) variants may be sequenced according to the dideoxy chain terminator procedure [Sanger et al., 1977]. Plasmid DNA for sequencing may be prepared using a modification of Plasmid Mini Purification Kit. Hereby a standard alkaline lysis may be performed instead of using Qiagen-tip 20 a. When using PCR amplified DNA for sequencing, DNA was isolated by Wizard® PCR Preps DNA purification System.

The sequencing reaction may be performed using ABI Prism® BigDye™ Terminators v3.0 Cycle Sequencing Kit (Danisco Biotechnology) or ABI Prism™ dRhodamine Terminator Cycle Sequencing Ready Reaction Kit (AAU) with DNA template and primer concentrations of 500 ng and 3.2 pmol, respectively. The sequencing reactions may be carried out using a programmable thermal cycler with following conditions: 25 cycles of 96° C. for 30 seconds, 50° C. for 15 seconds and 60° C. for 4 minutes. Purification of PCR products may be performed by ethanol precipitation and the pellet may be resuspended in 12 μL HIDI formamide (Danisco Biotechnology) or 12 μL template suppression reagent (AAU) and may be transferred to a Genetic Analyser sample tube with septa. Samples may be ran on an ABI Prism® 3100 Genetic Analyser (Danisco Biotechnology) or ABI Prism® 310 Genetic Analyser (AAU). Suitable primers for sequencing a variant LipA are presented in the table below. These primers anneal internally in Lip A.

| Primer | Nucleotide sequence | Primer site [bp] | $T_m$ [° C.] |
|---|---|---|---|
| JOM3 | 5'GCTCGTGGTCGCCTTCCGGGG 3' (SEQ ID No. 7) | 306-326 (LipA) | 68.2 |
| JOM4 | 5'GCCGGTGCAGAGGTCGTCG 3' (SEQ ID No. 8) | 399-381 (LipA) | 58.1 |
| JOM5 | 5'CCTCGAATCGGAAACTATGCGC 3' (SEQ ID No. 9) | 601-622 (LipA) | 61.6 |
| JOM13 | 5'TGTCACGGCGTCGGATATCG 3' (SEQ ID No. 10) | 768-787 (LipA) | 78 |
| JOM14 | 5'CTCATCCAACGTGGAAGTCG 3' (SEQ ID No. 11) | 108-89 (LipA) | 77 |

F. Screening for Lipase (Suitably Lipase 3) Variants: Altered Substrate Specificity Variants displaying DGDG and phospholipase activity, but no triglyceride activity may be identified using, for example, a preliminary high throughput plate screen followed by a quantitative screen, in which the enhancement is verified and quantified.

G. Production and Purification of Improved Variants

A single colony of selected variants may be inoculated in 50 mL of SC-ura medium and incubated at 30° C. and 250 rpm for two days, after which 25 mL may be transferred to 500 mL YPD medium and incubated for additionally two days at 30° C. and 200 rpm. The lipase produced may be separated from the culture by centrifugation for 15 min. The supernatant may be stored at −18° C. until further use.

Hydrophobic Interaction Chromatography

A volume of 250 mL supernatant may be equilibrated with $(NH_4)_2SO_4$ to obtain a final concentration of 1.0 M $(NH_4)_2SO_4$. The suspension was injected onto a SOURCE15PHE column containing phenyl hydrophobic ligands coupled to a 15 μm monodispersed rigid polystyrene/divinylbenzene matrix. The column may be packed to a final bed volume of 5.1 mL. Elution may be performed with 20 mM NaAc buffer pH 5.5 and a linear decreasing gradient of 1.0 M-0 M $(NH_4)_2SO_4$ at a rate of 5 mL/min for 20 min.

Identification of fractions containing lipase (for example lipase 3) and variants thereof inaccordance with the present invention may be performed by applying 15 μL of each fraction into wells on a plate containing suitable substrates to screen for phopsholipase activity, galactolipase activity and triglyceride hyrolyses.

Desalting

Selected fractions may be desalted using PD-10 desalting columns containing a Sephadex G-25 matrix packed to a final bed volume of 8.3 mL. The column may be pre-equilibrated with 20 mM TEA buffer pH 7.3, after which a sample volume of 2.5 mL was applied. Elution may be performed by applying 3.5 mL of 20 mM TEA buffer pH 7.3.

Anion Exchange Chromatography

Selected fractions may be injected onto a SOURCE15Q column containing quaternary ammonium ligands coupled to a 15 μm monodispersed rigid polystyrene/divinylbenzene matrix. The column may be packed to a final bed volume of 5.1 mL. Elution may be performed with 20 mM TEA buffer pH 7.3 and a linear increasing gradient of 0 M-1.0 M NaCl at a rate of 2 mL/min for 20 min.

H. Characterisation of Improved Variants

SDS-PAGE/Native Gel

Proteins may be separated according to size by SDS-PAGE using 1×running buffer, a 12% separating gel and 4% stacking gel prepared according to Laemmli (1970).

Equivalent amounts of sample and SDS sample buffer, containing 2-mercaptoethanol, may be incubated at 95° C. for 5 min. As standard a low range molecular weight marker was employed containing 0.64 μg Phosphorylase b, 0.83 μg Bovine serum albumin, 1.47 μg Ovalbumin, 0.83 μg Carbonic anhydrase, 0.88 μg Soybean trypsin inhibitor and 1.21 μg α-lactalbumin. Protein bands were visualised using Coomassie® G250 Stain.

For Native PAGE: Proteins may be separated according to mobility by native PAGE, in which no SDS was applied.

Lipases with only activity against galactolipids and phospholipids have not previously been used for baking. These types of lipases are rarely mentioned in the literature. However, Matos A. R. et al (FEBS Lett 2001 Mar. 2; 491(3): 188-92) isolated a 43 KDa protein from drought-stressed cowpea which was expressed in a baculovirus system. This enzyme showed preferentially galactolipid acyl hydrolase activity and some phospholipid activity but no activity on triacylglycerol (triglyceride). The amino acid sequence of this enzyme is shown in SEQ ID No. 1 and the nucleotide sequence encoding this enzyme is shown in SEQ ID No. 2. These types of enzyme are different from normal lipases (EC. 3.1.1.3) and the term lipolytic acyl hydrolase (LAH) (E.C. 3.1.1.26) is usually applied to these enzymes, which enzymes have only been described in the plant kingdom. The galactolipid acyl hydrolase described in Matos et al is suitable for use in accordance with the present invention.

The enzyme according to the present invention may be either a lipase (E.C. 3.1.1.3) or a lipolytic acyl hydrolase (E.C. 3.1.1.26), as long as it possesses the specified properties.

Sahsah et al (Biochem Biophys Acta 1994 Nov. 17;1215 (1-2):66-73) isolated a lipolytic acyl hydrolase from soluble cowpea leaf extract. The hydrolytic activity of this enzyme on different substrates showed the following relative activity digalactosyldiglyceride>monogalactosyldiglyceride> phosphatidylcholine>phosphatid ylglycerol. The enzyme had no activity on triacylglycerol (triglyceride). The enzyme taught in Sahsah et al is suitable for use in accordance with the present invention.

O'Sullivan et al (J. Plant Physiol. Vol. 131, pp 393-404 1987) disclosed a membrane-bound galactolipase associated with thylakoids of wheat leaves.

As the examples above illustrate lipases or lipolytic acyl hydrolases with activity on phospholipids and galactolipids alone, although apparently rare, exist in the nature and may be used in accordance with the present invention. In addition or alternatively other means of making a lipase with activity against phospholipids and galactolipids but no activity against triglycerides and/or 1-monoglycerides exist.

As mentioned above, Withers-Martinez (Structure 1996, 4:1363-1374) showed that a guinea pig lipase-related protein 2 (GPLRP 2) had activity on phospholipids and galactolipids and reduced activity on triglyceride. It is also indicated that the hydrophilicity around the active site can control the activity on triglyceride. This opens up the possibility of substitutions of amino acids in or near the active site which would further reduce the triglyceride activity by changing the hydrophilic properties around the active site.

It is well known that the activity of lipases can be altered by changing specific amino acids in the enzyme. Cordle et al (J. Lipid Res. 1998 September 39 (9): 1759-67) substituted tyrosine with the more polar aspartic acid and obtained a reduced activity on long chain fatty acids.

Carriere et al (Biochemistry 1997 Jan. 7 36(1): 239-48) removed the lid of a human pancreatic lipase in order to eliminate interfacial activation and found that its specific activity toward triglycerides was dramatically reduced. This article also reports that the C-terminal of a human pancreatic lipase is important for the interfacial stability.

A preferred lipase for baking with activity on phospholipids and galactolipids but with no activity on triglyceride can also be obtained by modifying the pH optimum for the triglyceride activity. Under normal conditions pH in a dough is in the range of 4.5-6.5. Ching T. Hou (Journal of Industrial Microbiology, 13 (1994) 242-248) screened a number of different lipases and found a number of lipases having triglyceride activity at pH 7.5 but no activity at pH 5.5.

By selecting a lipase with no activity at say pH 5.5 and modifying the area around the active site by site-directed or localized random mutagenesis to alter the hydrophilic properties of the surface around the active site and modifying the lid by site-directed or localised random mutagenesis, it is possible to obtain a lipase with activity on phospholipids and galactolipids and with the remaining triglyceride activity being active at a pH 7.5 or above, but with no activity at pH 6.5 or below, such as at pH 5.5.

Lipases can have different types of specificity (Inform Vol. 8, No. 6 640-650). The fatty acyl specificity of a lipase will have an impact on the type of fatty acid produced. Some lipases are very specific to unsaturated fatty acids, which in a dough system is preferable, as the polyunsaturated fatty acid is a substrate for endogenous or added lipoxygenase. Preferably, the enzyme according to the present invention preferentially hydrolyses unsaturated fatty acids. Suitably, in the method of preparing or developing an enzyme according to the present invention the insertion, deletion or substitution alters the fatty acyl specificity of the enzyme, such that the enzyme preferentially produces polyunsaturated fatty acids in the lipid moiety.

Suitable examples of enzymes having hydrolytic activity towards a phospholipid and a glycolipid and having no, or substantially no, hydrolytic activity towards a triglyceride and/or a 1-monoglyceride are presented in the section entitled Examples hereinbelow.

Cloning a Nucleotide Sequence Encoding an Enzyme According to the Present Invention A nucleotide sequence encoding either an enzyme which has the specific properties as defined herein or an enzyme which is suitable for modification may be isolated from any cell or organism producing said enzyme. Various methods are well known within the art for the isolation of nucleotide sequences.

For example, a genomic DNA and/or cDNA library may be constructed using chromosomal DNA or messenger RNA from the organism producing the enzyme. If the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar containing a substrate for enzyme (i.e. phospholipids or galactolipids), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al (1981) Tetrahedron Letters 22, p 1859-1869, or the method described by Matthes et al (1984) EMBO J. 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin, or mixed genomic and CDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al (Science (1988) 239, pp 487-491).

Nucleotide Sequences

The present invention also encompasses nucleotide sequences encoding enzymes having the specific properties as defined herein. The term "nucleotide sequence" as used herein refers to an oligonucleotide sequence or polynucleotide sequence, and variant, homologies, fragments and derivatives thereof (such as portions thereof). The nucleotide sequence may be of genomic or synthetic or recombinant origin, which may be double-stranded or single- stranded whether representing the sense or antisense strand.

The term "nucleotide sequence" in relation to the present invention includes genomic DNA, cDNA, synthetic DNA, and RNA. Preferably it means DNA, more preferably cDNA for the coding sequence of the present invention.

In a preferred embodiment, the nucleotide sequence per se encoding an enzyme having the specific properties as defined herein does not cover the native nucleotide sequence in its natural environment when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. Thus, the enzyme of the present invention can be expressed by a nucleotide sequence in its native organism but wherein the nucleotide sequence is not under the control of the promoter with which it is naturally associated within that organism.

Preferably the enzyme is not a native enzyme. In this regard, the term "native enzyme" means an entire enzyme that is in its native environment and when it has been expressed by its native nucleotide sequence.

Typically, the nucleotide sequence encoding enzymes having the specific properties as defined herein is prepared using recombinant DNA techniques (i.e. recombinant DNA). However, in an alternative embodiment of the invention, the nucleotide sequence could be synthesised, in whole or in part, using chemical methods well known in the art (see Caruthers M H et al (1980) Nuc Acids Res Symp Ser 215-23 and Horn T et al (1980) Nuc Acids Res Symp Ser 225-232).

Amino Acid Sequences

The present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

Suitably, the amino acid sequences may be obtained from the isolated enzymes taught herein by standard techniques.

One suitable method for determining amino acid sequences from isolated enzymes is as follows:

Purified enzyme may be freeze-dried and 100 μg of the freeze-dried material may be dissolved in 50 μl of a mixture of 8 M urea and 0.4 M ammonium hydrogen carbonate, pH 8.4. The dissolved protein may be denatured and reduced for 15 minutes at 500° C. following overlay with nitrogen and addition of 5 μl of 45 mM dithiothreitol. After cooling to room temperature, 5 μl of 100 mM iodoacetamide may be added for the cysteine residues to be derivatized for 15 minutes at room temperature in the dark under nitrogen.

135 μl of water and 5 μg of endoproteinase Lys-C in 5 H1 of water may be added to the above reaction mixture and the digestion may be carried out at 37° C. in nitrogen for 24 hours.

The resulting peptides may separated by reverse phase HPLC on a VYDAC C18 column (0.46×15 cm; 10 ym; The Separation Group, California, USA) using solvent A: 0.1 t TFA in water and solvent B: 0.1 k TFA in acetonitrile. Selected peptides may be re-chromatographed on a Develosil C18 column using the same solvent system, prior to N-terminal sequencing. Sequencing may be done using an Applied Biosystems 476A sequencer using pulsed liquid fast cycles according to the manufacturer's instructions (Applied Biosystems, California, USA).

Variants/Homologues/Derivatives

The present invention also encompasses the use of variants, homologues and derivatives of any amino acid sequence of an enzyme having the specific properties defined herein or of any nucleotide sequence encoding such an enzyme. Here, the term "homologue" means an entity having a certain homology with the subject amino acid sequences and the subject nucleotide sequences. Here, the term "homology" can be equated with "identity".

The variant, homologue and derivative amino acid sequence and/or nucleotide sequence should provide and/or encode an enzyme which retains the functional activity and/or enhances the activity of the enzyme.

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p387). Examples of other software than can perform sequence comparisons include, but are not limited to, the BLAST package (see Ausubel et al 1999 Short Protocols in Molecular Biology, $4^{th}$ Ed—Chapter 18), FASTA (Altschul et al 1990 J. Mol.

Biol. 403-410) and the GENEWORKS suite of comparison tools. Both BLAST and FASTA are available for offline and online searching (see Ausubel et al 1999, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P<br>I L V |
| | Polar-uncharged | C S T M<br>N Q |
| | Polar-charged | D E<br>K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid*, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid# and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell DC, Trends Biotechnol. (1995) 13(4), 132-134.

Nucleotide sequences encoding an enzyme having the specific properties defined herein may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences.

The present invention also encompasses the use of nucleotide sequences that are complementary to the sequences discussed herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other viral/bacterial, or cellular homologues particularly cellular homologues found in mammalian cells (e.g. rat, mouse, bovine and primate cells), may be obtained and such homologues and fragments thereof in general will be capable of selectively hybridising to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterised sequences. This may be useful where for example silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Hybridisation

The present invention also encompasses sequences that are complementary to the sequences of the present invention or sequences that are capable of hybridising either to the sequences of the present invention or to sequences that are complementary thereto.

The term "hybridisation" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridising to the sequences that are complementary to the subject sequences discussed herein, or any derivative, fragment or derivative thereof.

The term "variant" also encompasses sequences that are complementary to sequences that are capable of hybridising to the nucleotide sequences discussed herein.

Hybridisation conditions are based on the melting temperature (Tm) of the nucleotide binding complex, as taught in Berger and Kimmel (1987, Guide to Molecular Cloning Techniques, Methods in Enzymology, Vol. 152, Academic Press, San Diego Calif.), and confer a defined "stringency" as explained below.

Maximum stringency typically occurs at about Tm−5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridisation can be used to identify or detect identical nucleotide sequences while an intermediate (or low) stringency hybridisation can be used to identify or detect similar or related polynucleotide sequences.

Preferably, the term "variant" encompasses sequences that are complementary to sequences that are capable of hybridising under high stringency conditions or intermediate stringency conditions to nucleotide sequences encoding enzymes having the specific properties as defined herein.

More preferably, the term "variant" encompasses sequences that are complementary to sequences that are capable of hybridising under high stringent conditions (e.g. 65° C. and 0.1×SSC {1×SSC=0.15 M NaCl, 0.015 M Na-citrate pH 7.0}) to nucleotide sequences encoding enzymes having the specific properties as defined herein.

The present invention also relates to nucleotide sequences that can hybridise to the nucleotide sequences discussed herein (including complementary sequences of those discussed herein).

The present invention also relates to nucleotide sequences that are complementary to sequences that can hybridise to the nucleotide sequences discussed herein (including complementary sequences of those discussed herein).

Also included within the scope of the present invention are polynucleotide sequences that are capable of hybridising to the nucleotide sequences discussed herein under conditions of intermediate to maximal stringency.

In a preferred aspect, the present invention covers nucleotide sequences that can hybridise to the nucleotide sequences discussed herein, or the complement thereof, under stringent conditions (e.g. 50° C. and 0.2×SSC).

In a more preferred aspect, the present invention covers nucleotide sequences that can hybridise to the nucleotide sequences discussed herein, or the complement thereof, under high stringent conditions (e.g. 65° C. and 0.1×SSC).

Site-directed Mutagensis

Once an enzyme-encoding nucleotide sequence and/or amino acid sequence of the enzyme has been isolated, it may be desirable to mutate the sequence in order to prepare an enzyme having the desired properties of the present invention or to enhance the natural properties of the enzyme.

Mutations may be introduced using synthetic oligonucleotides. These oligonucleotides contain nucleotide sequences flanking the desired mutation sites.

A suitable method is disclosed in Morinaga et al (Biotechnology (1984) 2, p646-649), wherein a single-stranded gap of DNA, the enzyme-encoding sequence, is created in a vector carrying the enzyme gene. The synthetic nucleotide, bearing the desired mutation, is then annealed to a homologous portion of the single-stranded DNA. The remaining gap is then filled in with DNA polymerase I (Klenow fragment) and the construct is ligated using T4 ligase. Other suitable methods include the mega prima mutagenesis method of Sarkar G & Sommer S. S. (1990 BioTechniquesI 8, 404-407) and the QuickChange method of Papworth et al (1985 Nucleic. Acids Res. 13: 8765-8785).

U.S. Pat. No. 4,760,025 discloses the introduction of oligonucleotides encoding multiple mutations by performing minor alterations of the cassette. However, an even greater variety of mutations can be introduced at any one time by the above mentioned Morinaga method, because a multitude of oligonucleotides, of various lengths, can be introduced.

Another method of introducing mutations into enzyme-encoding nucleotide sequences is described in Nelson and Long (Analytical Biochemistry (1989), 180, p 147-151). This method involves the 3-step generation of a PCR fragment containing the desired mutation introduced by using a chemically synthesised DNA strand as one of the primers in the PCR reactions. From the PCR-generated fragment, a DNA fragment carrying the mutation may be isolated by cleavage with restriction endonucleases and reinserted into an expression plasmid.

Furthermore, Sierks et al (Protein Eng (1989) 2, 621-625 and Protein Eng (1990) 3, 193-198) describes site-directed mutagenesis in Aspergillus glucoamylase.

Suitably, a nucleotide sequence encoding either a lipase (E.C. 3.1.1.3) or a lipolytic acyl hydrolase (E.C. 3.1.1.26) may be subjected to site-directed mutagenesis in the lid region and/or near the active site and/or at the C-terminal of the amino acid sequence.

Preferably, the nucleotide sequence encoding either a lipase (E.C. 3.1.1.3) or a lipolytic acyl hydrolase (E.C. 3.1.1.26) may be subjected to site-directed mutagenesis near the active site to alter the hydrophilic properties of the surface around the active site.

Random Mutagenesis

Error prone PCR can be performed, for example by using the Diversify™ PCR Random Mutagenesis Kit from CLONTECH.

Localised Random Mutagenesis

A mutagenic primer (oligonucleotide) may be synthesised which corresponds to the part of the DNA sequence to be mutagenised except for the nucleotide(s) corresponding to amino acid codon(s) to be mutagenised. The primer will, in the 5' and 3' end, contain nucleotides corresponding to the sequence surrounding the sequence to be mutagenised. In the codons to be mutagenised different percentages of the four different nucleotides will be present at each position, giving the possibility for codons for different amino acids in the selected positions.

Subsequently, the resulting mutagenic primer may be used in a PCR reaction with a suitable opposite primer. The resulting PCR fragment may be cloned, perhaps after some additional modification, into a suitable vector, containing the rest of the coding region of the gene of interest.

Suitably, a nucleotide sequence encoding either a lipase (E.C. 3.1.1.3) or a lipolytic acyl hydrolase (E.C. 3.1.1.26) may be subjected to localised random mutagenesis in the lid region and/or near the active site and/or at the C-terminal of the amino acid sequence.

Preferably, the nucleotide sequence encoding either a lipase (E.C. 3.1.1.3) or a lipolytic acyl hydrolase (E.C. 3.1.1.26) may be subjected to localised random mutagenesis near the active site to alter the hydrophilic properties of the surface around the active site.

Expression of Enzymes

A nucleotide sequence encoding an enzyme having the specific properties as defined herein can be incorporated into a recombinant replicable vector. The vector may be used to replicate and express the nucleotide sequence, in enzyme form, in and/or from a compatible host cell. Expression may be controlled using control sequences which include promoters/enhancers and other expression regulation signals. Prokaryotic promoters and promoters functional in eukaryotic cells may be used. Tissue specific or stimuli specific promoters may be used. Chimeric promoters may also be used comprising sequence elements from two or more different promoters described above.

The enzyme produced by a host recombinant cell by expression of the nucleotide sequence may be secreted or may be contained intracellularly depending on the sequence and/or the vector used. The coding sequences can be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated in the genome of the organism. The term "incorporated" preferably covers stable incorporation into the genome.

Preferably, the vector of the present invention comprises a construct according to the present invention. Alternatively expressed, preferably a nucleotide sequence coding for an enzyme having the specific properties as defined herein is present in a vector and wherein the nucleotide sequence is operably linked to regulatory sequences such that the regulatory sequences are capable of providing the expression of the nucleotide sequence by a suitable host organism, i.e. the vector is an expression vector.

The vectors of the present invention may be transformed into a suitable host cell as described below to provide for expression of a polypeptide or enzyme having the specific properties as defined herein. Thus, in a further aspect the invention provides a process for preparing polypeptides for subsequent use according to the present invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The choice of vector will often depend on the host cell into which it is to be introduced.

The vectors may contain one or more selectable marker genes. The most suitable selection systems for industrial micro-organisms are those formed by the group of selection markers which do not require a mutation in the host organism. Suitable selection markers may be the dal genes from B. subtilis or B. licheniformis, or one which confers antibiotic resistance such as ampicillin, kanamycin, chloramphenicol or tetracyclin resistance. Alternative selection markers may be the Aspergillus selection markers such as amdS, argB, niaD and sC, or a marker giving rise to hygromycin resistance. Examples of other fungal selection markers are the genes for ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in filamentous fungi), the ampicillin resistance gene (E. coli), the neomycin resistance gene (Bacillus) and the E. coli uidA gene, coding for β-glucuronidase (GUS). Further suitable selection markers include the dal genes from B subtilis or B. licheniformis. Alternatively, the selection may be accomplished by co-transformation (as described in WO91/17243).

Vectors may be used in vitro, for example for the production of RNA or used to transfect or transform a host cell.

Thus, nucleotide sequences encoding enzymes having the specific properties as defined herein can be incorporated into a recombinant vector (typically a replicable vector), for example a cloning or expression vector. The vector may be used to replicate the nucleic acid in a compatible host cell. Thus in a further embodiment, the invention provides a method of making nucleotide sequences encoding enzymes having the specific properties as defined herein by introducing a nucleotide sequence encoding such an enzyme into a replicable vector, introducing the vector into a compatible host cell, and growing the host cell under conditions which bring about replication of the vector. The vector may be recovered from the host cell. Suitable host cells are described below in connection with expression vectors.

The procedures used to ligate a DNA construct of the invention encoding an enzyme which has the specific properties as defined herein, and the regulatory sequences, and to insert them into suitable vectors containing the information necessary for replication, are well known to persons skilled in the art (for instance see Sambrook et al Molecular Cloning: A laboratory Manual, $2^{nd}$ Ed. (1989)).

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, a nucleotide sequence encoding an enzyme having the specific properties as defined herein may be operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme having the specific properties as defined herein may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the enzyme having the specific properties as defined herein. In eukaryotes, polyadenylation sequences may be operably connected to the nucleotide sequence encoding the enzyme.

Preferably, the nucleotide sequence of the present invention may be operably linked to at least a promoter.

Aside from the promoter native to the gene encoding the nucleotide sequence encoding an enzyme having the specific properties as defined herein, other promoters may be used to direct expression of the enzyme. The promoter may be selected for its efficiency in directing the expression of the nucleotide sequence of the present invention in the desired expression host.

In another embodiment, a constitutive promoter may be selected to direct the expression of the desired nucleotide sequence. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters. Other examples of useful promoters for transcription in a fungal host are those derived from the gene encoding A. oryzae TAKA amylase, the TPI (triose phosphate isomerase) promoter from S. cerevisiae (Alber et al (1982) J. Mol. Appl. Genet. 1, p419-434), Rhizomucor miehei aspartic proteinase, A. niger neutral α-amylase, A. niger acid stable α-amylase, A. niger glucoamylase, Rhizomucor miehei lipase, A. oryzae alkaline protease, A oryzae triose phosphate isomerase or A. nidulans acetamidase.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes. Examples of other suitable promoters for directing the transcription of the nucleotide sequence especially in a bacterial host are the promoters of the lac operon of E. coli, the Streptomyces coelicolor agarase gene dagA promoters, the promoters of the Bacillus licheniformis α-amylase gene (amyL), the promoters of the Bacillus stearothermophilus maltogenic amylase gene (amyM), the promoters of the Bacillus amyloliquefaciens α-amylase (amyQ), the promoters of the Bacillus subtilis xylA and xylB genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat 1987 Gene 217, 217-225 and Dawson 1993 Plant Mol. Biol. 23: 97).

Constructs

The term "construct"—which is synonymous with terms such as "conjugate", "cassette" and "hybrid"—includes a nucleotide sequence encoding an enzyme having the specific properties as defined herein for use according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus Bacillus, such as Bacillus subtilis, or plants into which it has been transferred. Various markers exist which may be used, such as for example those encoding mannose-6-phosphate isomerase (especially for plants) or those markers that provide for antibiotic resistance—e.g. resistance to G418, hygromycin, bleomycin, kanamycin and gentamycin.

For some applications, preferably the construct comprises at least a nucleotide sequence encoding an enzyme having the specific properties as defined herein operably linked to a promoter.

Host Cells

The term "host cell"—in relation to the present invention includes any cell that comprises either a nucleotide sequence encoding an enzyme having the specific properties as defined herein or an expression vector as described above and which is used in the recombinant production of an enzyme having the specific properties as defined herein.

Thus, a further embodiment of the present invention provides host cells transformed or transfected with a nucleotide sequence that expresses an enzyme having the specific properties as defined herein. Preferably said nucleotide sequence is carried in a vector for the replication and expression of the nucleotide sequence. The cells will be chosen to be compatible with the said vector and may for example be prokaryotic (for example bacterial), fungal, yeast or plant cells.

The gram negative bacterium E. coli is widely used as a host for heterologous gene expression. However, large amounts of heterologous protein, tend to accumulate inside the cell. Subsequent purification of the desired protein from the bulk of E. coli intracellular proteins can sometimes be difficult.

In contrast to E. coli, Gram positive bacteria from the genus Bacillus, such as B. subtilis, B. licheniformis, B. lentus, B. brevis, B. stearothermophilus, B. alkalophilus, B. amyloliquefaciens, B. coagulans, B. circulans, B. lautus, B. megaterium, B. thuringiensis, Streptomyces lividans or S. murinus, may be very suitable as heterologous hosts because of their capability to secrete proteins into the culture medium. Other bacteria that may be suitable as hosts are those from the genera Pseudomonas.

Depending on the nature of the nucleotide sequence encoding an enzyme having the specific properties as defined herein, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Suitable yeast organisms may be selected from the species of Kluyveromyces, Saccharomyces or Schizosaccharomyces, e.g. Saccharomyces cerevisiae, or Hansenula (disclosed in UK Patent Application No. 9927801.2).

Suitable filamentous fungus may be for example a strain belonging to a species of Aspergillus, such as Aspergillus oryzae or Aspergillus niger, or a strain of Fusarium oxysporium, Fusarium graminearum (in the perfect state named Gribberella zeae, previously Sphaeria zeae, synonym with Gibberella roseum and Gibberella roseum f. sp. Cerealis), or Fusarium sulphureum (in the perfect state named Gibberella puricaris, synonym with Fusarium trichothercioides, Fusarium bactridioides, Fusarium sambucium, Fusarium roseum and Fusarium roseum var. graminearum), Fusarium cerealis (synonym with Fusarium crokkwellnse) or Fusarium venenatum.

By way of example, typical expression hosts may be selected from Aspergillus niger, Aspergillus niger var. tubigensis, Aspergillus niger var. awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis, Saccharomyces cerevisiae and Hansenula polymorpha.

The use of suitable host cells—such as yeast, fungal and plant host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

The host cell may be a protease deficient or protease minus strain. This may for example be the protease deficient strain Aspergillus oryzae JaL 125 having the alkaline protease gene named "alp" deleted. This strain is described in WO97/35956.

Organism

The term "organism" in relation to the present invention includes any organism that could comprise a nucleotide sequence coding for an enzyme having the specific properties as defined herein and/or products obtained therefrom.

Suitable organisms may include a prokaryote, fungus, yeast or a plant.

The term "transgenic organism" in relation to the present invention includes any organism that comprises a nucleotide sequence coding for an enzyme having the specific properties as defined herein and/or the products obtained therefrom, and/or wherein a promoter can allow expression of the nucleotide sequence coding for an enzyme having the specific properties as defined herein within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, a nucleotide sequence coding for an enzyme having the specific properties as defined herein, constructs as defined herein, vectors as defined herein, plasmids as defined herein, cells as defined herein, or the products thereof. For example the transgenic organism can also comprise a nucleotide sequence coding for an enzyme having the specific properties as defined herein under the control of a heterologous promoter.

Transformation of Host Cells/Organism

As indicated earlier, the host organism can be a prokaryotic or a eukaryotic organism. Examples of suitable prokaryotic hosts include E. coli and Bacillus subtilis. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence may need to be suitably modified before transformation—such as by removal of introns.

In another embodiment the transgenic organism can be a yeast. In this regard, yeast have also been widely used as a vehicle for heterologous gene expression. The species Saccharomyces cerevisiae has a long history of industrial use, including its use for heterologous gene expression. Expression of heterologous genes in Saccharomyces cerevisiae has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons Saccharomyces cerevisiae is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of Saccharomyces cerevisiae.

A review of the principles of heterologous gene expression in Saccharomyces cerevisiae and secretion of gene products is given by E Hinchcliffe E Kenny (1993, "Yeast as a vehicle for the expression of heterologous genes", Yeasts, Vol 5, Anthony H Rose and J Stuart Harrison, eds, $2^{nd}$ edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Filamentous fungi cells may be transformed by a process involving protoplast formation and transformation of the protoplasts followed by regeneration of the cell wall in a manner known. The use of Aspergillus as a host microorganism is described in EP 0 238 023.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205-225) and Christou (Agro-Food-Industry Hi-Tech March/April 1994 17-27). Further teachings on plant transformation may be found in EP-A-0449375.

Host cells transformed with the nucleotide sequence may be cultured under conditions conducive to the production of the encoded enzyme and which facilitate recovery of the enzyme from the cells and/or culture medium.

The medium used to cultivate the cells may be any conventional medium suitable for growing the host cell in questions and obtaining expression of the enzyme. Suitable media are available from commercial suppliers or may be prepared according to published recipes (e.g. as described in catalogues of the American Type Culture Collection).

The protein produced by a recombinant cell may be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions may join the coding sequence to nucleotide sequence encoding a polypeptide domain which will facilitate purification of soluble proteins (Kroll D J et al (1993) DNA Cell Biol 12:441-53).

The enzyme may be secreted from the host cells and may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Secretion

Often, it is desirable for the enzyme to be secreted from the expression host into the culture medium from where the enzyme may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from Aspergillus), the a-factor gene (yeasts e.g. Saccharomyces, Kluyveromyces and Hansenula) or the α-amylase gene (Bacillus).

Fusion Proteins

An enzyme having the specific properties as defined herein may be produced as a fusion protein, for example to aid in extraction and purification thereof. Examples of fusion protein partners include glutathione-S-transferase (GST), 6×His, GAL4 (DNA binding and/or transcriptional activation domains) and (β-galactosidase. It may also be convenient to include a proteolytic cleavage site between the fusion protein partner and the protein sequence of interest to allow removal of fusion protein sequences. Preferably the fusion protein will not hinder the activity of the protein sequence.

The fusion protein may comprise an antigen or an antigenic determinant fused to the enzyme. In this embodiment, the fusion protein may be a non-naturally occurring fusion protein comprising a substance which may act as an adjuvant in the sense of providing a generalised stimulation of the immune system. The antigen or antigenic determinant may be attached to either the amino or carboxy terminus of the enzyme.

In another embodiment of the invention, the amino acid sequence of an enzyme having the specific properties as defined herein may be ligated to a heterologous sequence to encode a fusion protein.

EXAMPLES

Figure 2:
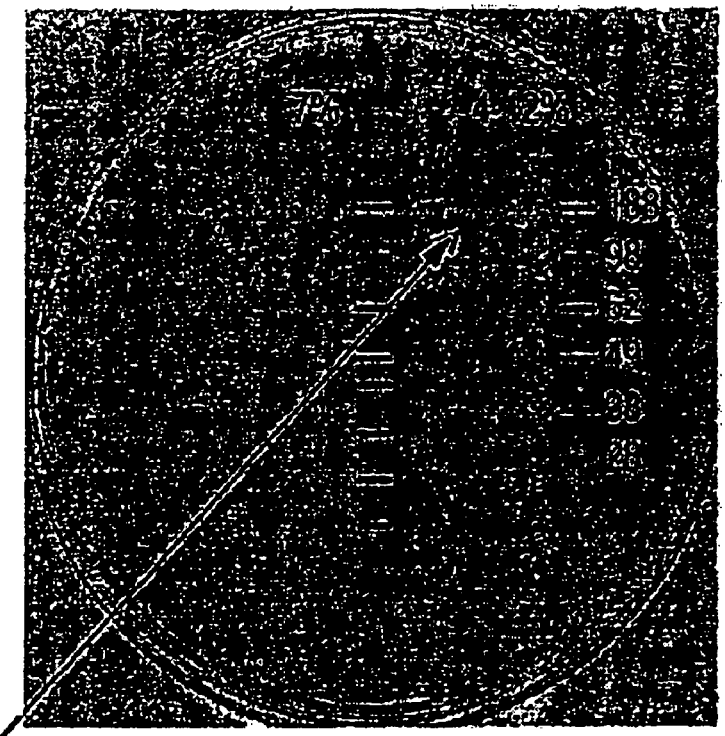
Figure 3:
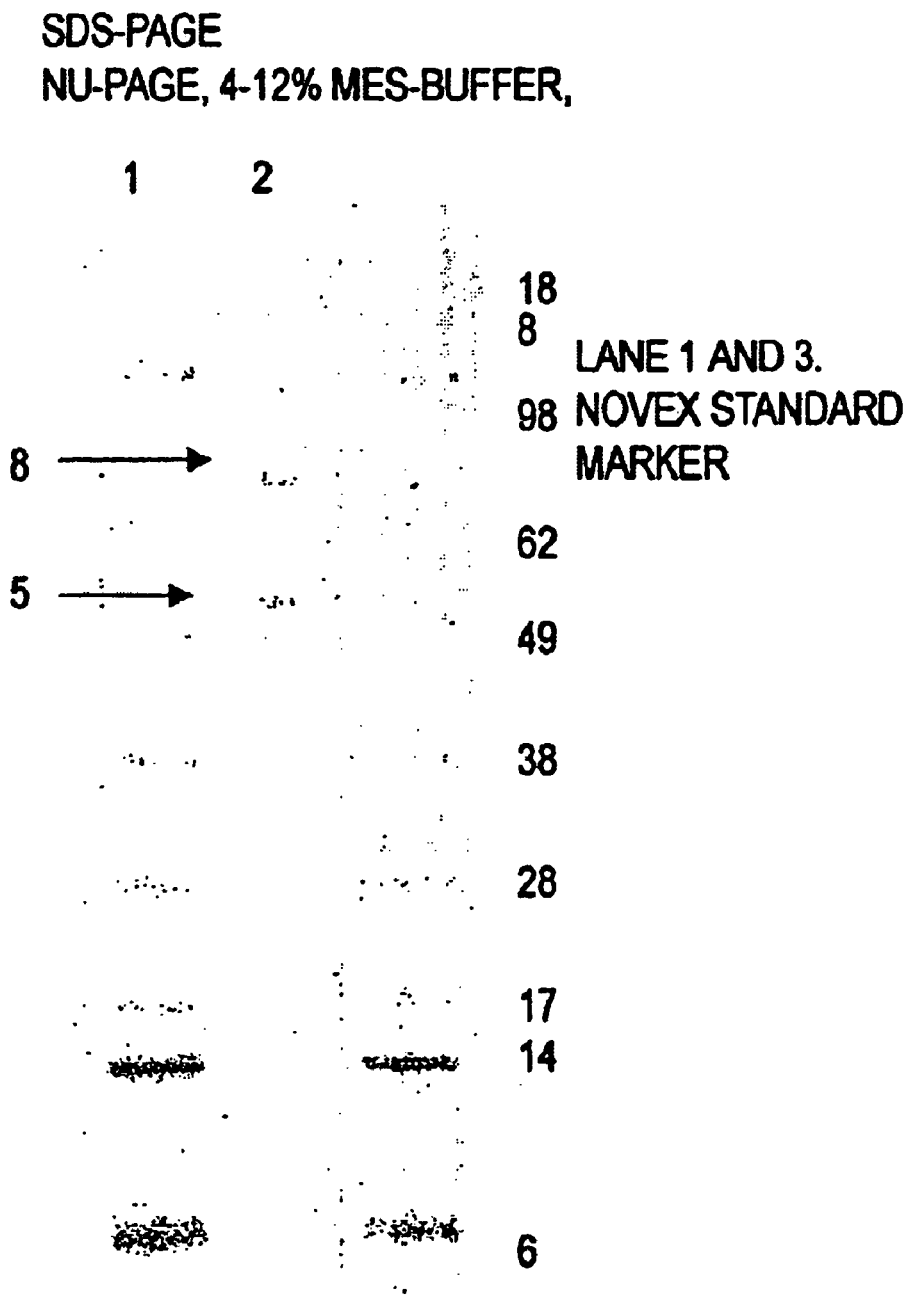
Figure 4:
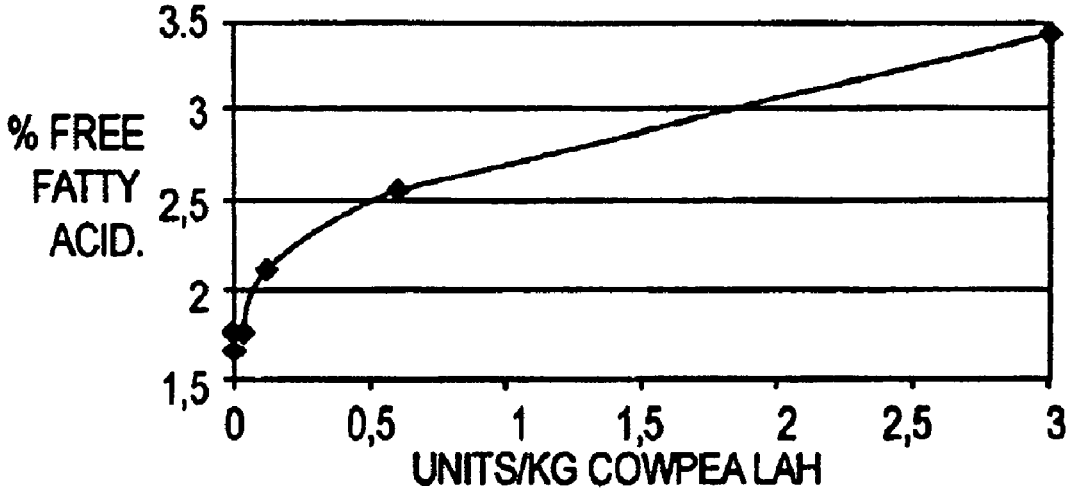
Figure 5:
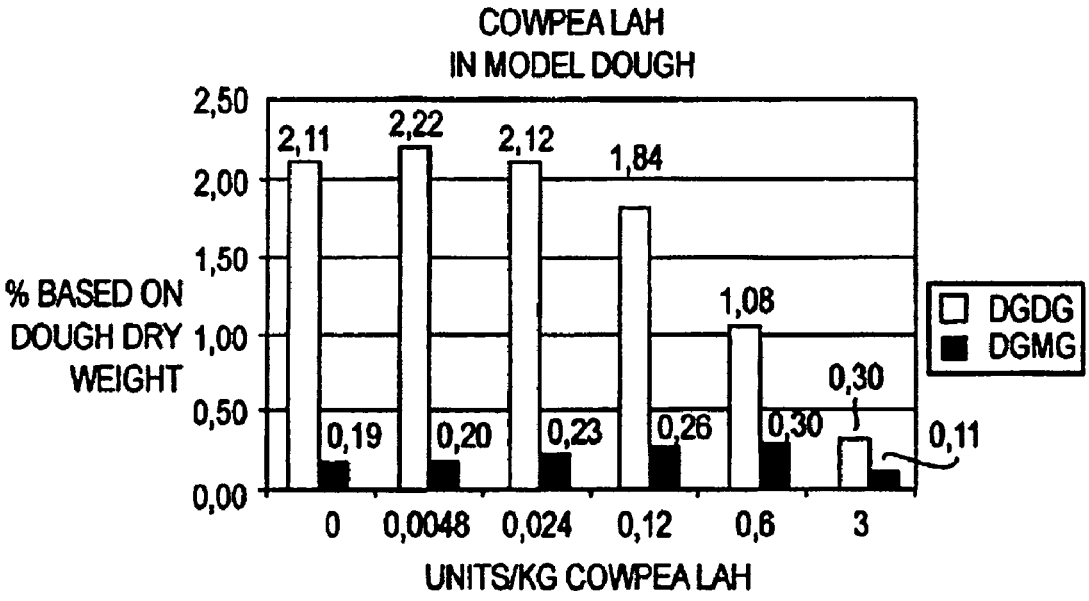
Figure 6:
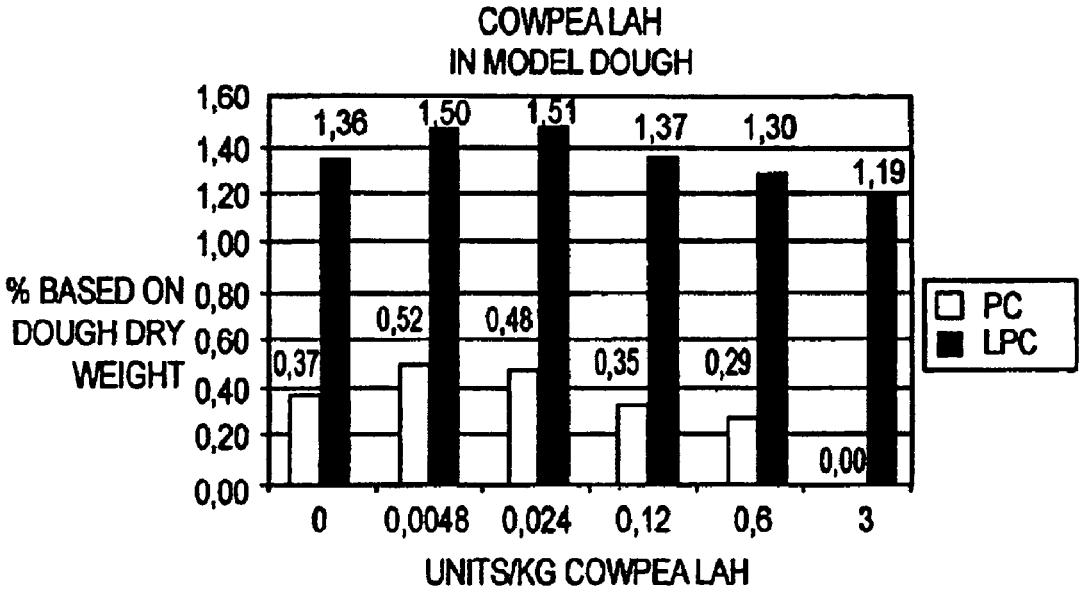
Figure 7:
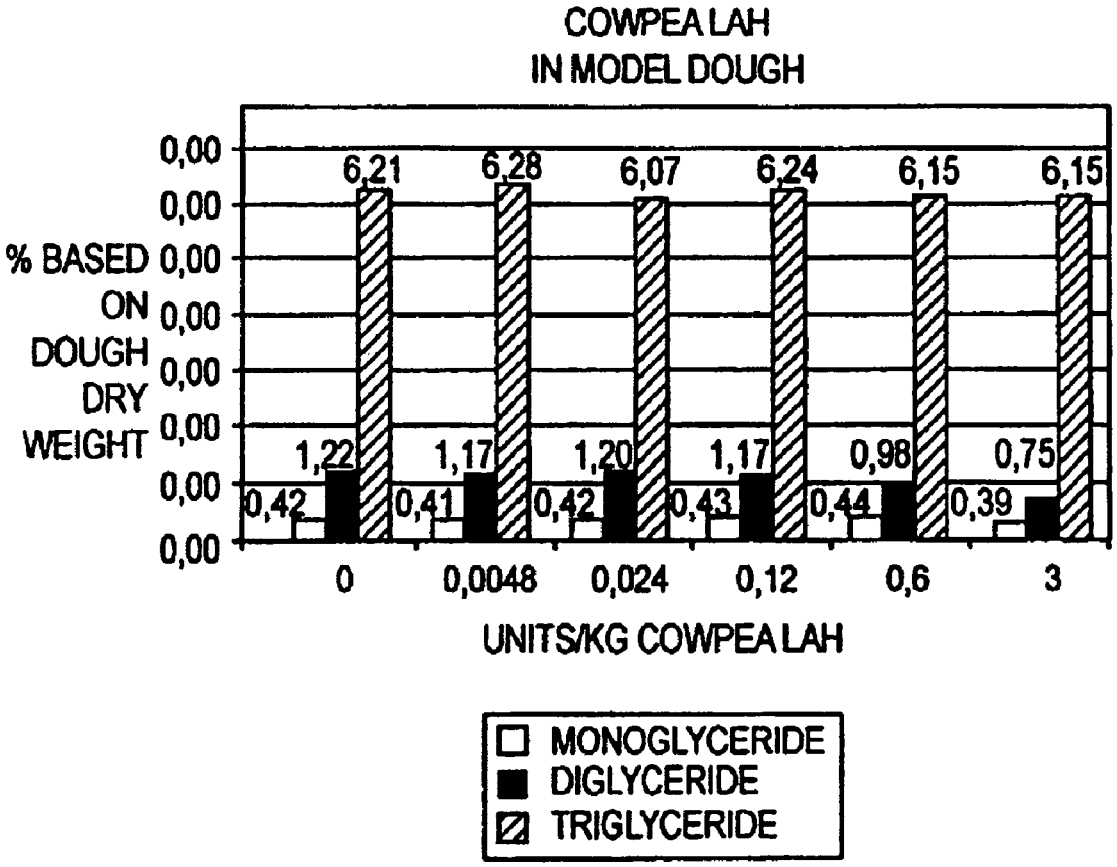
Figure 8:
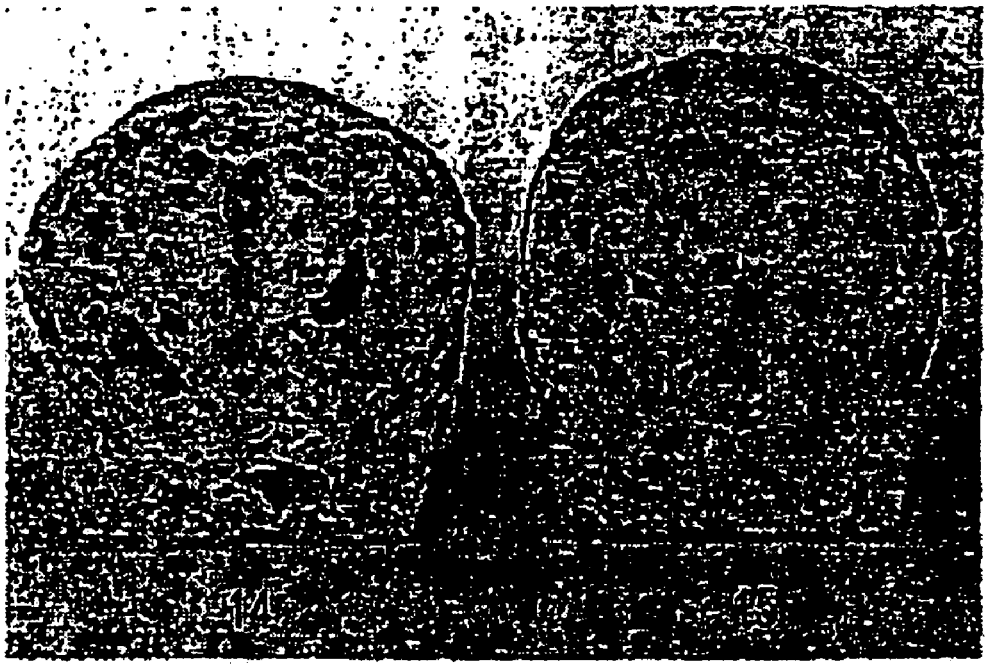
Figure 9:
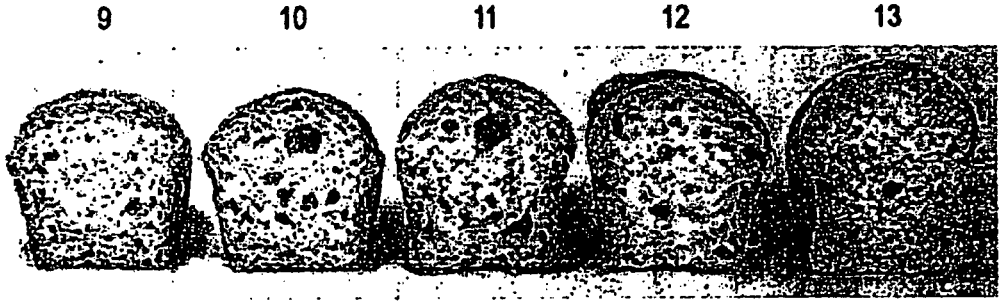
Figure 10:
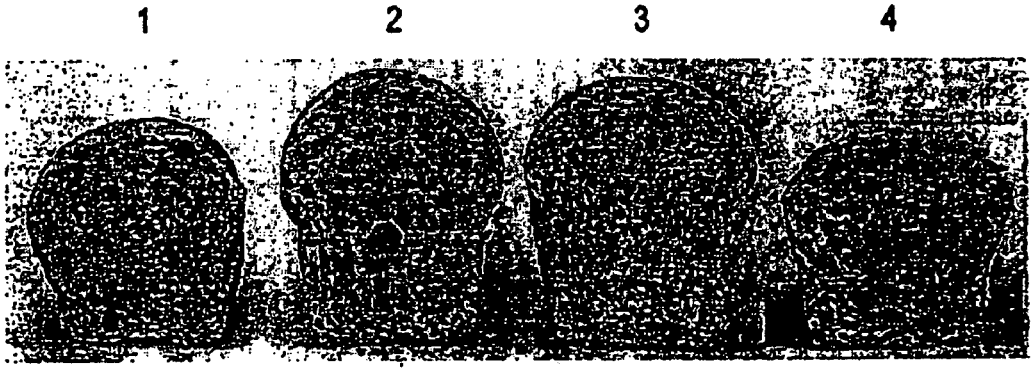
Figure 12:
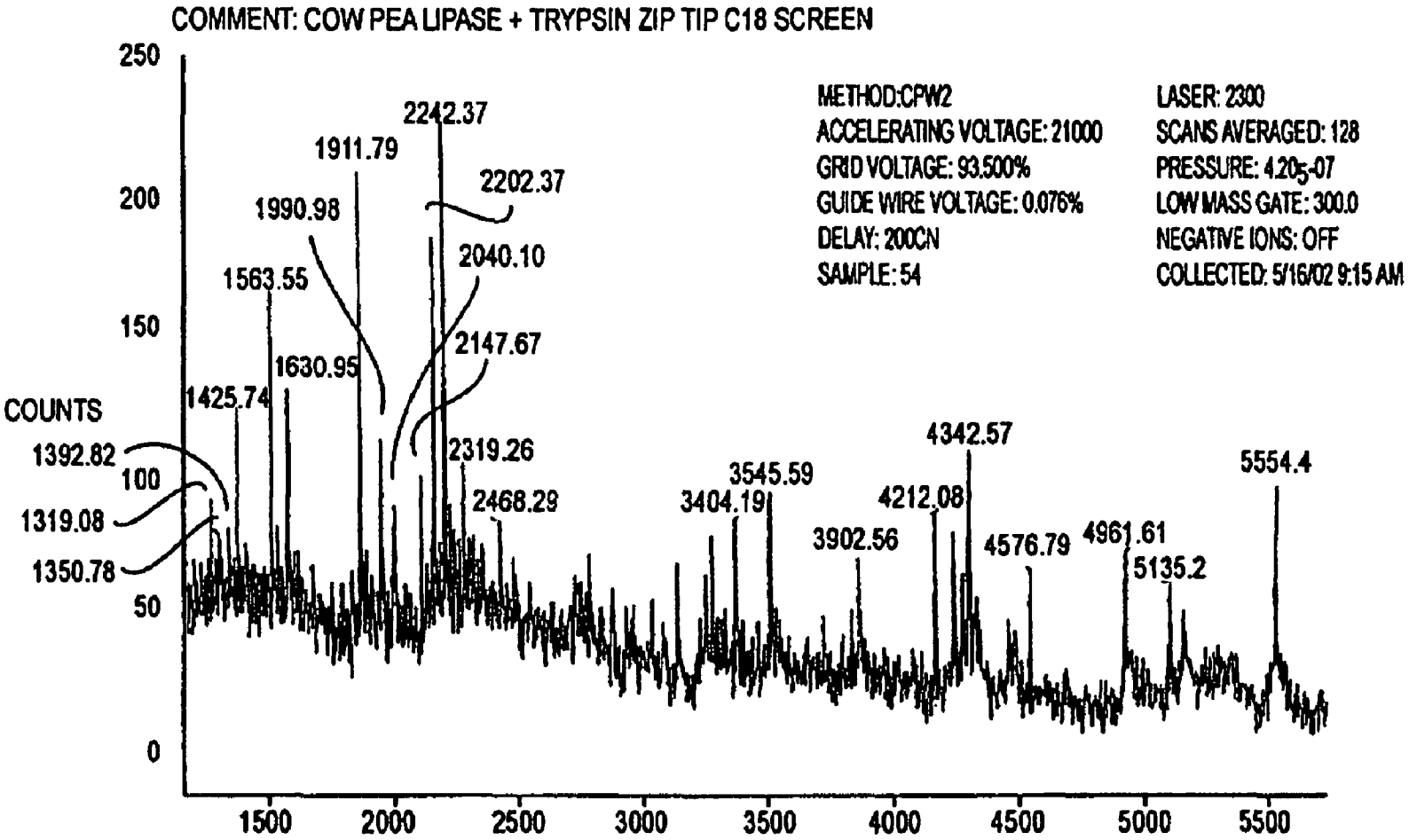

The present invention may now be described, by way of example only, in which reference may be made to the following figures:

FIG. 1, which shows a native-PAGE gel;

FIG. 2, which shows a galactolipid (DGDG) zymogram;

FIG. 3, which shows a SDS-PAGE gel;

FIG. 4, which shows a graph of the effect of cowpea LAH 1 in dough;

FIG. 5, which shows a graph of HPLC analysis of galactolipids in dough treated with cowpea LAH;

FIG. 6, which shows a graph of HPLC analysis of phospholipids in dough treated with cowpea LAH;

FIG. 7, which shows a graph of GLC analysis of non-polar lipids in dough treated with cowpea LAH;

FIG. 8, which shows a photograph of minibread wherein loaf 14 had 2% soy oil and loaf 15 had 2% soy oil+1.07 Units/kg of cowpea LAH added;

FIG. 9, which shows a photograph of minibread wherein loaf 9 is the control; loaf 10 had 1.07 Units/kg cowpea LAH added; loaf 11 had 1.07 Units/kg cowpea LAH+0.1% galactolipid added; loaf 12 had 1.07 Units/kg cowpea LAH+0.2% galactolipid added; and loaf 13 had 1.07 Units/kg cowpea LAH+0.4% galactolipid added;

FIG. 10, which shows a photograph of minibread wherein loaf 1 is the control; loaf 2 had 0.4% DGDG added; loaf 3 had 0.4% DGDG+0.4 Units/g Cowpea LAH added; and loaf 4 had 0.4 Units/g Cowpea LAH;

FIG. 11, which shows an expression vector which was derived from pYES2. The Gal1 promoter of pYES2 was removed and replaced by the constitutive ADH promoter. LipA was incorporated by in vivo recombination in Saccharomyces cerevisiae. Abbreviations: Amp, ampicillin resistant gene; ADH3', alcohol dehydrogenase 3' region; ADHP, alcohol dehydrogenase gene promoter; bps, base pairs; CYC1, Transcription terminator; f1 ori, f1 origin; Gal1p, galactose gene promoter; LipA, lipase gene from Aspergillus tubigensis; MCS, multiple cloning site; pMB1 ori, pUC derived origin, ura3, gene encoding uracil, 2μ ori, 2μorigin;

FIG. 12, which shows a Maldi-TOF profile from the Lipolytic Acyl Hydrolase Enzyme from cowpea identified using the method detailed herein; and FIG. 13, which shows a peptide profile for VUPAT 1 (Matos et al FEBS Letters 491 (2001) 188-192).

MATERIALS AND METHODS

Enzymes:

Purified cowpea lipid acyl hydrolase (LAH)

Isolated membrane-bound galactolipase from wheat thylakoids

Flour:

Danish flour 'Sølvmel' nr. 2001084

Substrate:

Digalactosyldiglyceride, DGDG(55% pure) batch KGL01013, from Lipid Technologies Provider, Karlshamn, Sweden.

Procedures

Cowpea Lipolytic Acyl Hydrolase Enzyme (E.C. 3.1.1.26)

Plant Material

A lipolytic acyl hydrolase (LAH) capable of hydrolysing a glycolipid and a phospholipid, but incapable, or substantially incapable, of hydrolysing a triglyceride and/or a 1-monoglyceride, was isolated from cowpea. The lipolytic acyl hydrolases were obtained by a method based on that described in Sahsah et al (Biochemica et Biophysica Acta 1215 (1994) 66-73). An alternative suitable method may be that described in Matos et al (FEBS Letters 491 (2001) 188-192).

Cowpea beans were obtained from Morelos, Mexico. The plants were grown on Leca stones and watered with mineral nutrient solution according to Ellfolk, Biochim. Biophys. Acta 192 (1969) 486-493 (enriched with 6 mM of potassium nitrate), in a growth chamber, in pots of dimension 35×50 cm (approx. 50 plants in each pot), under temperature and light controlled conditions (16 hours daylight at 22° C. and 8 hours darkness at 18° C. with a relative air humidity of 72%). The leaves were harvested after 21 days of cultivation. At the harvest time the plants had 4-7 fully expanded mature leaves and 3-8 young leaves.

Extraction of Lipolytic Acyl Hydrolase Enzymes from Leaves 215 g of fresh leaves frozen in liquid nitrogen were homogenised in an industrial blender and extracted in 500 ml of 5 mM TRIS-buffer (pH 7.0), using an industrial blender (3 minutes mixing). The insoluble materials were removed by 20 minutes centrifugation at 15000 g. The resulting supernatant was finally filtered through a 0.45 μm filter (605 ml crude extract was collected).

Purification of the Lipolytic Acyl Hydrolase Enzymes

Step 1. Ultra Filtration

This step was carried out, using a 50 kDa Amicon ultra filtration unit. 122 ml concentrated crude extract was collected.

Step 2. Ammonium Sulphate Precipitation

Solid ammonium sulphate (68.5 g) was added to the crude extract to a final concentration of 80% saturation. The mixture was left stirring for 60 minutes at room temperature (25° C.). The precipitated protein was collected by centrifugation at 15000 g for 20 minutes. The precipitant was re-dissolved in 30 ml of 20 mM TEA buffer (pH 7.3). The insoluble material was removed by centrifugation at 15000 g for 20 minutes.

Step 3. Desalting (GFC)

The supernatant was desalted on a Sephadex G-25 column (5×25 cm, Pharmacia, Sweden), which was equilibrated with 20 mM TEA (pH 7.3) at a flow rate of 15 ml/min. The fractions containing galactolipase activity, (protein peak) were pooled (100 ml).

Step 4. Ion Exchange Chromatography (IEC)

The desalted sample was then applied to a Q-Sepharose Fast Flow (5×6 cm, Pharmacia, Sweden), equilibrated with 20 mM TEA (pH 7.3) at a flow rate 16 ml/minutes. To remove the unbound proteins, the column was washed with 250 ml of the same buffer, and bound proteins were eluted out by a linear gradient of 0-0.6 M NaCl in the same buffer. Fractions of 16 ml were collected and assayed for galactolipase activity. The fractions which contained galactolipase activity were pooled (128 ml).

Step 5. Ultrafiltration

This step was carried out as described in step 1.

A 16 ml desalted/concentrated sample was collected ($V_{max}$: 5.6 mOD/min. or 0.010 U/ml).

Baking trials were performed with a sample from this step.

Step 6. Ion Exchange Chromatography (IEC)

The desalted/concentrated (11 ml) sample was then applied to a Poros Q10 (0.5×5 cm, Applied Biosystem, USA), equilibrated with the same buffer as used in step 4, at a flow rate 1.5 ml/minute. Bound proteins were eluted by a linear gradient of 0-0.65 M NaCl in the same buffer. Fractions of 1.5 ml were collected and assayed for galactolipase activity. The fractions which contained galactolipase activity were pooled (6 ml).

Characterisation of Cowpea Lipolytic Acyl Hydrolase Enzyme

SDS-PAGE Analysis, Determination of Purity and Molecular Weight:

Purified lipolytic acyl hydrolase from IEC (step 6) was applied to a gel (NU-PAGE, 4-12%, MES-buffer, Novex, USA) and the gel was then coomassie stained. The gel revealed the existence of several bands (see FIG. 1). Attempts to further purify the lipolytic acyl hydrolase using several chromatographic techniques such as gel filtration chromatography, hydrophobic interaction chromatography, chromatofocusing, etc. did not improve the purity of the lipolytic acyl hydrolase.

Determination of Molecular Weight and Electro Elution of Lipolytic Acyl Hydrolase After Native PAGE:

Lipolytic Acyl Hydrolase was purified from cowpea (Vigna unguiculata) according to Sahsah et al. (Biochim. Biophys. Acta 1215 (1994) 66-73. Diffusion eluted lypolytic acyl hydrolase was then subjected to a SDS-PAGE gel. The gel was coomassie stained. This gel revealed 2 major bands at 57 and 84 kDa (see FIG. 3).

This preparation was subjected to trypsin digestion using the following protocol:

1. Add 50 μL 8M Urea in 0.4 M Ammonium bicarbonate buffer pH 8.1 (24.04 g urea, 1.581 g Ammonium bicarbonate per 50 mls)
2. Overlay with Nitrogen and incubate at 50° C. for 5 minutes.
3. Add 5 μL 50 mM DTT (8 mg/ml water)
4. Mix well, overlay with Nitrogen and incubate at 50° C. for 15 mintues.
5. Cool to room temperature.
6. Add 5 μL 100 mM Iodoacetamide (19 mg/ml water).
7. Mix well, overlay with Nitrogen and incubate in the dark at room temperature for 15 minutes.
8. Add 140 μL water, mix well and add trypsin at 1:25 (Trypsin is stored at 20° C. at 1 μg/μL in 0.1% TFA).
9. Overlay with Nitrogen and incubate overnight at 37° C.
10. Stop the reaction by freezing at −20° C.
11. Recover peptides by R.P. phase HPLC using a C18 column.

Post digestion peptide screening using ZipTip™ C18 desalting tips:

A. Wet the tip by aspirating in Methanol 4×10 μL.
B. Equilibrate the tip by washing 5×10 μL with 0.1% T.F.A. in water.
C. Bind peptides by aspirating 20× in the protein digest solution.
D. Remove salts by washing with 10×10 μL 0.1% T.F.A. in water.
E. Elute peptides directly on to a Maldi-TOF target plate with 2 μL of a 10 mg/ml α-cyano-4-hydroxycinnamic acid in 0.1% T.F.A. in 60% acetonitrile/water.
F. Ascertain the molecular weight of the peptides using a Voyage DE Maldi-TOF mass spectrometer.

The results of the Maldi-TOF analysis are presented in FIG. 12.

A comparison between the theoretical peptide profile (see FIG. 13) for VUPAT 1 (as taught in Matos et al. FEBS Letters 491 (2001) 188-192) and the experimentally obtained peptide profile for the lypolytic acyl hydrolase from cowpea obtained herein shows that the lipolytic acyl hydrolase purified herein is a different protein from that taught in Matos et al. This is also confirmed by the molecular weights determined by SDS-Page. In this study a molecular weight of 57 and 84 kDa is determined contrary to a molecular weight of 40 kDa reported by Sahsah et al.

A Membrane-Bound Lipolytic Acyl Hydrolase from Thylakoids from Wheat Leaves.

Plant Material

Wheat (Herward) was obtained from Pajbjergfonden, Odder, Denmark. Wheat grains were grown on paper at 25° C. and irrigated regularly. After one week the wheat leaves were harvested.

Homogenation Buffer:

50 mM HEPES, 350 mM Sorbitol, 1 mM EDTA, 1 mM $MgCl_2$, 1 mM $MnCl_2$ of 1 mM DTT, pH 8.3/NaOH). The buffer was kept on ice before use.

Extraction of Membrane-Bound Lipolytic Acyl Hydrolase 26 g wheat leaves were cut into small pieces (½ cm). 78 ml ice cold homogenation buffer was added. The leaves were homogenized in a high speed Ultra Turrax Mixer for 12 seconds.

Large particles were removed by filtration through 3 layers of Kleenex tissue. The filtrate was centrifuged at 250 g for 1 minute and the supernatant isolated.

The chloroplasts were isolated by centrifugation for 5 minutes at 1000 g. The pellets (comprising membrane-bound lipolytic acyl hydrolase) were resuspended in 1 ml homogenation buffer (microscopy analysis clearly showed the chloroplasts)

The pellets were used for testing in wheat model dough system.

Mini Baking Test

The following ingredients were added to a 50 g Brabrender mixing bowl and kneaded for 5 minutes at 30° C.: flour 50 g, dry yeast 1.0 g, sugar 0.8 g, salt 0.8 g, 70 ppm ascorbic acid and water (to a dough consistency of 400 Brabender units). Resting time was 10 min. at 34° C. The dough was scaled 15 g per dough. Then moulded on a special device where the dough was rolled between a wooden plate and a Plexiglas frame. The doughs were proofed in tins for 45 min. at 34° C., and baked in a Voss household oven for 8 min. 225° C.

After baking the breads were cooled to ambient temperature and after 20 min. The breads were scaled and the volume was determined by rape-seed displacement method.

The breads were also cut and crumb and crust evaluated.

Model Dough 10 g of flour and 0.020 g sodium chloride were mixed in a 10 g Farinograph mixing bowl for 1 minute either with or without enzymes. Subsequently water (500 Brabender units) was added and mixed for 5 minutes at 30° C. After mixing the dough was placed at 32° C. for 1 hour, and then frozen and freeze dried prior to further analysis.

Baking Tests (Danish Rolls)

Flour, Danish reform 1500 g, Compressed Yeast 90 g, sugar 24 g, salt 24 grams, water 400 Brabender units+2% were kneaded in a Hobart™ mixer with hook for 2 minutes low speed and 9 minutes high speed. The dough temperature was 26° C. The dough was scaled 1350 gram. Resting 10 min. at 30° C. and moulded on a Fortuna moulder. The dough was proofed 45 min. at 34° C. The dough was baked in a Bago-oven 18 min. 220° C. and steamed for 12 sec.

After cooling the rolls were scaled and the volume of the rolls was measured by the rape seed displacement method.

Specific bread volume $$\text{Specific volume} = \frac{\text{Volume of the bread, ml}}{\text{Weight of the bread, gram}}$$

The dough quality parameters were also evaluated.

| | |
|---|---|
| Dough elasticity | 1-10 |
| Stickiness | 1-10 |

Baking Tests (Toast Bread)

Flour, Danish reform 2000 g, Dry yeast 30 g, sugar 30 g, salt 30 gram and, water 400 Brabender units+3% was kneaded in a Hobart™ Mixer with hook for 2 min. at low speed and 10 min. at high speed. Dough temperature after mixing was 25° C. Resting time was 10 min. at 30° C. The dough was scaled 750 gram per dough. Then rested again for 5 min. at 33° C. and 85% RH. The dough was moulded on a Glimik moulder. The doughs were proofed in tins for 50 min. at 33° C., and baked in a Wachtel oven 40 min. 220° C. and steam injection for 16 sec.

After cooling the bread was scaled, and the volume of the bread was measured by the rape seed displacement method.

The crumb was also evaluated subjectively on a scale 1 to 10, where 1=course inhomogeneous and 10=nice homogeneous.

Three breads baked in tins with lids were stored at 20° C. and used for firmness measurements.

Firmness

Firmness of bread was measured on a Instron™ M model 4301 connected to a computer.

Conditions for measurement of bread firmness:

Load Cell Max. 100 N

Piston Diameter 50 mm

Cross Head Speed 200 mm/min

Compression 25%

Bread Slice thickness 11 mm

The force is converted to $N/dm^2$.

The result was an average from measurement on 10 bread slices for every bread.

Lipid Extraction and Fatty Acid Analyses 10 g of fully proofed dough was immediately frozen and freeze dried. The freeze-dried dough was milled in a coffee mill and passed through an 800 micron screen. 1.5 g freeze-dried dough was scaled in a 15 ml centrifuge tube with screw top lid. 7.5 ml water saturated butanol (WSB) was added. The centrifuge tube was placed in a boiling water bath for 10 minutes. The tubes were placed in a Rotamix and rotated at 45 rpm for 20 minutes at ambient temperature and then placed in a boiling water bath again for a further 10 minutes prior to being Rotated on the Rotamix for a further 30 minutes at ambient temperature. The tubes were centrifuged at 3500 g for 5 minutes. 5 ml supernatant was transferred into a vial and the WSB was evaporated to dryness under a steam of nitrogen.

The free fatty acids in the extract were analysed as Cu-salts in isooctane measured at 715 nm and quantified according to a calibration curve based on oleic acid (Kwon D. Y. and Rhee J. S. (1986), A simple and rapid Colourimetric Method for Determination of Free Fatty Acids for Lipase Assay, JAOCS 63:89). Determination of Glycolipids and Phospholipids by HPLC.

1. Chromatographic Conditions

| | | | |
|---|---|---|---|
| System | Waters 600 | | |
| Column | (LiChrospher ® 100 DIOL 5 μm) LiChroCART ® | LxD: 250 * 4.0 mm id. | Temp: 50° C. |
| Injector | Waters 717plus Autosampler | | Vol: 15 μl |
| Detector | Alltech 500 ELSD, evaporative light-scattering | | Temp: 80° C. Gasflow: 1.50 L/min m/MFC |
| Integrator | Waters Millennium | | |
| Mobile phase | A: 1000 Heptane/15 $CH_3COOH$ B: 500 Hcptane/500 Isopropanol/15 $CH_3COOH$ C: 300 Heptane/600 Isopropanol/100 $H_2O$/15 $CH_3COOH$ | | Flow: 1.25 ml/min Pressure: 1000-2500 psi |

| Gradient | Flow | Time(min) | % A | % B | % C | Comments |
|---|---|---|---|---|---|---|
| | 1.25 | 0 | 100 | 0 | 0 | |
| | 1.25 | 10 | 60 | 40 | 0 | |
| | 1.25 | 25 | 20 | 30 | 50 | |
| | 1.25 | 35 | 0 | 0 | 100 | |
| | 1.25 | 38 | 0 | 90 | 10 | |
| | 1.25 | 40 | 30 | 70 | 0 | |
| | 1.25 | 45 | 100 | 0 | 0 | |
| | 1.25 | 55 | 100 | 0 | 0 | new injection |

2. Stock Solution

ILPS* standard was dissolved in $CHCl_3/CH_3OH$ (75/25) ~2 mg/ml PC

Dilution of stock: 0.7, 0.14, 0.028,

| | | |
|---|---|---|
| *Phosphatidic acid | PA | 5.13% |
| Phosphatidylethanolamine | PE | 12.74% |
| Phosphatidylcholine | PC | 14.76% |
| Phosphatidylinositol | PI | 10.13% |

*ILPS(International Lecithin and Phospholipid Society) standard is obtained from Spectral Service GmbH Köln, Germany.

3. Sample Preparation

Samples were dissolved in $CHCl_3/CH_3OH$ (75/25), sonicated and filtered through a 0.45 μm filter 4. Calibration Model Calibration model: log-log linear calibration The calibration curve for PC was used to calculate the amounts of the glycolipids and phospholipids.

Gas Chromatography

Perkin Elmer 8420 Capillary Gas Chromatography equipped with WCOT fused silica column 12.5 m×0.25 mm ID×0.1 μm 5% phenyl-methyl-silicone (CP Sil 8 CB from Crompack).

Carrier: Helium.

Injection: 1.5 μl with split.

Detector: FID. 385° C.

| Oven program: | 1 | 2 | 3 | 4 |
|---|---|---|---|---|
| Oven temperature, ° C. | 80 | 200 | 240 | 360 |
| Isothermal, time, min | 2 | 0 | 0 | 10 |
| Temperature rate, ° C./min | 20 | 10 | 12 | |

Sample preparation: 50 mg wheat lipid was dissolved in 12 ml heptane: pyridine 2:1 containing an internal standard heptadecane, 2 mg/ml. 500 μl of the sample was transferred to a crimp vial. 100 μl MSTFA (N-Methyl-N-trimethylsilyltrifluoracetamid) was added and the reaction incubated for 15 minutes at 90° C. Calculation: Response factors for mono-di-triglycerides and free fatty acid were determined from reference mixtures of these components. Based on these response factors the mono-di-triglycerides and free fatty acids in wheat lipids were calculated.

Galactolipid (DGDG) Zymogram (Spot Plate) Assay.

Preparation of plates.

Solution 1.

2 g Agarose was dissolved in 110 ml water by heating to 90-100° C.

Solution 2.

1.2 g galactolipid was dispersed in 40 ml demineralised water. 50 ml 0.1M phosphate buffer pH 7 was added, subsequently 0.6 ml 0.2% Rhodamine B was also added.

Solution 1 was cooled to approx. 70° C. and solution 2 was added whilst stirring. 12 ml of the final mixture was transferred to a 7 cm Petri dish.

The plates were stored at 5° C. until use.

Assay.

Small holes of 1 mm in diameter was punched out of the gel and 10 μl enzyme solution was transferred to the hole. The formation of haloes in the agarose gels was followed as a function of time.

A blank without enzyme was also added to one of the holes for comparison.

Assay for Enzyme Activity

Preparation of substrate for enzymatic assay: The substrate, pNP-Caprate (C10), was dissolved in ethanol and diluted in 100 mM Na-Phosphate-buffer (pH 6.3) to a final concentration of 0.1 mg,/ml substrate and 30% ethanol respectively, and kept at room temperature.

Assay method: The enzyme assay mixture contained 30 μl sample/blank and 250 μl substrate. The mixture was incubated at 35° C. for 30 minutes (420 nm) whilst simultaneously running an ELISA-reader (420 nm) kinetic program. The $V_{max}$ value was used for calculation of enzyme activity (U/ml). $V_{max}$ was converted to μmol from a standard curve for solutions of pNP measured under the same conditions as the sample. The enzyme activity is defined as the amount of enzyme which produce 1 μmol of pNP per min. at 35° C.

Screening Method for Random Mutagenesis

Libraries of enzymes obtained from random mutagenesis or localised random mutagenesis may be spread on cellulose acetate filters on agar plates containing growth media and incubated.

The cellulase acetate filters are then transferred to the selection plates and incubated at 37° C. for 2-6 hours. Cells harbouring active enzyme under the given conditions will develop clearing zones around the colonies. The positive variants can then be further purified and tested.

Results

Example 1

In the first series of dough experiments purified cowpea LAH was tested in 10 g dough in different concentrations in order to test the activity of the enzyme in dough and in order to find a suitable dosage for baking experiments. The activity of the enzyme was measured by analysing the level of free fatty acid in dough. The results are shown in Table 1 and FIG. 4.

TABLE 1

Effect of Cowpea LAH in Model Dough

| Cowpea LAH Units/kg flour | Fatty acid in dough ‰ |
|---|---|
| 3 | 3.44 |
| 0.6 | 2.55 |
| 0.12 | 2.13 |
| 0.024 | 1.78 |
| 0.0048 | 1.66 |
| 0 | 1.77 |

The results detailed in Table 1 and FIG. 4 clearly show that LAH from cowpea is active in dough during the production of free fatty acid.

Lipids extracted from the dough were further analysed by HPLC in order to study the effect on polar lipids in the dough.

Results from the HPLC analyses of dough lipids are shown in Table 2 and FIGS. 5 and 6.

TABLE 2

HPLC analysis of polar lipids in dough.

| Cowpea LAH Units/kg flour | ‰ DGDG | ‰ PC | ‰ DGMG | ‰ LPC |
|---|---|---|---|---|
| 0 | 2.11 | 0.37 | 0.19 | 1.36 |
| 0.0048 | 2.22 | 0.52 | 0.20 | 1.50 |
| 0.024 | 2.12 | 0.48 | 0.23 | 1.51 |
| 0.12 | 1.84 | 0.35 | 0.26 | 1.37 |
| 0.6 | 1.08 | 0.29 | 0.30 | 1.30 |
| 3.0 | 0.30 | 0.00 | 0.11 | 1.19 |

The non-polar lipids were analysed by GLC. The results from this analysis are shown in FIG. 7.

HPLC analysis clearly shows the effect of cowpea LAH on galactolipids, and at a high enzyme dosage digalactosyldiglyceride (DGDG) is almost completely hydrolysed. The results also show a small increase in the concentration of the corresponding monoester, DGMG. At increased concentration of cowpea LAH, DGMG is however also hydrolysed. The same picture is also observed for phosphatidylcholine (PC) which is hydrolysed, followed by a small increase in the corresponding lysophosphatidylcholine. At increased concentration of cowpea LAH lysophosphatidylcholine is also hydrolysed in the dough.

In conclusion, it is observed that both galactolipids and phospholipids in dough are degraded by cowpea LAH.

The GLC analysis indicates no activity of cowpea LAH on triglyceride compared with the activity on polar lipids and the free fatty acid formation.

It is very clear that 3 Units/kg of cowpea LAH is a strong over dosage of this enzyme, which causes almost complete hydrolyses of all galactolipids in dough.

Example 2

Cowpea LAH was tested in minibread analysis in two different concentrations and compared to a control (without cowpea LAH added). The volume of the bread was evaluated as well as an evaluation of crumb structure and appearance. Fully proofed dough from this test was frozen and freeze dried and the dough lipid extracted. Isolated dough lipids were analysed by HPLC and GLC analysis.

The results from the baking test is shown in Table 3.

TABLE 3

Baking Test with Cowpea LAH

| Test no. | Cowpea LAH % in dough | Bread volume ml/g | Fatty acid in dough, ‰ |
|---|---|---|---|
| 1 | 0 | 3.09 | 2.63 |
| 2 | 0.05 | 3.11 | 2.75 |
| 3 | 0.15 | 3.3 | 2.96 |

Cowpea LAH clearly contributed to increased volume of the baked bread compared to the control, and the enzyme also contributed to improved crumb, with a more homogenous structure and a better appearance.

Results from lipid analysis of extracted lipids are shown in Table 4.

TABLE 4

GLC and HPLC Analyis of Dough Lipids

| Test no. | Monoglyceride ‰ | Diglyceride ‰ | Triglyceride ‰ | DGDG ‰ | DGMG ‰ |
|---|---|---|---|---|---|
| 1 | 0.43 | 0.99 | 4.94 | 2.09 | 0.22 |
| 2 | 0.43 | 0.95 | 4.98 | 2.03 | 0.27 |
| 3 | 0.43 | 0.96 | 5.11 | 1.92 | 0.28 |

The lipid analysis indicates that cowpea LAH does not hydrolyse the non-polar lipids. The level of triglyceride seem to increase a little, but this is within the experimental error. However, the enzyme clearly has an effect on the galactolipid in dough by degrading digalactolyldiglyceride (DGDG). An increase in the corresponding DGMG level is observed. The degree of hydrolysis of galactolipid is not very high, but sufficient to explain an improvement in baking quality of the enzyme.

Example 3

LAH isolated from cowpea was evaluated in baking tests as follows. The LAH was evaluated in hard crust rolls.

LAH was tested in a dosage of 0, 0.25, 0.5, 1 or 1.5 units enzyme/kg flour). Initial results show that the addition of 1.5 mg of LAH increased the loaf volume of the bread by more than 10% compared with bread with no enzyme and improved the dough handling properties.

Example 4

LAH was tested in bread according to the Danish toast bread procedure using Danish reform flour. LAH was tested at 0, 0.1, 0.25, 0.5, 1 or 1.5 units enzyme/kg flour. As references a dough was made without enzyme addition. After baking, the loaves were cooled and the loaf volume measured. Bread baked in tin with a lid were stored at ambient temperature and the crumb softness were evaluated after 1, 3 and 7 days storage at 22° C. wrapped in double plastic bags.

Initial results show that the addition of 1-1.5 units of LAH increases the loaf volume.

Initial results for firmness and elasticity show that LAH gives significantly softer crumb after 7 days storage compared with the control (without enzyme).

Preliminary results also show that LAH produces bread with a very good and homogeneous crumb structure.

Example 5

Cowpea LAH was tested in minibread in different concentrations according to Table 5.

TABLE 5

Baking test with cowpea LAH and fatty acid analysis of dough.

| Cowpea LAH Units/kg | Specific Bread volume, ml/g | Free fatty acid in dough, ‰ |
|---|---|---|
| 0 | 3.09 | 2.57 |
| 0.1195 | 3 | 2.72 |
| 0.239 | 3.2 | 2.81 |
| 0.478 | 3.15 | 3.07 |
| 0.956 | 3.15 | 3.28 |

Cowpea LAH clearly contributes to increased volume at low concentration (up to 0.239 Units/kg). At higher dosage there was no increase in volume but the crumb structure became more homogenous. Doughs from this experiment were extracted and the dough lipids isolated and analysed by HPLC and GLC as shown in Table 6.

TABLE 6

GLC and HPLC Analysis of Dough Lipids.

| Cowpea LAH % | Monoglyceride ‰ | Diglyceride ‰ | Triglyceride ‰ | DGDG ‰ | DGMG ‰ |
|---|---|---|---|---|---|
| 0 | 0.43 | 0.99 | 4.94 | 2.15 | 0.21 |
| 0.1195 | 0.40 | 0.96 | 5.04 | 2.08 | 0.23 |
| 0.239 | 0.41 | 1.23 | 5.21 | 2.01 | 0.20 |
| 0.478 | 0.43 | 0.90 | 5.09 | 1.89 | 0.24 |
| 0.956 | 0.41 | 1.01 | 5.23 | 1.60 | 0.20 |

The lipid analysis clearly confirms that cowpea LAH is not active on the nonpolar dough lipids (mono-di-and triglyceride), but the functionality is explained by the effect on polar lipids like digalactolyldiglyceride (DGDG), which are clearly hydrolysed. The results indicate some variations in level of di- and triglyceride, but the variations are random and not any indication of enzyme activity.

Example 6

Cowpea LAH was evaluated in minibread analysis. In this experiment the enzyme was tested alone and also in combination with a galactolipid isolated from oat. Results from the baking test and determination of free fatty acid are shown in Table 7.

TABLE 7

Cowpea LAH and Galactolipid(DGDG) in Minibread.

| Test no | DGDG, 55% pure % | Cowpea LAH Units/kg flour | Sp. Bread vol. Ml/g | Free fatty acid ‰ |
|---|---|---|---|---|
| 1 | 0 | 0 | 3 | 2.39 |
| 2 | 0.2 | 0 | 3.28 | 2.50 |
| 3 | 0 | 0.357 | 3.22 | 3.07 |
| 4 | 0.2 | 0.357 | 3.69 | 3.00 |

In this experiment it is shown that both cowpea LAH and galactolipid (55% DGDG) have a positive effect on the bread volume. Combining the two ingredients contribute to a clear synergistic effect as illustrated in Table 7. Both bread volume and crumb structure is significantly improved when cowpea LAH and DGDG are added.

Dough from this baking experiment was frozen and freeze dried and the dough lipid Extracted with water-saturated butanol. The isolated lipids were exposed to GLC and HPLC analyses. Results from these analyses are shown in Table 8.

TABLE 8

GLC and HPLC Analysis of Dough lipids.

| Test no. | DGDG, 55% pure % | Cowpea LAH Units/kg flour | DGDG ‰ | DGMG ‰ | Triglyceride ‰ |
|---|---|---|---|---|---|
| 1 | 0 | 0 | 2.07 | 0.15 | 5.94 |
| 2 | 0.2 | 0 | 2.89 | 0.15 | 5.60 |
| 3 | 0 | 0.357 | 1.93 | 0.23 | not detected |
| 4 | 0.2 | 0.357 | 2.4 | 0.25 | 5.82 |

When galactolipids (test no 2) are added to the dough more galactolipids (DGDG) are also detected by HPLC analysis. Cowpea LAH has a strong hydrolysing effect on DGDG The hydrolysing effect is very clear both without DGDG added (test no. 3) and especially when DGDG is added (test no. 4). It is also observed that the level of the product of hydrolysis, namely DGMG, increases when cowpea LAH is added. As seen in the other experiments cowpea LAH has no hydrolysing effect on triglyceride.

Example 7

Cowpea LAH was evaluated in minibread analysis in combination with soy oil (Table 9).

TABLE 9

Cowpea LAH and Soy Oil in Minibread.

| Test no | Soy oil % | Cowpea LAH Units/kg flour | Sp. Bread vol. Ml/g | Free fatty acid ‰ |
|---|---|---|---|---|
| 14 | 2 | 0 | 3.3 | 2.00 |
| 15 | 2 | 1.07 | 3.3 | 3.35 |
| 16 | 2 | 2.14 | 3.12 | 3.75 |

In this experiment the cowpea LAH did not contribute to improvement in bread volume compared to bread baked with soy oil alone, but cowpea LAH clearly improved the crumb structure and appearance of the bread (FIG. 8).

Example 8

Cowpea LAH was evaluated in minibread analysis in combination with different concentrations of galactolipid (55%pure) (Table 10).

TABLE 10

Cowpea LAH and Galactolipid (55% Pure) in Minibread

| Test no | DGDG, 55% pure % | Cowpea LAH Units/kg flour | Sp. Bread vol. ml/g | Free fatty acid ‰ |
|---|---|---|---|---|
| 9 | 0 | 0 | 3.03 | 2.60 |
| 10 | 0 | 1.07 | 3.11 | 3.32 |
| 11 | 0.1 | 1.07 | 3.3 | 3.42 |
| 12 | 0.2 | 1.07 | 3.73 | 3.64 |
| 13 | 0.4 | 1.07 | 4.13 | 3.92 |

Table 10 shows that the addition of galactolipid in combination with 1.07 Units/kg galactolipid contributes to a strong improvement in both bread volume and crumb structure (FIG. 9).

Example 9

Purified LAH from cowpea was tested in minibread in combination with galactolipid DGDG.

The addition of ingredients to the dough is outlined in Table 11, as well as the bread volume of bread from these baking experiments.

TABLE 11

Baking test with cowpea LAH and galactolipid DGDG

| Test no | DGDG, 55% pure % | Cowpea LAH Units/kg flour | Sp. Bread volume ml/g |
|---|---|---|---|
| 1 | 0 | 0 | 2.92 |
| 2 | 0.4 | 0 | 4.11 |
| 3 | 0.4 | 0.71 | 4.36 |
| 4 | 0 | 0.71 | 3.14 |

It is clearly shown from the results in Table 11 that DGDG has a very positive effect on bread volume of the baked bread. Cowpea LAH also contributes to improved bread volume. The combination of Cowpea LAH and DGDG gave further improvement in bread volume and a better crumb structure was observed (FIG. 10).

Example 10

In this experiment isolated membrane bound LAH from wheat leaf chloroplasts were tested in a 10 gram model dough system. The dough was rested for 1 hour at 26° C. and then frozen and freeze dried.

The freeze dried dough was extracted with water saturated butanol (WSB) and the isolated dough lipids were exposed to GLC and HPLC analysis. The results from the lipid analysis are shown in Table 12.

TABLE 12

Effect of Membrane Bound LAH from Wheat Chloroplast in Dough. GLC Analysis of Lipids.

| Membrane-bound LAH % in dough | Free fatty acid ‰ | Mono-glyceride ‰ | Diglyceride ‰ | Tri-glyceride ‰ | DGDG ‰ |
|---|---|---|---|---|---|
| 0.1 | 3.06 | 0.32 | 0.84 | 4.20 | 0.82 |
| 0.5 | 4.40 | 0.30 | 0.57 | 3.80 | 0.00 |
| 1 | 4.83 | 030 | 0.51 | 3.96 | 0.00 |
| 2 | 5.70 | 0.27 | 0.37 | 4.12 | 0.00 |

The results in Table 12 confirm the lipolytic activity of the membrane-bound LAH enzyme from wheat chloroplasts in dough measured as a strong increase in free fatty acid in the dough. The results also have shown that the membrane-bound LAH enzyme from wheat chloroplasts has almost no effect on non-polar lipids, and the concentration of triglyceride is unchanged. The results also indicate a strong hydrolytic effect of the membrane bound LAH enzyme from wheat chloroplasts on the hydrolysis of galactolipids like digalactosyl diglyceride (DGDG), which is completely hydrolysed at higher dosages of the membrane-bound LAH enzyme.

Example 11

In this experiment an isolated LAH enzyme comprising the sequence shown in SEQ ID No. 12 was tested in a 10 gram model dough system. The dough was rested for 1 hour at 26° C. and then frozen and freeze dried.

Preliminary results show the enzyme comprising the sequence shown in SEQ ID No. 12 reduces the amounts of polar lipids in the oil whilst not significantly affecting the triglyceride levels of the oil.

Conclusion:

LAH enzymes from cowpea have been isolated and characterised and tested in model dough and minibaking experiments. This enzyme is active on the polar galactolipids and phospholipids in dough but no activity on triglycerides in dough was observed. A chloroplast bound LAH from wheat leaves has also been isolated and tested in model dough. This enzyme is also active against galactolipids and phospholipids in dough, but showed no activity on triglycerides.

Example 12

Vegetable oil, in particular rapeseed oil, was treated with LAH isolated from cowpea to effect degumming of the oil. The process used was essentially as per the enzyme-catalysed degumming process of vegetable oil generally taught in Buchold, H. (Fat Sci. Technol. 95 Jahrgang nr. 8, 1993, pp300-305), excepting that LAH was used.

Preliminary results show LAH to reduce the amounts of polar lipids in the oil whilst not significantly affecting the triglyceride levels of the oil.

All publications mentioned in the above specification are herein incorporated by reference. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in food chemistry/technology and biochemistry are intended to be within the scope of the following claims.

SEQUENCE LISTING

```
<160> NUMBER OF SEQ ID NOS: 12

<210> SEQ ID NO 1
<211> LENGTH: 400
<212> TYPE: PRT
<213> ORGANISM: Vigna unguiculata

<400> SEQUENCE: 1

Met Ala Ala Thr Gln Thr Pro Ser Lys Val Asp Asp Gly Ala Leu Ile
1               5                   10                  15

Thr Val Leu Ser Ile Asp Gly Gly Gly Ile Arg Gly Ile Ile Pro Gly
            20                  25                  30

Ile Leu Leu Ala Phe Leu Glu Ser Glu Leu Gln Lys Leu Asp Gly Ala
        35                  40                  45

Asp Ala Arg Leu Ala Asp Tyr Phe Asp Val Ile Ala Gly Thr Ser Thr
    50                  55                  60

Gly Gly Leu Val Thr Ala Met Leu Thr Ala Pro Asn Glu Asn Asn Arg
65                  70                  75                  80

Pro Leu Tyr Ala Ala Lys Asp Ile Lys Asp Phe Tyr Leu Glu His Thr
                85                  90                  95

Pro Lys Ile Phe Pro Gln Ser Ser Ser Trp Asn Leu Ile Ala Thr Ala
            100                 105                 110

Met Lys Lys Gly Arg Ser Leu Met Gly Pro Gln Tyr Asp Gly Lys Tyr
        115                 120                 125

Leu His Lys Leu Val Arg Glu Lys Leu Gly Asn Thr Lys Leu Glu His
    130                 135                 140

Thr Leu Thr Asn Val Val Ile Pro Ala Phe Asp Ile Lys Asn Leu Gln
145                 150                 155                 160

Pro Ala Ile Phe Ser Ser Phe Gln Val Lys Lys Arg Pro Tyr Leu Asn
                165                 170                 175

Ala Ala Leu Ser Asp Ile Cys Ile Ser Thr Ser Ala Ala Pro Thr Tyr
            180                 185                 190

Leu Pro Ala His Cys Phe Glu Thr Lys Thr Ser Thr Ala Ser Phe Lys
        195                 200                 205

Phe Asp Leu Val Asp Gly Gly Val Ala Ala Asn Asn Pro Ala Leu Val
    210                 215                 220

Ala Met Ala Glu Val Ser Asn Glu Ile Arg Asn Glu Gly Ser Cys Ala
225                 230                 235                 240

Ser Leu Lys Val Lys Pro Leu Gln Tyr Lys Lys Phe Leu Val Ile Ser
```

```
                245                 250                 255

Leu Gly Thr Gly Ser Gln Gln His Glu Met Arg Tyr Ser Ala Asp Lys
            260                 265                 270

Ala Ser Thr Trp Gly Leu Val Gly Trp Leu Ser Ser Ser Gly Gly Thr
        275                 280                 285

Pro Leu Ile Asp Val Phe Ser His Ala Ser Ser Asp Met Val Asp Phe
    290                 295                 300

His Ile Ser Ser Val Phe Gln Ala Arg His Ala Glu Gln Asn Tyr Leu
305                 310                 315                 320

Arg Ile Gln Asp Asp Thr Leu Thr Gly Asp Leu Gly Ser Val Asp Val
                325                 330                 335

Ala Thr Glu Lys Asn Leu Asn Gly Leu Val Gln Val Ala Glu Ala Leu
            340                 345                 350

Leu Lys Lys Pro Val Ser Lys Ile Asn Leu Arg Thr Gly Ile His Glu
        355                 360                 365

Pro Val Glu Ser Asn Glu Thr Asn Ala Glu Ala Leu Lys Arg Phe Ala
    370                 375                 380

Ala Arg Leu Ser Asn Gln Arg Arg Phe Arg Lys Ser Gln Thr Phe Ala
385                 390                 395                 400


<210> SEQ ID NO 2
<211> LENGTH: 5331
<212> TYPE: DNA
<213> ORGANISM: Vigna unguiculata

<400> SEQUENCE: 2

caaattctat ataaaatata atacattagg aagttagaaa atacttgacc tactctccaa     60

ttatttgatt cacgttcaaa atatatcatt acgattctag attaataaag attcctataa    120

agtttcaaat cacaaatgtg accattcaat atctcacatg caaccaaaat aaggaaaaag    180

ccttaagttt aaaaaataaa taaaaagttt actcaaaacc aaaacttaat aagataaact    240

tttcttatat tctgttaaat tttattcccc atactttaat aaaagaaagg ataagaaaca    300

actacttttt attttacttt gtattttata gagataaaat agtttagata attgaaaagt    360

gaattagttt tacattatat ataactttta catactaaaa catttatttt tgttttaaat    420

taaagaaagg tacttacact agaaataacg tttataaatg aatgaaaatt acattcaatt    480

tcttaaaagt actgtgaata gaaaaatgat aacaaagaag aaaaatatat agtgaattat    540

attacaagaa aaaaaaagtt gtcaattaat tattaataca ttgcatcaat aataaataaa    600

ggttctcatt tttgtagtga aatctcaaat aagttttctc atttttattt gactcaattg    660

agttactaat ttggaaaatt cattgcaatt agatcatttt cgttagtact acactagcga    720

tgttaactat gtgtcatgtg tcagcaagtg attttttta taattttttt gaaaaaaata    780

aaaaaaaatt atcatgtgtt aatctgacat tgtgtcacat gttagagata atgtgatgtg    840

acagtaatag taccacatgt cactattgaa tgtgaaaagt cttaatataa tccttgtatt    900

tattattttg tttcaattta acatttttt aaacataaaa caatttaatt aatttttaa    960

atttcatatt ttctaaatat tttagataag taaaaaataa taataatacg attaaacctt   1020

aattttgtac tttacaacta ctatttgatg gttatgcttt taagttgtgg ttgaaatagt   1080

ggtgaagagc atacgtgaat atgacaaata aagaaacaaa cgcaattatg acattcttat   1140

ccttttctaa gtattttctt ataattacag tcttttgaaa ttattgtgta tgaaattaaa   1200

gtaggtatgt gggaatgtga caataataat aactaaggag actctgaaaa gttctgagaa   1260

tttaatgaat taattataat ttaaacaagt cagacaagaa aattataaag ttctctaacc   1320
```

```
tagtacgtgc ctcataaaat aatagtcatg ctattataaa ataattaatt atggtgggtg   1380
gaatgttcat tgacacaatt atttagatat tttctcattg actcattgac acatggttca   1440
ttgctatcca tctattacca atgaatatta ccttttgtcg tctatgataa tttattttta   1500
taattttaat actctatcaa agtaaaaata ttgtccagga aaaatgggtt ttattaataa   1560
ttaattgaag gtgaattaac tatactaaat attataccaa tggataatta cattgcaaaa   1620
gaataccttt gtagtatttt gaaatatgat attttaaagt aacttgttgt tcattaaaaa   1680
attaaaaatt taaatataag tttaagtctt acactaaaaa aaataaaaaa atataaagtt   1740
gagtatcata taaagatgaa aactcataaa acatattaga gttgaaggtt aatagtctat   1800
ttagacaaat ttttgtatcg agaaagaaat accgatggga catactcatg ggataaatca   1860
aaactaagtg aaaataaaat ttgaggtaaa gaaaatacat atttaataaa tttaaaagtg   1920
aaatttttaa tgtgtgtcca aaatatttgt taaataataa taaacatatt ttacatcacc   1980
taatccatgc gtttttcatc ggatttacgg gccggtccga cgggccagat cctaattgtc   2040
acccccttatg tattttatat atggtatata tgactaacat gagaaaatgt gaccgttaaa   2100
agcagagttt taatcaaaca taagtaaaaa tgagtatagt taaaccaaaa cttgatttac   2160
catatataac tcataacaga gactttaaca cagatctgca aaccttccta gtatgtacac   2220
tgcaaaaaca agggaacaca aaggttgccc tacgcattca atctcattaa tctctgtggt   2280
ccaaaacact ttgtgtgtat atgatttgaa tattactatt atacatccaa caatagtaat   2340
tcttgtcttt tgtgtctata tgatttgaac gctagtatta cattctctat caactcttcc   2400
atacatttat tgatcgcccc accatcaaaa aaccataact aacacgtgaa aactgataaa   2460
aataacgtca gcatagaagt tctgaacgtt caatattatt cacagaaaaa agatattatc   2520
catttcgacg tttttgtggt aattaactta acatggtgct aagattttgg tataggagat   2580
gatgttatat aggttacctt aattatgatt gaagtgagtg aagaattctt attcattgaa   2640
agtgttttta actgaggttt tagacaaact atacctaatt ttactagttt aatccctctt   2700
aagaaaaaaa aaccaactcc tggaacacca acaaacacca taagtaacac gtttgaaaac   2760
ggactaaaat aatgttgaag ctctcgacaa ttaaataggt ttcatggaaa catattatcc   2820
atttccctgt ttttgtggca actaattgaa cacgctaaaa acaagacaag taaactcacc   2880
aacatcttca ctctttacac ggtttggctt tatatataaa tatgcagttt ctcctcatca   2940
aatcaaccca tgaaaaccag atttttctga ataagtttgt gtaagagttc agtagttttc   3000
tttgctcttt cctaagttca ttccatctct ctttctttct ctttctttct cactgtgtgt   3060
gtctctctct ttctctttga cttagtaagt catcaattca gatccatggc agcaactcaa   3120
actccaagca aagttgatga tggagcactg attactgtgc tgagtattga tggtggtggc   3180
attcgtggaa tcattcccgg aattttgctt gctttcctcg aatcagaact tcaggtaata   3240
ataatctatg gtaaccaaga gaaaacgttt atatgtaaat taatgcagga aagtaactaa   3300
taatggtgca tatgcagaaa ctggatggtg ctgatgcaag actcgcagat tactttgatg   3360
tgattgcagg aacaagcacc ggtggattag tcactgcaat gctcactgct ccaaatgaaa   3420
ataatcgacc cttgtatgca gccaaagata taaaggattt ctaccttgag catacccccaa   3480
aaatcttccc gcagagtagg taaataccac actttacacc ataaacttcg taccaaatca   3540
ttcaaatcta aatacacact gtgtactaat ttacagtgtg atttttttccc aaatacagta   3600
gctggaattt gattgcaaca gcgatgaaga aaggcagaag tctgatggga ccacagtacg   3660
atggcaagta tttacacaag ctcgttaggg aaaaactagg gaacacaaaa ttggaacaca   3720
```

```
cattaaccaa tgtcgttatc ccagcatttg atatcaaaaa ccttcaaccc gccatctttt   3780

ccagcttcca ggttcacccc tcctcctctc aattgcaaaa agtcactcac ttgaaagcaa   3840

aaattgcagc tttttgtttt tctctaacga aattattact ctcgaatatg atgtcacagg   3900

tgaagaagag gccatatttg aatgcggcgt tgtctgatat atgcatttca acctcggcag   3960

caccaaccta tctcccagct cattgctttg aaactaaaac cagcactgct agtttcaaat   4020

tcgaccttgt agatggtggt gtagcagcaa ataacccggt attgtattat acagtctcag   4080

aactaatctt aatcattcat aacataatca cacacacaaa cactataatt aacaagtata   4140

aatttaatcg ataacagaag aaggtgatag atatgttata atctggcatt ttccaggctc   4200

tggtggcgat ggcagaagtg tcgaacgaaa tccgcaatga agggtcatgt gcaagcttga   4260

aagtaaaacc gttgcaatac aaaaagtttt tggtgatatc gttgggaaca ggttctcagc   4320

aacacgaaat gagatacagt gctgataagg catcgacatg gggccttgtg ggttggcttt   4380

cctcctccgg tggcactcct ctcatcgatg ttttcagcca tgctagttct gacatggttg   4440

atttccacat ctcctccgtt ttccaagcac gccatgctga acaaaactac ctccgaatcc   4500

aggttctttc cgaacatata tataaacatc ttcaatgatt ctcgtgcttg caaatgaaaa   4560

ctcatgagtt caatctttat attcaaattt tgcaggatga tactttaact ggggacttag   4620

gttcggtgga cgtggccacg gagaagaatc tgaatggcct cgtccaagtt gcggaagcat   4680

tgttaaagaa accagtttca aagattaact tgaggaccgg tattcatgaa cctgttgagt   4740

ctaacgaaac caacgcagaa gccttgaaga ggtatatata tatcaaaacc ctactcatac   4800

acacacatga taatggaaag aatttaagaa aaactgtgta agaaattaaa gtatatatac   4860

aataaaaaca tcatgtgttc atcgtactaa tgttttatta acaacgtatt ttttatcaaa   4920

cgaaatccat atatgagttg taacttcttc gaatcacagt ttcacgttca cttcacttca   4980

ctatttttt atatcaggtt tgcggcacga ctatccaacc agaggagatt tcggaaatct   5040

caaacgtttg cgtagaatgg gaatcttcga aagatgaaga tatacgagac acgtgttgct   5100

tggccaatat gataaatgat tggtgtagtg tttatcttaa ttttatatat ttttctttat   5160

atttcgtagt gttcattaca gtgaagatat attcattgta ctgaatcaca ataattagtg   5220

tccctacaat attaaatctc atgtgctgta aacgctttgt gtttctttgt tttcatttac   5280

caatgtaatc agtttggttc actatattgt ctctaattca ttttatttta a            5331
```

<210> SEQ ID NO 3
<211> LENGTH: 297
<212> TYPE: PRT
<213> ORGANISM: Aspergillus tubingensis

<400> SEQUENCE: 3

```
Met Phe Ser Gly Arg Phe Gly Val Leu Leu Thr Ala Leu Ala Ala Leu
1               5                   10                  15

Gly Ala Ala Ala Pro Ala Pro Leu Ala Val Arg Ser Val Ser Thr Ser
            20                  25                  30

Thr Leu Asp Glu Leu Gln Leu Phe Ala Gln Trp Ser Ala Ala Ala Tyr
        35                  40                  45

Cys Ser Asn Asn Ile Asp Ser Lys Asp Ser Asn Leu Thr Cys Thr Ala
    50                  55                  60

Asn Ala Cys Pro Ser Val Glu Glu Ala Ser Thr Thr Met Leu Leu Glu
65                  70                  75                  80

Phe Asp Leu Thr Asn Asp Phe Gly Gly Thr Ala Gly Phe Leu Ala Ala
                85                  90                  95
```

```
Asp Asn Thr Asn Lys Arg Leu Val Val Ala Phe Arg Gly Ser Ser Thr
            100                 105                 110

Ile Glu Asn Trp Ile Ala Asn Leu Asp Phe Ile Leu Glu Asp Asn Asp
        115                 120                 125

Asp Leu Cys Thr Gly Cys Lys Val His Thr Gly Phe Trp Lys Ala Trp
    130                 135                 140

Glu Ser Ala Ala Asp Glu Leu Thr Ser Lys Ile Lys Ser Ala Met Ser
145                 150                 155                 160

Thr Tyr Ser Gly Tyr Thr Leu Tyr Phe Thr Gly His Ser Leu Gly Gly
                165                 170                 175

Ala Leu Ala Thr Leu Gly Ala Thr Val Leu Arg Asn Asp Gly Tyr Ser
            180                 185                 190

Val Glu Leu Tyr Thr Tyr Gly Cys Pro Arg Ile Gly Asn Tyr Ala Leu
        195                 200                 205

Ala Glu His Ile Thr Ser Gln Gly Ser Gly Ala Asn Phe Arg Val Thr
    210                 215                 220

His Leu Asn Asp Ile Val Pro Arg Val Pro Pro Met Asp Phe Gly Phe
225                 230                 235                 240

Ser Gln Pro Ser Pro Glu Tyr Trp Ile Thr Ser Gly Asn Gly Ala Ser
                245                 250                 255

Val Thr Ala Ser Asp Ile Glu Val Ile Glu Gly Ile Asn Ser Thr Ala
            260                 265                 270

Gly Asn Ala Gly Glu Ala Thr Val Ser Val Val Ala His Leu Trp Tyr
        275                 280                 285

Phe Phe Ala Ile Ser Glu Cys Leu Leu
    290                 295


<210> SEQ ID NO 4
<211> LENGTH: 894
<212> TYPE: DNA
<213> ORGANISM: Aspergillus tubingensis

<400> SEQUENCE: 4

atgttctctg gacggtttgg agtgcttttg acagcgcttg ctgcgctggg tgctgccgcg      60

ccggcaccgc ttgctgtgcg gagtgtctcg acttccacgt tggatgagtt gcaattgttc     120

gcgcaatggt ctgccgcagc ttattgctcg aataatatcg actcgaaaga ctccaacttg     180

acatgcacgg ccaacgcctg tccatcagtc gaggaggcca gtaccacgat gctgctggag     240

ttcgacctga cgaacgactt tggaggcaca gccggtttcc tggccgcgga caacaccaac     300

aagcggctcg tggtcgcctt ccggggaagc agcacgattg agaactggat tgctaatctt     360

gacttcatcc tggaagataa cgacgacctc tgcaccggct gcaaggtcca tactggtttc     420

tggaaggcat gggagtccgc tgccgacgaa ctgacgagca agatcaagtc tgcgatgagc     480

acgtattcgg gctataccct atacttcacc gggcacagtt tgggcggcgc attggctacg     540

ctgggagcga cagttctgcg aaatgacgga tatagcgttg agctgtacac ctatggatgt     600

cctcgaatcg gaaactatgc gctggctgag catatcacca gtcagggatc tggggccaac     660

ttccgtgtta cacacttgaa cgacatcgtc ccccgggtgc cacccatgga ctttggattc     720

agtcagccaa gtccggaata ctggatcacc agtggcaatg gagccagtgt cacggcgtcg     780

gatatcgaag tcatcgaggg aatcaattca acggcgggaa atgcaggcga agcaacggtg     840

agcgttgtgg ctcacttgtg gtactttttt gcgatttccg agtgcctgct ataa           894


<210> SEQ ID NO 5
```

<211> LENGTH: 51
<212> TYPE: DNA
<213> ORGANISM: Artificial Sequence
<220> FEATURE:
<221> NAME/KEY: primer_bind
<222> LOCATION: (1)..(51)
<223> OTHER INFORMATION: lipase primer JOM1

<400> SEQUENCE: 5 caagctatac caagcataca atcaactcca aaatgttctc tggacggttt g 51

<210> SEQ ID NO 6
<211> LENGTH: 29
<212> TYPE: DNA
<213> ORGANISM: Artificial Sequence
<220> FEATURE:
<221> NAME/KEY: primer_bind
<222> LOCATION: (1)..(29)
<223> OTHER INFORMATION: lipase primer JOM2

<400> SEQUENCE: 6 caaacctctg gcgaagaagt ccaaagctg 29

<210> SEQ ID NO 7
<211> LENGTH: 21
<212> TYPE: DNA
<213> ORGANISM: Artificial Sequence
<220> FEATURE:
<221> NAME/KEY: primer_bind
<222> LOCATION: (1)..(21)
<223> OTHER INFORMATION: lipase primer JOM3

<400> SEQUENCE: 7 gctcgtggtc gccttccggg g 21

<210> SEQ ID NO 8
<211> LENGTH: 19
<212> TYPE: DNA
<213> ORGANISM: Artificial Sequence
<220> FEATURE:
<221> NAME/KEY: primer_bind
<222> LOCATION: (1)..(19)
<223> OTHER INFORMATION: lipase primer JOM4

<400> SEQUENCE: 8 gccggtgcag aggtcgtcg 19

<210> SEQ ID NO 9
<211> LENGTH: 22
<212> TYPE: DNA
<213> ORGANISM: Artificial Sequence
<220> FEATURE:
<221> NAME/KEY: primer_bind
<222> LOCATION: (1)..(22)
<223> OTHER INFORMATION: lipase primer JOM5

<400> SEQUENCE: 9 cctcgaatcg gaaactatgc gc 22

<210> SEQ ID NO 10
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: lipase primer JOM13

<400> SEQUENCE: 10

```
tgtcacggcg tcggatatcg                                                  20


<210> SEQ ID NO 11
<211> LENGTH: 20
<212> TYPE: DNA
<213> ORGANISM: Artificial Sequence
<220> FEATURE:
<221> NAME/KEY: primer_bind
<222> LOCATION: (1)..(20)
<223> OTHER INFORMATION: lipase primer JOM14

<400> SEQUENCE: 11

ctcatccaac gtggaagtcg                                                  20


<210> SEQ ID NO 12
<211> LENGTH: 406
<212> TYPE: PRT
<213> ORGANISM: wheat derivative

<400> SEQUENCE: 12

Met Cys Ser Gln Ala Asp Pro Thr Leu Thr Cys Pro Pro Pro Ser Gln
1               5                   10                  15

Gly Arg Leu Ile Thr Val Leu Ser Ile Asp Gly Gly Gly Ile Arg Gly
            20                  25                  30

Leu Ile Pro Ser Thr Ile Leu Ala Cys Leu Glu Ser Lys Leu Gln Glu
        35                  40                  45

Leu Asp Gly Pro Asp Ala Arg Ile Ala Asp Tyr Phe Asp Val Ile Ala
    50                  55                  60

Gly Thr Ser Thr Gly Ala Leu Val Thr Ser Met Leu Ala Ala Pro Gly
65                  70                  75                  80

Glu Asn Lys Arg Pro Leu Phe Glu Ala Lys Asp Ile Asn Lys Phe Tyr
                85                  90                  95

Leu Asp Asn Gly Pro Lys Ile Phe Pro Gln Lys Gly Trp Gly Val Leu
            100                 105                 110

Thr Pro Met Ala Asn Leu Phe Gly Ala Val Thr Gly Pro Lys Tyr Asp
        115                 120                 125

Gly Lys Phe Leu His Asp Lys Ile Lys Ser Leu Thr Asn Asp Val Thr
    130                 135                 140

Val Ala Asp Thr Val Thr Asn Ile Ile Val Pro Thr Phe Asp Ile Lys
145                 150                 155                 160

Tyr Leu Gln Pro Ile Ile Phe Asn Thr Tyr Glu Ala Lys Val Asp Pro
                165                 170                 175

Leu Lys Asn Ala His Leu Ser Asp Ile Cys Ile Ser Thr Ser Ala Ala
            180                 185                 190

Pro Thr Tyr Phe Pro Ala His Tyr Phe Thr Thr Arg Asp Pro Ala Gly
        195                 200                 205

Lys Leu Pro Asp Arg Glu Tyr His Leu Ile Asp Gly Gly Val Ala Ala
    210                 215                 220

Asn Asn Pro Thr Met Ala Ala Met Ser Met Ile Thr Lys Glu Val Leu
225                 230                 235                 240

Arg Arg Asn Pro Asp Phe Thr His Gly Lys Pro Ala Glu Tyr Gly Asn
                245                 250                 255

Tyr Leu Ile Ile Ser Ile Gly Thr Gly Ser Ala Lys Met Ala Glu Lys
            260                 265                 270

Tyr Thr Ala Pro Asp Cys Ala Lys Trp Gly Val Leu Arg Trp Leu Tyr
        275                 280                 285

Asp Gly Gly Phe Thr Pro Leu Ile Asp Ile Phe Ser His Ala Ser Ala
    290                 295                 300
```

-continued

```
Asp Met Val Asp Ile Gln Ala Ser Val Leu Phe Gln Val Leu Asp Cys
305                 310                 315                 320

Thr Lys Ser Tyr Val Arg Ile Gln His Ala Glu Leu Thr Gly Glu Met
                325                 330                 335

Ala Ser Val Tyr Val Ser Thr Ser Lys Ser Leu Asn Gly Phe Ile Ser
            340                 345                 350

Val Gly Lys Ala Leu Leu Lys Lys Gln Val Cys Lys Val Asn Val Glu
        355                 360                 365

Thr Gly Lys Asn Glu Pro Asp Leu Glu Arg Gly Ala Tyr Glu Glu Glu
    370                 375                 380

Leu Ala Arg Phe Val Arg Met Leu Ser Lys Glu Arg Lys Ala Arg Lys
385                 390                 395                 400

Glu Ala Tyr Lys Leu Val
                405
```

What is claimed is:

1. A method of preparing a flour dough, said method comprising adding to the dough components an enzyme that under dough conditions is capable of hydrolyzing a glycolipid and a phospholipid, wherein said enzyme is incapable, or substantially incapable, of hydrolyzing a triglyceride and/or a 1-monoglyceride, and mixing the dough components to obtain the dough.

2. A method according to claim 1 wherein the enzyme is incapable, or substantially incapable, of hydrolyzing both a triglyceride and a 1-monoglyceride.

3. A method according to claim 1 wherein the enzyme is capable of hydrolyzing a triglyceride and a diglyceride and wherein said enzyme is incapable, or substantially incapable, of hydrolyzing a 1-monoglyceride.

4. A method according to claim 1 wherein at least one of the triglyceride, the 1-monoglyceride, the glycolipid and the phospholipid is a naturally occurring lipid component occurring in flour used for the dough.

5. A method according to claim 1 wherein the phospholipid is phosphatidylcholine (PC).

6. A method according to claim 1 wherein the glycolipid is digalactosyldiglyceride (DGDG).

7. A method according to claim 1 wherein at least one of the triglyceride, the 1-monoglyceride, the glycolipid and the phospholipid is added to the dough.

8. A method according to claim 7 wherein the triglyceride is selected from the group consisting of a vegetable oil, a vegetable fat, an animal fat, shortening and milk fat.

9. A method according to claim 8 wherein the vegetable oil is a naturally occurring cereal oil.

10. A method according to claim 7 wherein the phospholipid is selected from the group consisting of phosphotidylinositol (PI), phosphatidylglycerol (PG), phosphatidylcholine (PC) and phosphatidylethanolamine (PE).

11. A method according to claim 1 wherein the dough is a yeast leavened dough.

12. A method according to claim 1 wherein the enzyme is added in an amount which is in the range of 0.1 to 1000 units enzyme/kg flour.

13. A method according to claim 12 wherein the enzyme is added in an amount which is in the range of 1 to 100 units enzyme/kg flour.

14. A method according to claim 1 wherein the dough is a bread dough, the method comprising as a further step that the dough is baked to obtain a baked product.

15. A method according to claim 1 wherein the dough is selected from the group consisting of a pasta dough, a noodle dough, a cake dough and a cake batter.

16. A method according to claim 1 wherein the enzyme is added in an amount that results in an increase of the specific volume of the baked product that is at least 10%, relative to a baked product made under identical conditions except that the enzyme is not added.

17. A method according to claim 1 wherein a further enzyme is added to the dough.

18. A method according to claim 17 wherein the further enzyme is selected from the group consisting of a lipase, a starch degrading enzyme, a hemicellulase, a cellulose, and an oxidoreductase.

19. A method according to claim 1 wherein at least 25% of the glycolipid initially present in the dough is hydrolysed.

20. A method according to claim 1 wherein at least 25% of the phospholipid initially present in the dough is hydrolysed.

21. A method according to claim 1 wherein the enzyme has hydrolytic activity against a phospholipid and a glycolipid but no, or substantially no, hydrolytic activity against a triglyceride and/or a 1-monoglyceride in the pH range of 4.5-6.5.

22. A dough improving composition comprising an enzyme that, under dough conditions, is capable of hydrolyzing a glycolipid and a phospholipids, wherein said enzyme is incapable, or substantially incapable, of hydrolyzing a triglyceride and/or a 1-monoglyceride, and one further dough component selected from the group consisting of cereal flour, yeast, a chemical leavening agent, a dough strengthening agent, and an emulsifier.

23. A composition according to claim 22 wherein the enzyme is incapable, or substantially incapable, of hydrolyzing both a triglyceride and a 1-monoglyceride.

24. A composition according to claim 22 wherein the enzyme is capable of hydrolyzing a triglyceride and a diglyceride and wherein said enzyme is incapable, or substantially incapable, of hydrolyzing a 1-monoglyceride.

25. A composition according to claim 22 wherein said composition comprises a further enzyme selected from the group consisting of a lipase, a starch degrading enzyme, a hemicellulase, a cellulase, and an oxidoreductase.

26. A dough obtainable by the method according to claim 1.

27. A dough according to claim 26 wherein said dough is frozen or packaged in a controlled atmosphere.

28. A baked product obtainable by baking a dough according to claim 26.

29. A noodle product made from a dough according to claim 26.

30. A pasta product made from a dough according to claim 26.

31. A dough composition comprising an enzyme that, under dough conditions, is capable of hydrolyzing a glycolipid and a phospholipids, wherein said enzyme is incapable, or substantially incapable, of hydrolyzing a triglyceride and/or a 1-monoglyceride.

32. The method of claim [8] *9* wherein the cereal oil comprises oat oil.

*33. A method of preparing a flour dough, said method comprising adding to the dough components an enzyme that under dough conditions is capable of hydrolyzing a glycolipid and a phospholipid, wherein said enzyme is incapable, or substantially incapable, of hydyrolyzing a triglyceride and/or a 1-monoglyceride, and mixing the dough components to obtain the dough, wherein a least one of the triglyceride, the 1-monoglyceride, the glyoclipid and the phospholipid is added to the dough, and the triclyceride comprises cereal oil.*

*34. The method according to claim 33 wherein the cereal oil comprises oat oil.*

* * * * *